United States Patent
Shang et al.

(10) Patent No.: US 9,561,328 B2
(45) Date of Patent: Feb. 7, 2017

(54) AUTOMATIC INJECTION DEVICE

(71) Applicant: AbbVie Biotechnology Ltd, Hamilton (BM)

(72) Inventors: Sherwin S. Shang, Vernon Hills, IL (US); Esra Ozdaryal, Deerfield, IL (US); Marc M. Plew, Gurnee, IL (US); William P. Szechinski, Chicago, IL (US)

(73) Assignee: ABBVIE BIOTECHNOLOGY LTD, Hamilton (BM)

( * ) Notice: Subject to any disclaimer, the term of this patent is extended or adjusted under 35 U.S.C. 154(b) by 171 days.

(21) Appl. No.: 14/109,532

(22) Filed: Dec. 17, 2013

(65) Prior Publication Data
US 2015/0011948 A1 Jan. 8, 2015

Related U.S. Application Data

(63) Continuation of application No. 12/770,557, filed on Apr. 29, 2010, now Pat. No. 8,636,704.
(Continued)

(51) Int. Cl.
*A61M 5/315* (2006.01)
*A61M 5/20* (2006.01)
*A61M 5/32* (2006.01)

(52) U.S. Cl.
CPC ............ *A61M 5/31511* (2013.01); *A61M 5/20* (2013.01); *A61M 5/2033* (2013.01);
(Continued)

(58) Field of Classification Search
CPC .. A61M 5/20; A61M 5/2033; A61M 5/31511; A61M 5/3157; A61M 5/31578; A61M 5/3202; A61M 2005/206; A61M 2005/2073
(Continued)

(56) References Cited

U.S. PATENT DOCUMENTS 2,398,544 A 4/1946 Lockhart
2,459,875 A 1/1949 Folkman
(Continued)

FOREIGN PATENT DOCUMENTS

CA 2682703 A1 10/2008
CA 2741354 A1 4/2010
(Continued)

OTHER PUBLICATIONS

Decision of Grant issued in Russian Application No. 2011148399, received Feb. 26, 2014. English translation.
(Continued)

*Primary Examiner* — Bhisma Mehta
*Assistant Examiner* — Larry R Wilson
(74) *Attorney, Agent, or Firm* — McCarter & English, LLP; David R. Burns

(57) ABSTRACT

Exemplary embodiments provide a syringe plunger formed of a polymeric material. The syringe plunger includes a pressurizer disposed at a proximal end, and a distal end bifurcated into a first plunger arm having a first conical surface and a second conical surface, and a second plunger arm having a first conical surface and a second conical surface. The distal end includes a first contact surface defined by the first conical surface of the first plunger arm and the first conical surface of the second plunger arm, the first contact surface configured to initially contact a firing engagement mechanism, the first contact surface disposed at a first angle of between about 40° and about 80° relative to a longitudinal axis of the syringe plunger. The distal end also includes a second contact surface defined by the second conical surface of the first plunger arm and the second conical surface of the second plunger arm, the second contact surface configured to contact the firing engagement
(Continued)

mechanism subsequent to contact by the first contact surface.

24 Claims, 37 Drawing Sheets

Related U.S. Application Data

(60) Provisional application No. 61/286,766, filed on Dec. 15, 2009, provisional application No. 61/173,952, filed on Apr. 29, 2009.

(52) U.S. Cl.
CPC ....... *A61M 5/31578* (2013.01); *A61M 5/3157* (2013.01); *A61M 5/3202* (2013.01); *A61M 2005/206* (2013.01); *A61M 2005/2073* (2013.01); *A61M 2205/584* (2013.01); *Y10T 29/49826* (2015.01)

(58) Field of Classification Search
USPC ... 604/68–72, 131, 134–136, 138, 141, 156, 604/157, 181, 187, 220, 228
See application file for complete search history.

(56) References Cited

U.S. PATENT DOCUMENTS

| | | |
|---|---|---|
| 2,565,081 A | 8/1951 | Maynes |
| 2,591,457 A | 4/1952 | Maynes |
| 2,701,566 A | 2/1955 | Krug |
| 2,752,918 A | 7/1956 | Uytenbogaart |
| 2,832,339 A | 4/1958 | Sarnoff et al. |
| 2,888,924 A | 6/1959 | Dunmire |
| 2,960,087 A | 11/1960 | Uytenbogaart |
| 3,051,173 A | 8/1962 | Johnson at al. |
| 3,055,362 A | 9/1962 | Uytenbogaart |
| 3,066,670 A | 12/1962 | Stauffer |
| 3,136,313 A | 6/1964 | Enstrom at al. |
| 3,314,428 A | 4/1967 | Johnson at al. |
| 3,330,279 A | 7/1967 | Sarnoff at al. |
| 3,403,680 A | 10/1968 | Sinclair et al. |
| 3,543,603 A | 12/1970 | Gley |
| 3,605,743 A | 9/1971 | Arce |
| 3,618,603 A | 11/1971 | Levenson |
| 3,702,609 A | 11/1972 | Steiner |
| 3,712,301 A | 1/1973 | Sarnoff |
| 3,742,948 A | 7/1973 | Post et al. |
| 3,797,488 A | 3/1974 | Hurschman et al. |
| 3,797,489 A | 3/1974 | Sarnoff |
| 3,882,863 A | 5/1975 | Sarnoff et al. |
| 3,892,237 A | 7/1975 | Steiner |
| 3,910,260 A | 10/1975 | Sarnoff et al. |
| 3,941,130 A | 3/1976 | Tibbs |
| 4,004,577 A | 1/1977 | Sarnoff |
| 4,031,893 A | 6/1977 | Kaplan et al. |
| 4,106,770 A | 8/1978 | Gray |
| 4,178,928 A | 12/1979 | Tischlinger |
| 4,202,314 A | 5/1980 | Smirnov et al. |
| 4,214,584 A | 7/1980 | Smirnov et al. |
| 4,226,235 A | 10/1980 | Sarnoff et al. |
| 4,258,713 A | 3/1981 | Wardlaw |
| 4,261,358 A | 4/1981 | Vargas et al. |
| 4,275,729 A | 6/1981 | Silver et al. |
| 4,316,463 A | 2/1982 | Schmitz et al. |
| 4,394,863 A | 7/1983 | Bartner |
| 4,425,120 A | 1/1984 | Sampson et al. |
| 4,437,859 A | 3/1984 | Whitehouse et al. |
| 4,447,231 A | 5/1984 | Bekkering |
| 4,530,695 A | 7/1985 | Phillips et al. |
| 4,565,543 A | 1/1986 | Bekkering et al. |
| 4,573,976 A | 3/1986 | Sampson et al. |
| 4,578,064 A | 3/1986 | Sarnoff et al. |
| 4,624,660 A | 11/1986 | Mijers et al. |
| 4,637,403 A | 1/1987 | Garcia et al. |
| 4,664,653 A | 5/1987 | Sagstetter et al. |
| 4,678,461 A | 7/1987 | Mesa |
| 4,689,042 A | 8/1987 | Sarnoff et al. |
| 4,723,937 A | 2/1988 | Sarnoff et al. |
| 4,755,169 A | 7/1988 | Sarnoff et al. |
| 4,795,432 A | 1/1989 | Karczmer |
| 4,795,433 A | 1/1989 | Sarnoff |
| 4,816,397 A | 3/1989 | Boss et al. |
| 4,820,286 A | 4/1989 | van der Wal |
| 4,822,340 A | 4/1989 | Kamstra |
| 4,850,994 A | 7/1989 | Zerbst et al. |
| 4,852,768 A | 8/1989 | Bartsch |
| 4,902,279 A | 2/1990 | Schmidtz et al. |
| 4,923,447 A | 5/1990 | Morgan |
| 4,927,416 A | 5/1990 | Tomkiel |
| 4,929,237 A | 5/1990 | Medway |
| 4,955,868 A | 9/1990 | Klein |
| 4,966,592 A | 10/1990 | Burns et al. |
| 4,994,034 A | 2/1991 | Botich et al. |
| 5,041,088 A | 8/1991 | Ritson et al. |
| 5,042,977 A | 8/1991 | Bechtold et al. |
| 5,049,133 A | 9/1991 | Villen Pascual |
| D322,479 S | 12/1991 | Miyaguchi |
| 5,071,353 A | 12/1991 | van der Wal |
| 5,085,641 A | 2/1992 | Sarnoff et al. |
| 5,085,642 A | 2/1992 | Sarnoff et al. |
| 5,092,842 A | 3/1992 | Bechtold et al. |
| 5,092,843 A | 3/1992 | Monroe et al. |
| 5,102,393 A | 4/1992 | Sarnoff et al. |
| 5,104,380 A | 4/1992 | Holman et al. |
| 5,114,406 A | 5/1992 | Gabriel et al. |
| 5,114,410 A | 5/1992 | Caralt Batlle |
| 5,137,516 A | 8/1992 | Rand et al. |
| 5,163,918 A | 11/1992 | Righi et al. |
| 5,201,708 A | 4/1993 | Martin |
| 5,242,240 A | 9/1993 | Gorham |
| 5,244,465 A | 9/1993 | Michel |
| 5,259,840 A | 11/1993 | Boris |
| 5,263,934 A | 11/1993 | Haak |
| 5,267,963 A | 12/1993 | Bachynsky |
| 5,267,972 A | 12/1993 | Anderson |
| 5,267,976 A | 12/1993 | Guerineau et al. |
| 5,273,544 A | 12/1993 | van der Wal |
| D343,897 S | 2/1994 | Rand et al. |
| 5,295,965 A * | 3/1994 | Wilmot ............ A61M 5/2033 604/136 |
| 5,295,975 A | 3/1994 | Lockwood, Jr. |
| 5,298,024 A | 3/1994 | Richmond |
| D346,219 S | 4/1994 | Fardigh |
| 5,300,030 A | 4/1994 | Crossman et al. |
| 5,318,538 A | 6/1994 | Martin |
| 5,320,609 A | 6/1994 | Haber et al. |
| 5,334,144 A | 8/1994 | Alchas et al. |
| 5,342,308 A | 8/1994 | Boschetti |
| 5,346,480 A | 9/1994 | Hess et al. |
| 5,358,489 A | 10/1994 | Wyrick |
| 5,376,080 A | 12/1994 | Petrussa |
| 5,378,233 A | 1/1995 | Haber et al. |
| 5,383,865 A | 1/1995 | Michel |
| 5,391,151 A | 2/1995 | Wilmot |
| 5,425,715 A | 6/1995 | Dalling et al. |
| 5,433,712 A | 7/1995 | Stiles et al. |
| 5,478,316 A | 12/1995 | Bitdinger et al. |
| 5,480,387 A | 1/1996 | Gabriel et al. |
| 5,530,101 A | 6/1996 | Queen et al. |
| 5,531,705 A | 7/1996 | Alter et al. |
| 5,569,192 A | 10/1996 | van der Wal |
| 5,585,089 A | 12/1996 | Queen et al. |
| 5,591,138 A | 1/1997 | Vaillancourt |
| 5,599,309 A | 2/1997 | Marshall et al. |
| 5,599,314 A | 2/1997 | Neill |
| 5,616,128 A | 4/1997 | Meyer |
| 5,620,421 A | 4/1997 | Schmitz |
| 5,634,906 A | 6/1997 | Haber et al. |
| 5,637,094 A | 6/1997 | Stewart, Jr. et al. |
| 5,645,534 A | 7/1997 | Chanoch |
| 5,658,259 A | 8/1997 | Pearson et al. |
| 5,681,291 A | 10/1997 | Galli |

(56) References Cited

U.S. PATENT DOCUMENTS

| | | |
|---|---|---|
| 5,779,677 A | 7/1998 | Frezza |
| 5,807,335 A | 9/1998 | Kriesel et al. |
| 5,807,346 A | 9/1998 | Frezza |
| 5,817,111 A | 10/1998 | Riza |
| 5,843,036 A | 12/1998 | Olive et al. |
| 5,860,957 A | 1/1999 | Jacobsen et al. |
| 5,885,250 A | 3/1999 | Kriesel et al. |
| 5,931,817 A | 8/1999 | Nguyen et al. |
| 5,957,886 A | 9/1999 | Weston |
| 5,957,897 A | 9/1999 | Jeffrey |
| 5,984,900 A | 11/1999 | Mikkelsen |
| 5,993,421 A | 11/1999 | Kriesel |
| 6,048,336 A | 4/2000 | Gabriel |
| 6,056,728 A | 5/2000 | von Schuckmann |
| 6,077,247 A | 6/2000 | Marshall et al. |
| D428,651 S | 7/2000 | Andersson et al. |
| 6,090,070 A | 7/2000 | Hager et al. |
| 6,090,080 A | 7/2000 | Jost et al. |
| 6,099,503 A | 8/2000 | Stradella |
| 6,102,896 A | 8/2000 | Roser |
| 6,110,147 A | 8/2000 | Perouse |
| 6,149,626 A | 11/2000 | Bachynsky et al. |
| 6,159,181 A | 12/2000 | Crossman et al. |
| 6,171,285 B1 | 1/2001 | Johnson |
| 6,203,530 B1 | 3/2001 | Stewart, Sr. |
| 6,210,369 B1 | 4/2001 | Wilmot et al. |
| 6,213,987 B1 | 4/2001 | Hirsch et al. |
| 6,221,044 B1 | 4/2001 | Greco |
| 6,241,709 B1 | 6/2001 | Bechtold et al. |
| 6,258,068 B1 | 7/2001 | Kirchhofer et al. |
| 6,270,479 B1 | 8/2001 | Bergens et al. |
| 6,277,097 B1 | 8/2001 | Mikkelsen et al. |
| 6,277,098 B1 | 8/2001 | Klitmose et al. |
| 6,277,099 B1 | 8/2001 | Strowe et al. |
| 6,280,421 B1 | 8/2001 | Kirchhofer et al. |
| 6,312,412 B1 | 11/2001 | Saied et al. |
| 6,319,233 B1 | 11/2001 | Jansen et al. |
| 6,319,234 B1 | 11/2001 | Restelli et al. |
| 6,322,540 B1 | 11/2001 | Grabis et al. |
| D453,569 S | 2/2002 | Himbert |
| 6,371,939 B2 | 4/2002 | Bergens et al. |
| 6,387,074 B1 | 5/2002 | Horppu et al. |
| 6,387,078 B1 | 5/2002 | Gillespie, III |
| 6,413,237 B1 | 7/2002 | Caizza et al. |
| 6,419,658 B1 | 7/2002 | Restelli et al. |
| D461,555 S | 8/2002 | Binet et al. |
| 6,448,380 B2 | 9/2002 | Rathjen et al. |
| 6,454,746 B1 | 9/2002 | Bydlon et al. |
| 6,475,194 B2 | 11/2002 | Domici, Jr. et al. |
| 6,502,699 B1 | 1/2003 | Watson |
| 6,517,517 B1 | 2/2003 | Farrugia et al. |
| 6,544,234 B1 | 4/2003 | Gabriel |
| 6,575,939 B1 | 6/2003 | Brunel |
| 6,589,210 B1 | 7/2003 | Rolfe |
| 6,656,163 B1 | 12/2003 | Marshall et al. |
| 6,656,164 B1 | 12/2003 | Smith |
| 6,673,035 B1 | 1/2004 | Rice et al. |
| 6,692,469 B1 | 2/2004 | Weekes et al. |
| 6,712,788 B2 | 3/2004 | Righi et al. |
| 6,743,203 B1 | 6/2004 | Pickhard |
| 6,752,798 B2 | 6/2004 | McWethy et al. |
| 6,767,336 B1 | 7/2004 | Kaplan |
| D494,270 S | 8/2004 | Reschke |
| 6,773,415 B2 | 8/2004 | Heiniger |
| 6,796,967 B2 | 9/2004 | Jensen |
| 6,802,827 B2 | 10/2004 | Andersson |
| 6,805,686 B1 | 10/2004 | Fathallah et al. |
| 6,808,507 B2 | 10/2004 | Roser |
| 6,817,989 B2 | 11/2004 | Svendsen et al. |
| 6,872,194 B2 | 3/2005 | Doyle et al. |
| 6,926,697 B2 | 8/2005 | Malenchek |
| 6,932,793 B1 | 8/2005 | Marshall et al. |
| 6,945,960 B2 | 9/2005 | Barker et al. |
| 6,976,976 B2 | 12/2005 | Doyle |
| 6,986,760 B2 | 1/2006 | Giambattista et al. |
| 7,004,929 B2 | 2/2006 | McWethy et al. |
| D518,175 S | 3/2006 | Hardin, Jr. et al. |
| 7,056,306 B1 | 6/2006 | Halseth et al. |
| D545,439 S | 6/2007 | Draudt et al. |
| 7,320,682 B2 | 1/2008 | Cocker et al. |
| 7,361,160 B2 | 4/2008 | Hommann et al. |
| 7,416,540 B2 | 8/2008 | Edwards et al. |
| 7,497,847 B2 | 3/2009 | Crawford et al. |
| 7,694,828 B2 | 4/2010 | Swift et al. |
| 7,736,333 B2 | 6/2010 | Gillespie, III |
| D619,702 S | 7/2010 | Galbraith |
| D622,374 S | 8/2010 | Julian et al. |
| 7,771,397 B1 | 8/2010 | Olson |
| D628,690 S | 12/2010 | Galbraith |
| D629,509 S | 12/2010 | Julian et al. |
| 7,919,264 B2 | 4/2011 | Maksymowych et al. |
| D638,935 S | 5/2011 | Gilmore, III et al. |
| 7,938,802 B2 | 5/2011 | Bicknell et al. |
| 8,034,906 B2 | 10/2011 | Borhani et al. |
| D650,070 S | 12/2011 | Mori |
| 8,162,887 B2 | 4/2012 | Bicknell et al. |
| 8,216,583 B2 | 7/2012 | Kruase et al. |
| 8,372,030 B2 | 2/2013 | Dixon et al. |
| D677,380 S | 3/2013 | Julian et al. |
| D694,879 S | 12/2013 | Julian et al. |
| 8,668,670 B2 | 3/2014 | Bicknell et al. |
| 8,679,061 B2 | 3/2014 | Julian et al. |
| 2001/0025168 A1 | 9/2001 | Gross et al. |
| 2001/0053894 A1 | 12/2001 | Steenfeldt-Jensen et al. |
| 2002/0002344 A1 | 1/2002 | Douglas et al. |
| 2002/0016563 A1 | 2/2002 | Hill et al. |
| 2002/0042592 A1 | 4/2002 | Wilmot et al. |
| 2002/0095120 A1 | 7/2002 | Larsen et al. |
| 2002/0111587 A1 | 8/2002 | Hommann et al. |
| 2002/0161337 A1 | 10/2002 | Shaw et al. |
| 2002/0169408 A1 | 11/2002 | Beretta et al. |
| 2002/0183690 A1 | 12/2002 | Arnisolle |
| 2003/0004466 A1 | 1/2003 | Bitdinger et al. |
| 2003/0004467 A1 | 1/2003 | Musick et al. |
| 2003/0012786 A1 | 1/2003 | Teoh et al. |
| 2003/0023203 A1 | 1/2003 | Lavi et al. |
| 2003/0023205 A1 | 1/2003 | Botich et al. |
| 2003/0050606 A1 | 3/2003 | Brand et al. |
| 2003/0093036 A1 | 5/2003 | Crossman et al. |
| 2003/0105430 A1 | 6/2003 | Lavi et al. |
| 2003/0153868 A1 | 8/2003 | Azizi et al. |
| 2003/0187401 A1 | 10/2003 | Doyle |
| 2003/0212362 A1 | 11/2003 | Roser |
| 2003/0219438 A1 | 11/2003 | Salfeld et al. |
| 2003/0229308 A1 | 12/2003 | Tsals et al. |
| 2003/0235585 A1 | 12/2003 | Fischkoff et al. |
| 2003/0236502 A1 | 12/2003 | De La Serna et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0054327 A1 | 3/2004 | Gillespie |
| 2004/0147875 A1 | 7/2004 | Wallace et al. |
| 2004/0199117 A1 | 10/2004 | Giambattista et al. |
| 2004/0215151 A1 | 10/2004 | Marshall et al. |
| 2004/0225262 A1 | 11/2004 | Fathallah et al. |
| 2005/0020979 A1 | 1/2005 | Westbye et al. |
| 2005/0020984 A1 | 1/2005 | Lesch |
| 2005/0027255 A1 | 2/2005 | Lavi et al. |
| 2005/0049550 A1 | 3/2005 | Kirchhofer et al. |
| 2005/0049561 A1 | 3/2005 | Hommann et al. |
| 2005/0085776 A1 | 4/2005 | Hommann et al. |
| 2005/0096597 A1 | 5/2005 | Crawford et al. |
| 2005/0101919 A1 | 5/2005 | Brunnberg |
| 2005/0124940 A1 | 6/2005 | Martin et al. |
| 2005/0137196 A1 | 6/2005 | Timmer et al. |
| 2005/0137534 A1 | 6/2005 | Hommann |
| 2005/0137571 A1 | 6/2005 | Hommann |
| 2005/0165360 A1 | 7/2005 | Stamp |
| 2005/0165361 A1 | 7/2005 | Marshall et al. |
| 2005/0165362 A1 | 7/2005 | Slawson |
| 2005/0165363 A1 | 7/2005 | Judson et al. |
| 2005/0171476 A1 | 8/2005 | Judson et al. |
| 2005/0171477 A1 | 8/2005 | Rubin et al. |
| 2005/0209569 A1 | 9/2005 | Ishikawa et al. |

(56) References Cited

U.S. PATENT DOCUMENTS

| | | |
|---|---|---|
| 2005/0222539 A1 | 10/2005 | Gonzales et al. |
| 2005/0222540 A1 | 10/2005 | Kirchhofer et al. |
| 2005/0261634 A1 | 11/2005 | Karlsson |
| 2005/0273054 A1 | 12/2005 | Asch |
| 2005/0273055 A1 | 12/2005 | Harrison et al. |
| 2005/0273061 A1 | 12/2005 | Hommann et al. |
| 2005/0277885 A1 | 12/2005 | Scherer |
| 2005/0277886 A1 | 12/2005 | Hommann et al. |
| 2005/0277893 A1 | 12/2005 | Liversidge |
| 2005/0288633 A1 | 12/2005 | Jeffrey |
| 2006/0030819 A1 | 2/2006 | Young et al. |
| 2006/0036216 A1 | 2/2006 | Rimlinger et al. |
| 2006/0047250 A1 | 3/2006 | Hickingbotham et al. |
| 2006/0069350 A1 | 3/2006 | Buenger et al. |
| 2006/0069354 A1 | 3/2006 | Buenger et al. |
| 2006/0074519 A1 | 4/2006 | Barker et al. |
| 2006/0100588 A1 | 5/2006 | Brunnberg et al. |
| 2006/0111666 A1 | 5/2006 | Hommann et al. |
| 2006/0111674 A1 | 5/2006 | Vedrine |
| 2006/0129122 A1 | 6/2006 | Wyrick |
| 2006/0140907 A1 | 6/2006 | Blumberg et al. |
| 2006/0167413 A1 | 7/2006 | Marshall et al. |
| 2006/0189933 A1 | 8/2006 | Alheidt et al. |
| 2006/0253083 A1 | 11/2006 | Liu |
| 2007/0049865 A1 | 3/2007 | Radmer et al. |
| 2007/0129674 A1 | 6/2007 | Liversidge |
| 2007/0142776 A9 | 6/2007 | Kovelman et al. |
| 2007/0161960 A1 | 7/2007 | Chen et al. |
| 2007/0173772 A1 | 7/2007 | Liversidge |
| 2007/0197976 A1 | 8/2007 | Jacobs et al. |
| 2007/0239117 A1 | 10/2007 | Chelak et al. |
| 2008/0019969 A1 | 1/2008 | Gorman |
| 2008/0097337 A1 | 4/2008 | Judd et al. |
| 2008/0208125 A1 | 8/2008 | Bicknell et al. |
| 2008/0208140 A1 | 8/2008 | Barrelle |
| 2008/0269692 A1 | 10/2008 | James et al. |
| 2008/0281271 A1 | 11/2008 | Griffiths et al. |
| 2008/0300549 A1 | 12/2008 | Verespej et al. |
| 2009/0024076 A1 | 1/2009 | Babaev |
| 2009/0024093 A1 | 1/2009 | Carrel et al. |
| 2009/0036870 A1 | 2/2009 | Mounce et al. |
| 2009/0093792 A1 | 4/2009 | Gross et al. |
| 2009/0110679 A1 | 4/2009 | Li et al. |
| 2009/0148513 A1 | 6/2009 | Fraunhofer et al. |
| 2009/0157012 A1 | 6/2009 | Magne |
| 2009/0182284 A1 | 7/2009 | Morgan |
| 2009/0226530 A1 | 9/2009 | Lassner et al. |
| 2009/0240195 A1 | 9/2009 | Schrul et al. |
| 2009/0240210 A1 | 9/2009 | Walton et al. |
| 2009/0291062 A1 | 11/2009 | Fraunhofer et al. |
| 2009/0299328 A1 | 12/2009 | Mudd et al. |
| 2009/0304682 A1 | 12/2009 | Hoffman et al. |
| 2010/0021451 A1 | 1/2010 | Wong |
| 2010/0040630 A1 | 2/2010 | Elden et al. |
| 2010/0160869 A1 | 6/2010 | Liversidge |
| 2010/0160894 A1 | 6/2010 | Julian et al. |
| 2011/0054414 A1 | 3/2011 | Shang et al. |
| 2011/0178500 A1 | 7/2011 | Shang et al. |
| 2011/0218502 A1 | 9/2011 | Iio et al. |
| 2012/0014956 A1 | 1/2012 | Kupper et al. |
| 2012/0022499 A1 | 1/2012 | Anderson et al. |
| 2012/0107783 A1 | 5/2012 | Julian et al. |
| 2012/0197209 A1 | 8/2012 | Bicknell et al. |
| 2012/0233834 A1 | 9/2012 | Szechinski et al. |
| 2012/0238961 A1 | 9/2012 | Julian et al. |
| 2012/0289905 A1 | 11/2012 | Julian et al. |
| 2014/0276444 A1 | 9/2014 | Bicknell et al. |

FOREIGN PATENT DOCUMENTS

| | | |
|---|---|---|
| DE | 2019296 A1 | 11/1971 |
| DE | 19821933 C1 | 11/1999 |
| DE | 60207576 T2 | 6/2006 |
| EP | 0068864 A2 | 1/1983 |
| EP | 0125023 A1 | 11/1984 |
| EP | 0154316 A2 | 9/1985 |
| EP | 0171496 A2 | 2/1986 |
| EP | 0173494 A2 | 3/1986 |
| EP | 0184187 A2 | 6/1986 |
| EP | 0260610 A2 | 3/1988 |
| EP | 0401384 A1 | 12/1990 |
| EP | 1334740 A1 | 8/2003 |
| EP | 1364667 A2 | 11/2003 |
| EP | 1523360 A1 | 4/2005 |
| EP | 1257321 B1 | 7/2008 |
| EP | 2067496 A1 | 6/2009 |
| EP | 2085104 A1 | 8/2009 |
| GB | 2243552 A | 11/1991 |
| GB | 2388033 A | 11/2003 |
| GB | 2465389 A | 5/2010 |
| JP | S62502876 A | 11/1987 |
| JP | 2001-512038 A | 8/2001 |
| JP | 2004516074 A | 6/2004 |
| JP | 2006-507060 A | 3/2006 |
| JP | 5014835 B2 | 8/2012 |
| JP | 5161712 B2 | 3/2013 |
| RU | 2004256 C1 | 12/1993 |
| RU | 2069584 C1 | 11/1996 |
| RU | 2131748 C1 | 6/1999 |
| RU | 2169584 C1 | 6/2001 |
| RU | 2196611 C2 | 1/2003 |
| WO | WO-90/01047 A1 | 2/1990 |
| WO | WO-90/07861 A1 | 7/1990 |
| WO | WO-91/03553 A1 | 3/1991 |
| WO | WO-91/16094 A1 | 10/1991 |
| WO | WO-91/17271 A1 | 11/1991 |
| WO | WO-92/01047 A1 | 1/1992 |
| WO | WO-92/09690 A2 | 6/1992 |
| WO | WO-92/15679 A1 | 9/1992 |
| WO | WO-92/18619 A1 | 10/1992 |
| WO | WO-92/20791 A1 | 11/1992 |
| WO | WO-93/01288 A1 | 1/1993 |
| WO | WO-93/06213 A1 | 4/1993 |
| WO | WO-93/13819 A1 | 7/1993 |
| WO | WO-93/19751 A1 | 10/1993 |
| WO | WO-94/06476 A1 | 3/1994 |
| WO | WO-9408609 A1 | 4/1994 |
| WO | WO-9409839 A1 | 5/1994 |
| WO | WO-9413342 A1 | 6/1994 |
| WO | WO-9426333 A1 | 11/1994 |
| WO | WO-9729131 A1 | 8/1997 |
| WO | WO-9922789 A1 | 5/1999 |
| WO | WO-9922792 A1 | 5/1999 |
| WO | WO-0137908 A1 | 5/2001 |
| WO | WO-0162319 A2 | 8/2001 |
| WO | WO-02072636 A2 | 9/2002 |
| WO | WO-03039633 A2 | 5/2003 |
| WO | WO-03077968 A2 | 9/2003 |
| WO | WO-03097133 A1 | 11/2003 |
| WO | WO-03099358 A2 | 12/2003 |
| WO | WO-2004000397 A1 | 12/2003 |
| WO | WO-2004016286 A2 | 2/2004 |
| WO | WO-0212502 A9 | 3/2004 |
| WO | WO-2004024211 A2 | 3/2004 |
| WO | WO-2004041330 A2 | 5/2004 |
| WO | WO-2004047892 A1 | 6/2004 |
| WO | WO-2004060451 A1 | 7/2004 |
| WO | WO-2004067068 A1 | 8/2004 |
| WO | WO-2005000206 A2 | 1/2005 |
| WO | WO-2005002653 A1 | 1/2005 |
| WO | WO-2005046765 A2 | 5/2005 |
| WO | WO-2005079889 A1 | 9/2005 |
| WO | WO-2005090836 A1 | 9/2005 |
| WO | WO-2005113039 A1 | 12/2005 |
| WO | WO-2005115508 A1 | 12/2005 |
| WO | WO-2005115509 A1 | 12/2005 |
| WO | WO-2005115510 A1 | 12/2005 |
| WO | WO-2005115511 A1 | 12/2005 |
| WO | WO-2005115512 A1 | 12/2005 |
| WO | WO-2005115513 A1 | 12/2005 |
| WO | WO-2005115516 A1 | 12/2005 |
| WO | WO-2006000785 A1 | 1/2006 |
| WO | WO-2006058061 A1 | 6/2006 |
| WO | WO-2008/005315 A2 | 1/2008 |

(56) References Cited

FOREIGN PATENT DOCUMENTS

| WO | 2008089886 A1 | 7/2008 |
|---|---|---|
| WO | WO-2009/040603 A1 | 4/2009 |
| WO | WO-2009140251 A2 | 11/2009 |
| WO | WO-2009/155277 A1 | 12/2009 |
| WO | WO-2010/029054 A1 | 3/2010 |
| WO | WO-201056712 A1 | 5/2010 |
| WO | WO-2010/127146 A1 | 11/2010 |
| WO | WO-2011/075524 A1 | 6/2011 |
| WO | WO-2011/133823 A1 | 10/2011 |
| WO | WO-2012/129174 A1 | 9/2012 |
| WO | WO-2012/135524 A1 | 10/2012 |

OTHER PUBLICATIONS

Examination Report issued in Australian Application No. 2010242972, dated May 13, 2014.
Examination Report issued in Australian Application No. 2013204406, dated May 13, 2014.
Extended European Search Report issued in European Application No. 10770353.0, dated Dec. 12, 2014.
International Preliminary Report on Patentability issued in PCT/US2010/060496, mailed Jun. 19, 2012.
International Search Report and Written Opinion issued in International Application No. PCT/US2012/022432, dated Apr. 18, 2012.
International Search Report and Written Opinion issued in International Application No. PCT/US2012/029682, dated Jul. 27, 2012.
International Search Report issued in International Application No. PCT/US2012/022433, dated Jul. 5, 2012.
Office Action issued in Japanese Application No. 2012-508741, mailed Feb. 4, 2014.
Summons to Attend Oral Proceedings pursuant to Rule 115(1) EPC, dated Apr. 20, 2012.
Written Opinion issued in PCT/US2012/029682, mailed Jul. 27, 2012.
"Abbott Receives FDA Approval for New Humira Delivery Device," Press Release, dated Jun. 26, 2006 (color).
Communication of a Notice of Opposition issued in European Application No. 04822031.3-1526, dated Jan. 6, 2010.
Communication pursuant to Article 94(3) EPC issued by the European Patent Office in European Application No. 05758156.3-2320, dated Jan. 18, 2011.
Communication pursuant to Article 96(2) EPC issued in European Application No. 04822031.3-1526, dated May 31, 2007.
Communication under Rule 112 EPC issued in European Application No. 04822031.3, dated Mar. 13, 2007.
Correspondence from Dept. of Health & Human Services, Food and Drug Administration, to Robert Shaw/Owen Mumford, Inc. regarding Section 501(k) notification to market device, dated Mar. 6, 2000.
Decision on Grant issued in Russian Application No. 2006145501/14(049694), dated Nov. 2, 2009.
Decision on Grant issued in Russian Application No. 2009102986/14(003862), dated Jun. 30, 2011.
Examination Report issued in Australian Application No. 2007269791, dated Jul. 30, 2012.
Examination Report issued in Australian Application No. 2010331936, dated Nov. 12, 2012.
Examination Report issued in New Zealand Application No. 552340, dated Apr. 27, 2009.
Examination Report issued in New Zealand Application No. 552340, dated Aug. 12, 2010.
Examination Report issued in New Zealand Application No. 595605, dated Apr. 12, 2013.
Examination Report issued in New Zealand Application No. 600069, dated Mar. 28, 2013.
First Office Action issued by the Chinese Patent Office on Chinese Patent Application No. 200580020958.6, dated Sep. 5, 2008.
Inquiry issued by the Russia Federal Intellectual Property Institute on Russian Patent Application No. 2006145501/14(049694), dated May 21, 2009.
International Preliminary Report on Patentability issued in International Application No. PCT/GB2005/002487, dated Sep. 7, 2006.
International Preliminary Report on Patentability issued in International Application No. PCT/US2004/013278, dated Nov. 1, 2006.
International Preliminary Report on Patentability issued in International Application No. PCT/US2007/015095, dated Jun. 19, 2009.
International Preliminary Report on Patentability issued in International Application No. PCT/US2010/033012, dated Nov. 1, 2011.
International Search Report issued in International Application No. PCT/GB2005/002487, dated Aug. 19, 2005.
International Search Report issued in International Application No. PCT/US2004/013278, dated May 30, 2005.
International Search Report issued in International Application No. PCT/US2007/015095, dated Sep. 11, 2008.
International Search Report issued in International Application No. PCT/US2010/033012, dated Jul. 2, 2010.
International Search Report issued in International Application No. PCT/US2010/060496, dated Feb. 16, 2011.
International Search Report issued in International Application No. PCT/US2011/033504, dated Jul. 8, 2011.
Notice of Reasons for Rejection issued in Japanese Application No. 2007-517459, dated Aug. 24, 2010.
Notice of Reasons for Rejection issued in Japanese Application No. 2007-517459, dated Mar. 8, 2011.
Notice of Rejection issued in Japanese Application No. 2009-518284, dated May 29, 2012.
Notice of Rejection issued in Japanese Application No. 2011-196424, dated Jan. 29, 2013.
Notification of Provisional Rejection issued in Korean Application No. 10-2006-7026814, dated Jul. 19, 2011.
Notification of Reexamination issued in Chinese Application No. 200580020958.6, dated Aug. 17, 2010.
Nov. 10, 1999 correspondence from Dept. of Health & Human Services, Food and Drug Administration to Robert Shaw/Owen Mumford regarding Section 501 (k) notification intent to market device.
Office Action issued in Australian Application No. 2005256832, dated Apr. 18, 2011.
Office Action issued in Australian Application No. 2005256832, dated Feb. 22, 2010.
Office Action issued in Canadian Application No. 2,571,571, dated Oct. 24, 2011.
Office Action issued in Chinese Application No. 200580020958.6, dated Sep. 5, 2008.
Office Action issued in Chinese Application No. 201080029621.2, dated Feb. 27, 2013.
Office Action issued in Mexican Application No. PA/a/2006/015056, dated Apr. 1, 2011.
Office Action issued in Mexican Application No. PA/a/2006/015056, dated Jul. 28, 2010.
Office Action issued in Russian Application No. 2006145501/14(049694), dated May 21, 2009.
Owen Mumford drawing of the Plunger-Miniject dated Sep. 5, 1997, Drawing No. AJ 654.
Owen Mumford drawing/schematic of the Abbott-Plunger AUTOject Mini, dated Mar. 25, 2002, Drawing No. P02 207.
Owen Mumford drawing/schematic of the Plunger—Autoject Mini dated May 9, 1997, Drawing No. AJ 654.
Owen Mumford drawing/schematic of the Plunger-Miniject dated Mar. 30, 1993, Drawing No. AJ 358.
Owen Mumford drawing/schematic of the Plunger-Miniject dated Mar. 30, 1993, Drawing No. P93.022.
Reexamination Decision issued in Chinese Application No. 200580020958.6, dated Jun. 13, 2011.
Rejection Decision issued in Chinese Application No. 200580020958.6, dated Jun. 5, 2009.
Written Opinion issued in International Application No. PCT/GB2005/002487, dated Dec. 23, 2006.
Written Opinion issued in International Application No. PCT/US2004/013278, dated Oct. 29, 2006.
Written Opinion issued in International Application No. PCT/US2007/015095, dated Sep. 11, 2008.

(56) References Cited

OTHER PUBLICATIONS

Written Opinion issued in International Application No. PCT/US2010/033012, dated Jul. 2, 2010.
Written Opinion issued in International Application No. PCT/US2010/060496, dated Feb. 16, 2011.
Written Opinion issued in International Application No. PCT/US2011/033504, dated Jul. 8, 2011.
Written Opinion issued in International Application No. PCT/US2012/022433, dated Jul. 5, 2012.
Notice of Acceptance issued in Australian Application No. 2013204406, dated Jun. 26, 2015.
Notice of Acceptance issued in Australian Application No. 2010242972, dated Jun. 26, 2015.
Office Action issued in Taiwan Application No. 099113810, dated Nov. 19, 2015. English translation only.
Office Action issued in Japanese Patent Application No. 2014-261814, mailed Dec. 8, 2015. English translation only.
Office Action issued in Canadian Patent Application No. 2760237, dated Apr. 26, 2016.

\* cited by examiner

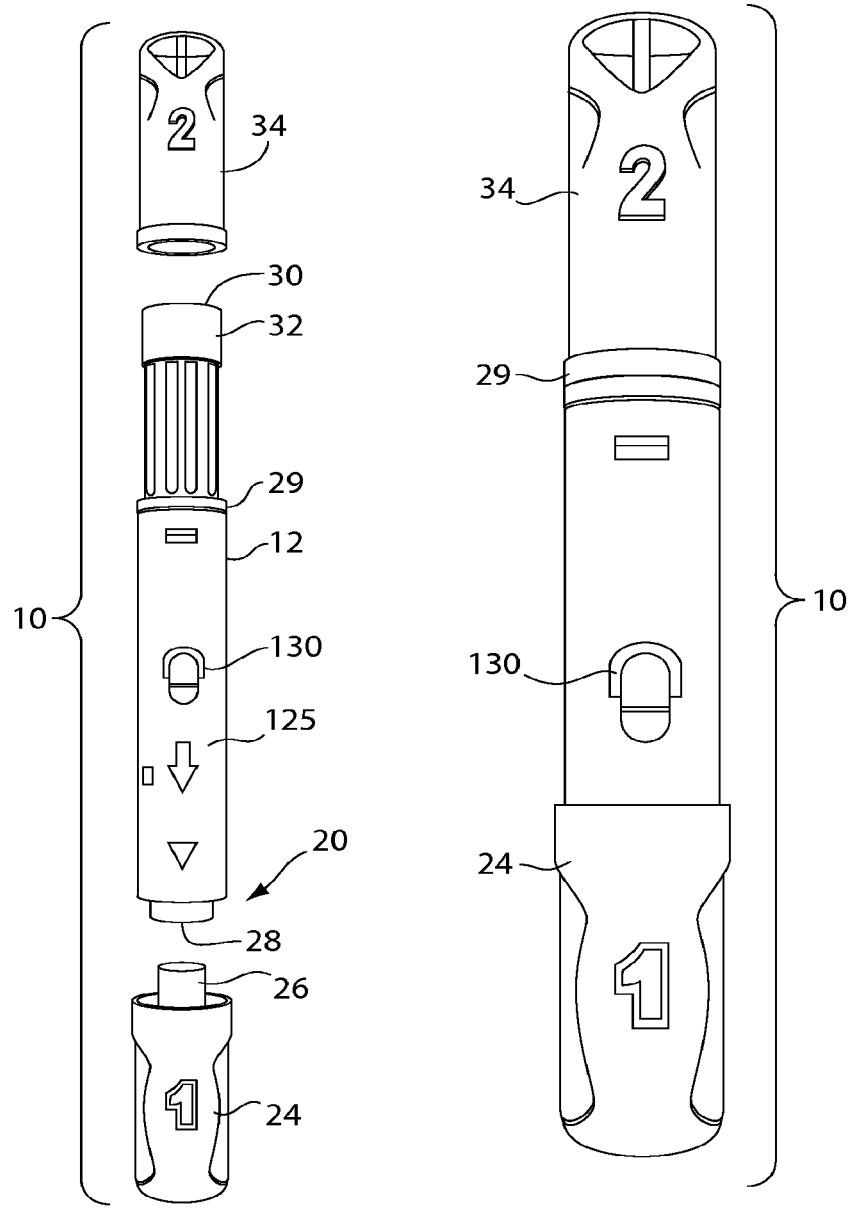

CONTROL (ICS = 38°)

ICS = 48° (TOP POINT FIXED)

```
                           SEQUENCE LISTING

<160> NUMBER OF SEQ ID NOS: 37

<210> SEQ ID NO 1
  <211> LENGTH: 107
  <212> TYPE: PRT
  <213> ORGANISM: Artificial
  <220> FEATURE:
  <223> OTHER INFORMATION: D2E7 light chain variable region

<400> SEQUENCE: 1

Asp Ile Gln Met Thr Gln Ser Pro Ser Ser Leu Ser Ala Ser Val Gly
  1               5                   10                  15

Asp Arg Val Thr Ile Thr Cys Arg Ala Ser Gln Gly Ile Arg Asn Tyr
                  20                  25                  30

Leu Ala Trp Tyr Gln Gln Lys Pro Gly Lys Ala Pro Lys Leu Leu Ile
              35                  40                  45

Tyr Ala Ala Ser Thr Leu Gln Ser Gly Val Pro Ser Arg Phe Ser Gly
      50                  55                  60

Ser Gly Ser Gly Thr Asp Phe Thr Leu Thr Ile Ser Ser Leu Gln Pro
  65                  70                  75                  80

Glu Asp Val Ala Thr Tyr Tyr Cys Gln Arg Tyr Asn Arg Ala Pro Tyr
                  85                  90                  95

Thr Phe Gly Gln Gly Thr Lys Val Glu Ile Lys
              100                 105

<210> SEQ ID NO 2
  <211> LENGTH: 121
  <212> TYPE: PRT
  <213> ORGANISM: Artificial
  <220> FEATURE:
  <223> OTHER INFORMATION: D2E7 heavy chain variable region

<400> SEQUENCE: 2

Glu Val Gln Leu Val Glu Ser Gly Gly Gly Leu Val Gln Pro Gly Arg
  1               5                   10                  15

Ser Leu Arg Leu Ser Cys Ala Ala Ser Gly Phe Thr Phe Asp Asp Tyr
                  20                  25                  30

Ala Met His Trp Val Arg Gln Ala Pro Gly Lys Gly Leu Glu Trp Val
              35                  40                  45

Ser Ala Ile Thr Trp Asn Ser Gly His Ile Asp Tyr Ala Asp Ser Val
      50                  55                  60

Glu Gly Arg Phe Thr Ile Ser Arg Asp Asn Ala Lys Asn Ser Leu Tyr
  65                  70                  75                  80

Leu Gln Met Asn Ser Leu Arg Ala Glu Asp Thr Ala Val Tyr Tyr Cys
                  85                  90                  95

Ala Lys Val Ser Tyr Leu Ser Thr Ala Ser Ser Leu Asp Tyr Trp Gly
              100                 105                 110

Gln Gly Thr Leu Val Thr Val Ser Ser
              115                 120

<210> SEQ ID NO 3
```

```
<211> LENGTH: 9
<212> TYPE: PRT
<213> ORGANISM: Artificial
<220> FEATURE:
<223> OTHER INFORMATION: D2E7 light chain variable region CDR3
<221> NAME/KEY: VARIANT
<222> LOCATION: 9
<223> OTHER INFORMATION: Xaa = Any Amino Acid

<400> SEQUENCE: 3

Gln Arg Tyr Asn Arg Ala Pro Tyr Xaa
  1               5

<210> SEQ ID NO 4
<211> LENGTH: 12
<212> TYPE: PRT
<213> ORGANISM: Artificial
<220> FEATURE:
<223> OTHER INFORMATION: D2E7 heavy chain variable region CDR3
<221> NAME/KEY: VARIANT
<222> LOCATION: 12
<223> OTHER INFORMATION: Xaa = Any Amino Acid

<400> SEQUENCE: 4

Val Ser Tyr Leu Ser Thr Ala Ser Ser Leu Asp Xaa
  1               5                  10

<210> SEQ ID NO 5
<211> LENGTH: 7
<212> TYPE: PRT
<213> ORGANISM: Artificial
<220> FEATURE:
<223> OTHER INFORMATION: D2E7 light chain variable region CDR2

<400> SEQUENCE: 5

Ala Ala Ser Thr Leu Gln Ser
  1               5

<210> SEQ ID NO 6
<211> LENGTH: 17
<212> TYPE: PRT
<213> ORGANISM: Artificial
<220> FEATURE:
<223> OTHER INFORMATION: D2E7 heavy chain variable region CDR2

<400> SEQUENCE: 6

Ala Ile Thr Trp Asn Ser Gly His Ile Asp Tyr Ala Asp Ser Val Glu
  1               5                  10                  15

Gly

<210> SEQ ID NO 7
<211> LENGTH: 11
<212> TYPE: PRT
<213> ORGANISM: Artificial
<220> FEATURE:
<223> OTHER INFORMATION: D2E7 light chain variable region CDR1

<400> SEQUENCE: 7

Arg Ala Ser Gln Gly Ile Arg Asn Tyr Leu Ala
  1               5                  10

<210> SEQ ID NO 8
<211> LENGTH: 5
<212> TYPE: PRT
<213> ORGANISM: Artificial
<220> FEATURE:
<223> OTHER INFORMATION: D2E7 heavy chain variable region CDR1
```

-continued

```
<400> SEQUENCE: 8

Asp Tyr Ala Met His
1               5

<210> SEQ ID NO 9
<211> LENGTH: 107
<212> TYPE: PRT
<213> ORGANISM: Artificial
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
<211> LENGTH: 121
<212> TYPE: PRT
<213> ORGANISM: Artificial
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
    50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial
<220> FEATURE:
<223> OTHER INFORMATION: 2SD4 light chain variable region CDR3

<400> SEQUENCE: 11
```

Gln Lys Tyr Asn Ser Ala Pro Tyr Ala
1               5

<210> SEQ ID NO 12
<211> LENGTH: 9
<212> TYPE: PRT
<213> ORGANISM: Artificial
<220> FEATURE:
<223> OTHER INFORMATION: EP B12 light chain variable region CDR3

<400> SEQUENCE: 12

Gln Lys Tyr Asn Arg Ala Pro Tyr Ala
1               5

<210> SEQ ID NO 13
<211> LENGTH: 9
<212> TYPE: PRT
<213> ORGANISM: Artificial
<220> FEATURE:
<223> OTHER INFORMATION: VL10E4 light chain variable region CDR3

<400> SEQUENCE: 13

Gln Lys Tyr Gln Arg Ala Pro Tyr Thr
1               5

<210> SEQ ID NO 14
<211> LENGTH: 9
<212> TYPE: PRT
<213> ORGANISM: Artificial
<220> FEATURE:
<223> OTHER INFORMATION: VL100A9 light chain variable region CDR3

<400> SEQUENCE: 14

Gln Lys Tyr Ser Ser Ala Pro Tyr Thr
1               5

<210> SEQ ID NO 15
<211> LENGTH: 9
<212> TYPE: PRT
<213> ORGANISM: Artificial
<220> FEATURE:
<223> OTHER INFORMATION: VLL100D2 light chain variable region CDR3

<400> SEQUENCE: 15

Gln Lys Tyr Asn Ser Ala Pro Tyr Thr
1               5

<210> SEQ ID NO 16
<211> LENGTH: 9
<212> TYPE: PRT
<213> ORGANISM: Artificial
<220> FEATURE:
<223> OTHER INFORMATION: VLL0F4 light chain variable region CDR3

<400> SEQUENCE: 16

Gln Lys Tyr Asn Arg Ala Pro Tyr Thr
1               5

<210> SEQ ID NO 17
<211> LENGTH: 9
<212> TYPE: PRT
<213> ORGANISM: Artificial
<220> FEATURE:
<223> OTHER INFORMATION: L0E5 light chain variable region CDR3

<400> SEQUENCE: 17

Gln Lys Tyr Asn Ser Ala Pro Tyr Tyr
1               5

<210> SEQ ID NO 18
<211> LENGTH: 9
<212> TYPE: PRT
<213> ORGANISM: Artificial
<220> FEATURE:
<223> OTHER INFORMATION: VLLOG7 light chain variable region CDR3

<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial
<220> FEATURE:
<223> OTHER INFORMATION: VLLOG9 light chain variable region CDR3

<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial
<220> FEATURE:
<223> OTHER INFORMATION: VLLOH1 light chain variable region CDR3

<400> SEQUENCE: 20

Gln Lys Tyr Asn Arg Ala Pro Tyr Asn
1               5

<210> SEQ ID NO 21
<211> LENGTH: 9
<212> TYPE: PRT
<213> ORGANISM: Artificial
<220> FEATURE:
<223> OTHER INFORMATION: VLLOH10 light chain variable region CDR3

<400> SEQUENCE: 21

Gln Lys Tyr Asn Ser Ala Ala Tyr Ser
1               5

<210> SEQ ID NO 22
<211> LENGTH: 9
<212> TYPE: PRT
<213> ORGANISM: Artificial
<220> FEATURE:
<223> OTHER INFORMATION: VL1B7 light chain variable region CDR3

<400> SEQUENCE: 22

Gln Gln Tyr Asn Ser Ala Pro Asp Thr
1               5

<210> SEQ ID NO 23
<211> LENGTH: 9
<212> TYPE: PRT
<213> ORGANISM: Artificial
<220> FEATURE:
<223> OTHER INFORMATION: VL1C1 light chain variable region CDR3

<400> SEQUENCE: 23

Gln Lys Tyr Asn Ser Asp Pro Tyr Thr

<210> SEQ ID NO 24
<211> LENGTH: 9
<212> TYPE: PRT
<213> ORGANISM: Artificial
<220> FEATURE:
<223> OTHER INFORMATION: VL0.1F4 light chain variable region CDR3

<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial
<220> FEATURE:
<223> OTHER INFORMATION: VL0.1H8 light chain variable region CDR3

<400> SEQUENCE: 25

Gln Lys Tyr Asn Arg Pro Pro Tyr Thr
1               5

<210> SEQ ID NO 26
<211> LENGTH: 9
<212> TYPE: PRT
<213> ORGANISM: Artificial
<220> FEATURE:
<223> OTHER INFORMATION: L0E7.A light chain variable region CDR3

<400> SEQUENCE: 26

Gln Arg Tyr Asn Arg Ala Pro Tyr Ala
1               5

<210> SEQ ID NO 27
<211> LENGTH: 12
<212> TYPE: PRT
<213> ORGANISM: Artificial
<220> FEATURE:
<223> OTHER INFORMATION: 2SD4 heavy chain variable region CDR3

<400> SEQUENCE: 27

Ala Ser Tyr Leu Ser Thr Ser Ser Ser Leu Asp Asn
1               5                   10

<210> SEQ ID NO 28
<211> LENGTH: 12
<212> TYPE: PRT
<213> ORGANISM: Artificial
<220> FEATURE:
<223> OTHER INFORMATION: VH1B11 heavy chain variable region CDR3

<400> SEQUENCE: 28

Ala Ser Tyr Leu Ser Thr Ser Ser Ser Leu Asp Lys
1               5                   10

<210> SEQ ID NO 29
<211> LENGTH: 12
<212> TYPE: PRT
<213> ORGANISM: Artificial
<220> FEATURE:
<223> OTHER INFORMATION: VH1D8 heavy chain variable region CDR3

<400> SEQUENCE: 29

Ala Ser Tyr Leu Ser Thr Ser Ser Ser Leu Asp Tyr
1               5                   10

<210> SEQ ID NO 30
<211> LENGTH: 12
<212> TYPE: PRT
<213> ORGANISM: Artificial
<220> FEATURE:
<223> OTHER INFORMATION: VH1A11 heavy chain variable region CDR3

<400> SEQUENCE: 30

Ala Ser Tyr Leu Ser Thr Ser Ser Ser Leu Asp Asp
1               5                   10

<210> SEQ ID NO 31
<211> LENGTH: 12
<212> TYPE: PRT
<213> ORGANISM: Artificial
<220> FEATURE:
<223> OTHER INFORMATION: VH1B12 heavy chain variable region CDR3

<400> SEQUENCE: 31

Ala Ser Tyr Leu Ser Thr Ser Phe Ser Leu Asp Tyr
1               5                   10

<210> SEQ ID NO 32
<211> LENGTH: 12
<212> TYPE: PRT
<213> ORGANISM: Artificial
<220> FEATURE:
<223> OTHER INFORMATION: VH1E4 heavy chain variable region CDR3

<400> SEQUENCE: 32

Ala Ser Tyr Leu Ser Thr Ser Ser Ser Leu His Tyr
1               5                   10

<210> SEQ ID NO 33
<211> LENGTH: 12
<212> TYPE: PRT
<213> ORGANISM: Artificial
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
1               5                   10

<210> SEQ ID NO 35
<211> LENGTH: 12
<212> TYPE: PRT
<213> ORGANISM: Artificial
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
1               5                   10

```
<210> SEQ ID NO 36
<211> LENGTH: 321
<212> TYPE: DNA
<213> ORGANISM: Artificial
<220> FEATURE:
<223> OTHER INFORMATION: D2E7 light chain variable region

<400> SEQUENCE: 36
gacatccaga tgacccagtc tccatcctcc ctgtctgcat ctgtagggga cagagtcacc      60
atcacttgtc gggcaagtca gggcatcaga aattacttag cctggtatca gcaaaaacca    120
gggaaagccc ctaagctcct gatctatgct gcatccactt tgcaatcagg ggtcccatct    180
cggttcagtg gcagtggatc tgggacagat ttcactctca ccatcagcag cctacagcct    240
gaagatgttg caacttatta ctgtcaaagg tataaccgtg caccgtatac ttttggccag    300
gggaccaagg tggaaatcaa a                                              321

<210> SEQ ID NO 37
<211> LENGTH: 363
<212> TYPE: DNA
<213> ORGANISM: Artificial
<220> FEATURE:
<223> OTHER INFORMATION: D2E7 heavy chain variable region

<400> SEQUENCE: 37
gaggtgcagc tggtggagtc tgggggaggc ttggtacagc ccggcaggtc cctgagactc      60
tcctgtgcgg cctctggatt caccttttgat gattatgcca tgcactgggt ccggcaagct    120
ccagggaagg gcctggaatg ggtctcagct atcacttgga atagtggtca catagactat    180
gcggactctg tggagggccg attcaccatc tccagagaca acgccaagaa ctccctgtat    240
ctgcaaatga acagtctgag agctgaggat acggccgtat attactgtgc gaaagtctcg    300
taccttagca ccgcgtcctc ccttgactat tggggccaag gtaccctggt caccgtctcg    360
agt                                                                  363
```

AUTOMATIC INJECTION DEVICE

CROSS-REFERENCE TO RELATED APPLICATIONS

This application is related to and is a continuation of U.S. patent Ser. No. 12/770,557, filed Apr. 29, 2010 and which claims priority to U.S. Provisional Application Ser. No. 61/173,952, filed Apr. 29, 2009, and U.S. Provisional Application Ser. No. 61/286,766, filed Dec. 15, 2009, the entire contents of each application are incorporated herein by reference in their entirety for any purpose.

SEQUENCE LISTING

The instant application contains a Sequence Listing which has been submitted electronically in the parent U.S. patent application ser. No. 12/770,557 and is included below.

TECHNICAL FIELD

Exemplary embodiments relate to improved automatic injection devices for injecting a substance, such as a drug, into a patient's body.

BACKGROUND

Automatic injection devices offer an alternative to manually-operated syringes for delivering substances into patients' bodies and allow patients to self-administer injections. Automatic injection devices have been used to deliver medications under emergency conditions, for example, to administer epinephrine to counteract the effects of a severe allergic reaction. Automatic injection devices have also been described for use in administering anti-arrhythmic medications and selective thrombolytic agents during a heart attack (see e.g., U.S. Pat. Nos. 3,910,260; 4,004,577; 4,689,042; 4,755,169 and 4,795,433). Various types of automatic injection devices are also described in, for example, U.S. Pat. Nos. 3,941,130; 4,261,358; 5,085,642; 5,092,843; 5,102,393; 5,267,963; 6,149,626; 6,270,479; and 6,371,939 and U.S. Patent Publication No. WO/2008/005315.

Conventionally, an automatic injection device, when operated, causes a syringe in the device to move forwardly and a needle to project from a housing so that a substance contained in the syringe is ejected into a patient's body. In some cases, movement of the syringe toward the patient's skin such that the needle is inserted into the skin before pressurizing a substance inside the syringe helps prevent the substance from dripping out of the needle before the injection occurs.

Conventional automatic injection devices can occasionally fail due to suboptimal minimum forces (FtFs) required to actuate their firing mechanisms. Conventional devices can misfire even when their firing mechanisms are not engaged with a substantial amount of force, or fail to fire even when their firing mechanisms are engaged with a substantial amount of force. For example, in a conventional device with a lower than optimal FtF, an inadvertent tap on the firing mechanism may engage the firing mechanism and cause the device to misfire and expel the substance contained in the device. This may lead to wastage or misdelivery of the substance before the patient has attached the automatic injection device to his/her body for an injection. Conversely, in a conventional device with a higher than optimal FtF, even a moderate or large force applied by a patient on the firing mechanism may fail to engage the firing mechanism and may fail to expel the substance contained in the device. This may require patients to apply excessive amounts of force to the firing mechanism to expel the substance, which may be uncomfortable to many patients and even intolerably uncomfortable to particularly frail patients. Such variability in the FtF required to actuate the firing mechanism is not desirable in automatic injection devices.

SUMMARY

Exemplary embodiments provide automatic injection devices, having a firing mechanism assembly with one or more plungers configured to improve the force to fire (FtF). "Force to fire" (or "FtF") refers to the minimum force that must be delivered to the firing mechanism assembly of an automatic injection device in order to initiate the movement of the plunger. The improved FtF minimizes unintentional activation or initiation, i.e., misfiring of the firing mechanism assembly, and allows patients to comfortably actuate the automatic injection device.

Exemplary embodiments provide a syringe plunger formed of a polymeric material. The syringe plunger includes a pressurizer disposed at a proximal end, and a distal end bifurcated into a first plunger arm having a first conical surface and a second conical surface, and a second plunger arm having a first conical surface and a second conical surface. The distal end includes a first contact surface defined by the first conical surface of the first plunger arm and the first conical surface of the second plunger arm, the first contact surface configured to initially contact a firing engagement mechanism, the first contact surface disposed at a first angle of between about 40° and about 80° relative to a longitudinal axis of the syringe plunger. The distal end also includes a second contact surface defined by the second conical surface of the first plunger arm and the second conical surface of the second plunger arm, the second contact surface configured to contact the firing engagement mechanism subsequent to contact by the first contact surface.

Exemplary embodiments provide an automatic injection device including a syringe including a syringe barrel for holding a substance and a syringe plunger formed of a polymeric material. The syringe plunger includes a pressurizer disposed at a proximal end, and a distal end bifurcated into a first plunger arm having a first conical surface and a second conical surface, and a second plunger arm having a first conical surface and a second conical surface. The distal end includes a first contact surface defined by the first conical surface of the first plunger arm and the first conical surface of the second plunger arm, the first contact surface configured to initially contact a firing engagement mechanism, the first contact surface disposed at a first angle of between about 40° and about 80° relative to a longitudinal axis of the syringe plunger. The distal end also includes a second contact surface defined by the second conical surface of the first plunger arm and the second conical surface of the second plunger arm, the second contact surface configured to contact the firing engagement mechanism subsequent to contact by the first contact surface.

Exemplary embodiments provide firing mechanism assemblies for automatic injection devices, each having one or more plungers configured to improve the FtF of the firing mechanism assembly. In an exemplary embodiment, the firing mechanism assemblies have an improved FtF for actuation.

Exemplary embodiments provide methods for using automatic injection devices, each having a firing mechanism assembly with one or more plungers configured to improve the FtF of the firing mechanism assembly. Exemplary embodiments also provide methods for using firing mechanism assemblies for automatic injection devices, each having one or more plungers configured to improve the FtF of the firing mechanism assembly.

Exemplary embodiments provide methods of configuring the plungers of automatic injection devices to improve the FtF of the firing mechanism. Exemplary methods include identifying, testing and configuring factors related to the automatic injection devices that affect the FtF of the firing mechanism. These factors may include, but are not limited to, characteristics of a plunger of the firing mechanism, e.g., one or more molding conditions under which the plunger is molded (e.g., mold temperature, cooling time), the initial contact surface (ICS) angle of the plunger, the ICS length of the plunger, the plunger base bridge angle, the width between the plunger arms, the flex modulus of the plunger material, or any combination thereof. Each of these factors will be described in more detail in the following sections.

Exemplary embodiments provide a firing mechanism assembly for use in an automatic injection device, the firing mechanism assembly including a plunger having two plunger arms separated by a plunger arm width, a firing button, and a firing body. Activation of the firing button causes the plunger arm width to decrease such that the firing button engages the firing body, thereby firing the automatic injection device. The firing mechanism assembly is configured so that the FtF required to actuate the firing mechanism assembly is between about 5 Newtons (N) and about 45 N. In an exemplary embodiment, the FtF is between about 10 N and about 29 N. In another exemplary embodiment, the FtF is between about 5 N and about 25 N. In yet another exemplary embodiment, the FtF is between about 15 N and about 30 N, including all values intermediary thereto.

In an exemplary embodiment, the plunger arms include an ICS that has an ICS length and that forms an ICS angle relative to the longitudinal axis of the plunger. In an exemplary embodiment, the plunger arms also include a secondary contact surface (SCS) that has an SCS length and that forms an SCS angle relative to the longitudinal axis of the plunger.

In an exemplary embodiment, the ICS angle is between about 40° and about 80°. In another exemplary embodiment, the ICS angle is between about 40° and about 50°. In another embodiment, the ICS angle is about 48°.

In an embodiment, the ICS length is between about 2.44 mm and about 3.03 mm. In another embodiment, the ICS length is between about 2.64 mm and about 3.03 mm. In another embodiment, the ICS length is between about 2.84 mm and about 3.03 mm. In another embodiment, the ICS length is about 3.00 mm.

In an embodiment, the plunger arm width is between about 2.55 mm and about 5.15 mm. In another embodiment, the plunger arm width is between about 2.55 mm and about 4.25 mm. In another embodiment, the plunger arm width is about 3.05 mm. In one embodiment, the plunger arm width length is greater than about 3.00 mm.

In an embodiment, the SCS angle is between about 6° and about 38°. In another embodiment, the SCS angle is between about 8° and about 25°. In another embodiment, the SCS angle is about 23°. In yet another embodiment, the SCS angle is about 9°.

In an embodiment, the SCS length is between about 0.01 mm and about 0.59 mm. In another embodiment, the SCS length is about 0.40 mm.

In an embodiment, the plunger base bridge angle is between about 0° and about 2.0°.

In an exemplary embodiment, the plunger is composed of a material having a flex modulus between about 1000 MPa and about 6000 MPa. In another exemplary embodiment, the plunger is composed of a material having a flex modulus of between about 2,000 MPa and about 5,500 MPa. In yet another exemplary embodiment, the plunger is composed of a material having a flex modulus of between about 3000 MPa and about 5000 MPa. In still another exemplary embodiment, the plunger is composed of a material having a flex modulus of about 3800 MPa.

In an embodiment, the plunger is composed of a thermoplastic material or a thermosetting material.

Thermoplastic materials include polyacetal, polycarbonate, polyacrylate, polyamide, acryonitrile-butadiene-styrene (ABS), polyvinyl chloride (PVC) and their copolymers, terpolymers, and filled composites thereof. Polyacetal materials include acetal homopolymer, copolymer, and filled materials thereof. The filled materials may include glass spheres filled and glass fiber filled materials thereof.

Thermosetting materials include epoxy, acrylic, urethane, ester, vinyl ester, epoxy-polyester, acrylic-urethane, and fluorovinyl. In an embodiment, acrylic materials include a reactive functionality such as an acid, hydroxyl, or epoxy group. In an embodiment, the epoxy material comprises a reactive functionality that can be cured by a method selected from the group consisting of visible, UV and thermal crosslinking. In an exemplary embodiment, the thermosetting material is an epoxy homopolymer, copolymer or filled composite thereof.

Exemplary embodiments provide methods for modulating the FtF of a firing mechanism comprising a plunger having two plunger arms separated by a plunger arm width, the method comprising the steps of altering at least one feature of the plunger selected from the group consisting of an ICS angle, an ICS length, an SCS angle, an SCS width, a plunger arm width, a plunger base bridge angle, protrusion angle (PA), protrusion height (PH), and a flex modulus of the material of at least a portion of the plunger. In an embodiment, the ICS angle is modified. In another embodiment, the ICS length is modified. In another embodiment, the SCS angle is modified. In another embodiment, the SCS length is modified. In another embodiment, the plunger arm width is modified. In another embodiment, the plunger base bridge angle is modified. In another embodiment, the plunger protrusion angle is modified. In another embodiment, the plunger protrusion height is modified. In another embodiment, the flex modulus of the material of at least a portion of the plunger is modified. In an embodiment, the FtF is increased. In another embodiment, the FtF is decreased.

Exemplary embodiments also provide improved individual components, or combinations thereof, of an exemplary firing mechanism assembly.

Exemplary embodiments further provide automatic injection devices including any one of the firing mechanisms described herein. In an embodiment, the automatic injection devices contain a dose of a TNF inhibitor, e.g., a human TNFα antibody, or antigen-binding portion thereof for injection into a patient's body.

Exemplary embodiments provide methods of forming a syringe plunger for an automatic injection device. The methods teach forming a distal end of the syringe plunger, a proximal end of the syringe plunger and an intermediate portion between the distal end and the proximal end. The methods teach forming a bifurcated distal end with a first plunger arm having a first conical surface and a second conical surface, and a second plunger arm having a first conical surface and a second conical surface. The methods teach forming a first contact surface with the first conical surface of the first plunger arm and the first conical surface of the second plunger arm. The first contact surface configured to initially contact a firing engagement mechanism of an automatic injection device. The first contact surface disposed at a first angle of between about 40° and about 80° with respect to a longitudinal axis of the syringe plunger. The methods teach forming a second contact surface with the second conical surface of the first plunger arm and the second conical surface of the second plunger arm. The second contact surface configured to contact the firing engagement mechanism subsequent to contact by the first contact surface.

BRIEF DESCRIPTION OF THE DRAWINGS

The foregoing and other objects, aspects, features and advantages of exemplary embodiments will be more fully understood from the following description when read together with the accompanying drawings, in which:

FIG. 1 illustrates a perspective view of an exemplary automatic injection device in which caps that cover proximal and distal ends of the housing are removed.

FIG. 2 illustrates a perspective view of the exemplary automatic injection device of FIG. 1 in which the housing is capped.

DETAILED DESCRIPTION

Figure 5:
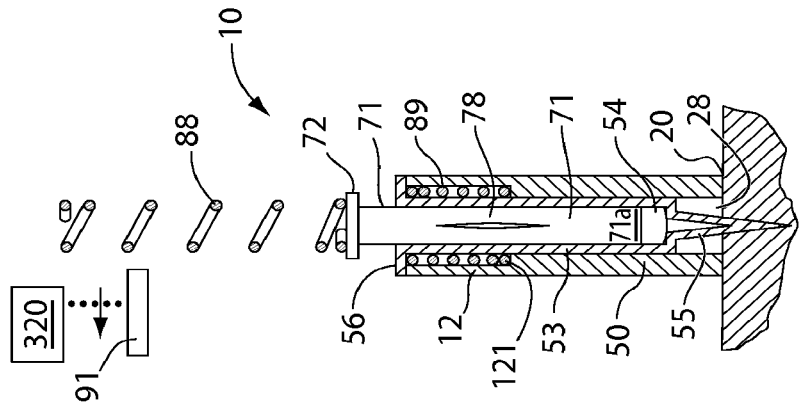
FIG. 5 (prior art) illustrates a cross-sectional schematic view of the exemplary automatic injection device of FIGS. 3 and 4 during an additional stage of operation.

Exemplary embodiments cure the above-described deficiencies of conventional automatic injection devices by improving the FtF required to engage the firing mechanism. Exemplary embodiments provide, in part, firing mechanism assemblies with improved FtF, automatic injection devices including firing mechanism assemblies with improved FtF, methods for improving the FtF in automatic injection devices, and methods for using automatic injection devices with improved FtF to deliver a substance into a patient's body. Automatic injection devices provided by exemplary embodiments may be used for administering any type of substance into a patient's body including, but not limited to, liquid therapeutic agents, e.g., adalimumab (HUMIRA®).

Automatic injection devices are convenient, less painful, and have a hidden needle to remove apprehension and anxiety for patients who are "needle phobic." Exemplary automatic injection devices offer safety advantages. Unlike conventional syringes, there is no needle exposure with the automatic injection device. Exemplary automatic injection devices may include a needle sleeve that surrounds the needle and protects patients from needle-stick injury before and after use. In addition, a safety cap on the automatic injection device may prevent accidental misfiring, a potential occurrence with pre-filled syringes. An audible "click" may announce the beginning of an injection, and a distinctive indicator in an inspection window may show the patient that the complete dose was fully administered.

DEFINITIONS

Certain terms are defined in this section to facilitate understanding of exemplary embodiments.

The automatic injection device, e.g., autoinjector pen, of exemplary embodiments may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody, antibody portion, or other TNFα inhibitor may vary according to factors such as the disease state, age, sex, and weight of the patient, and the ability of the antibody, antibody portion, or other TNFα inhibitor to elicit a desired response in the patient. A therapeutically effective amount is also one in which any toxic or detrimental effects of the antibody, antibody portion, or other TNFα inhibitor are outweighed by the therapeutically beneficial effects. A "prophylactically effective amount" refers to an amount effective, at dosages and for periods of time necessary, to achieve the desired prophylactic result. Typically, since a prophylactic dose is used in patients prior to or at an earlier stage of disease, the prophylactically effective amount will be less than the therapeutically effective amount.

A "substance" refers to any type of drug, biologically active agent, biological substance, chemical substance or biochemical substance that is capable of being administered in a therapeutically effective amount to a patient employing exemplary automatic injection devices. Exemplary substances include, but are not limited to, agents in a liquid state. Such agents may include, but are not limited to, adalimumab (HUMIRA®) and proteins that are in a liquid solution, e.g., fusion proteins and enzymes. Examples of proteins in solution include, but are not limited to, Pulmozyme (Dornase alfa), Regranex (Becaplermin), Activase (Alteplase), Aldurazyme (Laronidase), Amevive (Alefacept), Aranesp (Darbepoetin alfa), Becaplermin Concentrate, Betaseron (Interferon beta-1b), BOTOX (Botulinum Toxin Type A), Elitek (Rasburicase), Elspar (Asparaginase), Epogen (Epoetin alfa), Enbrel (Etanercept), Fabrazyme (Agalsidase beta), Infergen (Interferon alfacon-1), Intron A (Interferon alfa-2a), Kineret (Anakinra), MYOBLOC (Botulinum Toxin Type B), Neulasta (Pegfilgrastim), Neumega (Oprelvekin), Neupogen (Filgrastim), Ontak (Denileukin diftitox), PEGASYS (Peginterferon alfa-2a), Proleukin (Aldesleukin), Pulmozyme (Dornase alfa), Rebif (Interferon beta-1a), Regranex (Becaplermin), Retavase (Reteplase), Roferon-A (Interferon alfa-2), TNKase (Tenecteplase), and Xigris (Drotrecogin alfa), Arcalyst (Rilonacept), NPlate (Romiplostim), Mircera (methoxypolyethylene glycol-epoetin beta), Cinryze (C1 esterase inhibitor), Elaprase (idursulfase), Myozyme (alglucosidase alfa), Orencia (abatacept), Naglazyme (galsulfase), Kepivance (palifermin) and Actimmune (interferon gamma-1b).

A protein in solution may also be an immunoglobulin or antigen-binding fragment thereof, such as an antibody or antigen-binding portion thereof. Examples of antibodies that may be used in an exemplary automatic injection device include, but are not limited to, chimeric antibodies, non-human antibodies, human antibodies, humanized antibodies, and domain antibodies (dAbs). In an exemplary embodiment, the immunoglobulin or antigen-binding fragment thereof, is an anti-TNFα and/or an anti-IL-12 antibody (e.g., it may be a dual variable domain immunoglobulin (DVD) Ig™). Other examples of immunoglobulins or antigen-binding fragments thereof that may be used in the methods and compositions of exemplary embodiments include, but are not limited to, 1D4.7 (anti-IL-12/IL-23 antibody; Abbott Laboratories); 2.5(E)mg1 (anti-IL-18; Abbott Laboratories); 13C5.5 (anti-IL-13 antibody; Abbott Laboratories); J695 (anti-IL-12; Abbott Laboratories); Afelimomab (Fab 2 anti-TNF; Abbott Laboratories); Humira (adalimumab) Abbott Laboratories); Campath (Alemtuzumab); CEA-Scan Arcitumomab (fab fragment); Erbitux (Cetuximab); Herceptin (Trastuzumab); Myoscint (Imciromab Pentetate); ProstaScint (Capromab Pendetide); Remicade (Infliximab); ReoPro (Abciximab); Rituxan (Rituximab); Simulect (Basiliximab); Synagis (Palivizumab); Verluma (Nofetumomab); Xolair (Omalizumab); Zenapax (Daclizumab); Zevalin (Ibritumomab Tiuxetan); Orthoclone OKT3 (Muromonab-CD3); Panorex (Edrecolomab); Mylotarg (Gemtuzumab ozogamicin); golimumab (Centocor); Cimzia (Certolizumab pegol); Soliris (Eculizumab); CNTO 1275 (ustekinumab); Vectibix (panitumumab); Bexxar (tositumomab and $I^{131}$ tositumomab); and Avastin (bevacizumab).

Additional examples of immunoglobulins, or antigen-binding fragments thereof, that may be used in the methods and compositions of exemplary embodiments include, but are not limited to, proteins comprising one or more of the following: the D2E7 light chain variable region (SEQ ID NO: 1), the D2E7 heavy chain variable region (SEQ ID NO: 2), the D2E7 light chain variable region CDR3 (SEQ ID NO: 3), the D2E7 heavy chain variable region CDR3 (SEQ ID NO:4), the D2E& light chain variable region CDR2 (SEQ ID NO: 5), the D2E7 heavy chain variable region CDR2 (SEQ ID NO: 6), the D2E7 light chain variable region CDR1 (SEQ ID NO: 7), the D2E7 heavy chain variable region CDR1 (SEQ ID NO: 8), the 2SD4 light chain variable region (SEQ ID NO: 9), the 2SD4 heavy chain variable region (SEQ ID NO: 10), the 2SD4 light chain variable CDR3 (SEQ ID NO: 11), the EP B12 light chain variable CDR3 (SEQ ID NO: 12), the VL10E4 light chain variable CDR3 (SEQ ID NO: 13), the VL100A9 light chain variable CDR3 (SEQ ID NO: 14), the VLL100D2 light chain variable CDR3 (SEQ ID NO: 15), the VLL0F4 light chain variable CDR3 (SEQ ID NO: 16), the LOE5 light chain variable CDR3 (SEQ ID NO: 17), the VLLOG7 light chain variable CDR3 (SEQ ID NO: 18), the VLLOG9 light chain variable CDR3 (SEQ ID NO: 19), the VLLOH1 light chain variable CDR3 (SEQ ID NO: 20), the VLLOH10 light chain variable CDR3 (SEQ ID NO: 21), the VL1B7 light chain variable CDR3 (SEQ ID NO: 22), the VL1C1 light chain variable CDR3 (SEQ ID NO: 23), the VL0.1F4 light chain variable CDR3 (SEQ ID NO: 24), the VL0.1H8 light chain variable CDR3 (SEQ ID NO: 25), the LOE7. A light chain variable CDR3 (SEQ ID NO: 26), the 2SD4 heavy chain variable region CDR (SEQ ID NO: 27), the VH1B11 heavy chain variable region CDR (SEQ ID NO: 28), the VH1D8 heavy chain variable region CDR (SEQ ID NO: 29), the VH1A11 heavy chain variable region CDR (SEQ ID NO: 30), the VH1B12 heavy chain variable region CDR (SEQ ID NO: 31), the VH1E4 heavy chain variable region CDR (SEQ ID NO: 32), the VH1F6 heavy chain variable region CDR (SEQ ID NO: 33), the 3C-H2 heavy chain variable region CDR (SEQ ID NO: 34), and the VH1-D2.N heavy chain variable region CDR (SEQ ID NO: 35).

"Human TNFα" (abbreviated herein as hTNFα, or simply hTNF) refers to a human cytokine that exists as a 17 kD secreted form and a 26 kD membrane associated form, the biologically active form of which is composed of a trimer of noncovalently bound 17 kD molecules. The structure of hTNFα is described further in, for example, Pennica, D., et al. (1984) *Nature* 312:724-729; Davis, J. M., et al. (1987) *Biochem.* 26:1322-1326; and Jones, E. Y., et al. (1989) *Nature* 338:225-228. The term human TNFα is intended to include recombinant human TNFα (rhTNFα), which can be prepared by standard recombinant expression methods or purchased commercially (R & D Systems, Catalog No. 210-TA, Minneapolis, Minn.). TNFα is also referred to as TNF.

The term "TNFα inhibitor" refers to an agent that interferes with TNFα activity. The term also includes each of the anti-TNFα human antibodies (used interchangeably herein with TNFα antibodies) and antibody portions described herein as well as those described in U.S. Pat. Nos. 6,090,382; 6,258,562; 6,509,015; 7,223,394; and 6,509,015. In one embodiment, the TNFα inhibitor used in the invention is an anti-TNFα antibody, or a fragment thereof, including infliximab (Remicade®, Johnson and Johnson; described in U.S. Pat. No. 5,656,272); CDP571 (a humanized monoclonal anti-TNF-alpha IgG4 antibody); CDP 870 (a humanized monoclonal anti-TNF-alpha antibody fragment); an anti-TNF dAb (Peptech); CNTO 148 (golimumab; Centocor, see WO 02/12502 and U.S. Pat. Nos. 7,521,206 and 7,250,165); and adalimumab (HUMIRA® Abbott Laboratories, a human anti-TNF mAb, described in U.S. Pat. No. 6,090,382 as D2E7). Additional TNF antibodies that may be used in the invention are described in U.S. Pat. Nos. 6,593,458; 6,498,237; 6,451,983; and 6,448,380. In another embodiment, the TNFα inhibitor is a TNF fusion protein, e.g., etanercept (Enbrel®, Amgen; described in WO 91/03553 and WO 09/406476). In another embodiment, the TNFα inhibitor is a recombinant TNF binding protein (r-TBP-I) (Serono).

In one embodiment, the term "TNFα inhibitor" excludes infliximab. In one embodiment, the term "TNFα inhibitor" excludes adalimumab. In another embodiment, the term "TNFα inhibitor" excludes adalimumab and infliximab.

In one embodiment, the term "TNFα inhibitor" excludes etanercept, and, optionally, adalimumab, infliximab, and adalimumab and infliximab.

In one embodiment, the term "TNFα antibody" excludes infliximab. In one embodiment, the term "TNFα antibody" excludes adalimumab. In another embodiment, the term "TNFα antibody" excludes adalimumab and infliximab.

"Antibody" refers to immunoglobulin molecules generally comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The antibodies of the invention are described in further detail in U.S. Pat. Nos. 6,090,382; 6,258,562; and 6,509,015.

"Antigen-binding portion" of an antibody (or simply "antibody portion") refers to one or more fragments of an antibody that retain the ability to specifically bind to an antigen (e.g., hTNFα). Fragments of a full-length antibody can perform the antigen-binding function of an antibody. Examples of binding fragments encompassed within the term "antigen-binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546), which consists of a VH or VL domain; (vi) an isolated complementarity determining region (CDR); and (vii) a dual variable domain immunoglobulin (DVD-Ig). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). The antibody portions of the invention are described in further detail in U.S. Pat. Nos. 6,090,382; 6,258,562; and 6,509,015.

"Recombinant human antibody" refers to all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) *Nucl. Acids Res.* 20:6287) or antibodies prepared, expressed, created or isolated by any other means that involves splicing of human immunoglobulin gene sequences to other DNA sequences. Such recombinant human antibodies have variable and constant regions derived from human germ line immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germ line VH and VL sequences, may not naturally exist within the human antibody germ line repertoire in vivo.

Such chimeric, humanized, human, and dual specific antibodies can be produced by recombinant DNA techniques known in the art, for example using methods described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al. (1988) Science 240:1041-1043; Liu et al. (1987) Proc. Natl. Acad. Sci. USA 84:3439-3443; Liu et al. (1987) J. Immunol. 139:3521-3526; Sun et al. (1987) Proc. Natl. Acad. Sci. USA 84:214-218; Nishimura et al. (1987) Cancer Res. 47:999-1005; Wood et al. (1985) Nature 314:446-449; Shaw et al. (1988) J. Natl. Cancer Inst. 80:1553-1559; Morrison (1985) Science 229:1202-1207; Oi et al. (1986) BioTechniques 4:214; U.S. Pat. No. 5,225,539; Jones et al. (1986) Nature 321:552-525; Verhoeyan et al. (1988) Science 239:1534; and Beidler et al. (1988) J. Immunol. 141:4053-4060, Queen et al. (1989) Proc. Natl. Acad. Sci. USA 86:10029-10033 (1989); U.S. Pat. Nos. 5,530,101; 5,585,089; 5,693,761; 5,693,762; WO 90/07861; and U.S. Pat. No. 5,225,539.

"Isolated antibody" refers to an antibody that is substantially free of other antibodies having different antigenic specificities (e.g., an isolated antibody that specifically binds hTNFα and is substantially free of antibodies that specifically bind antigens other than hTNFα). An isolated antibody that specifically binds hTNFα may have cross-reactivity to other antigens, such as TNFα molecules from other species. Moreover, an isolated antibody may be substantially free of other cellular material and/or chemicals.

"Neutralizing antibody" (or an "antibody that neutralized hTNFα activity") refers to an antibody whose binding to hTNFα results in inhibition of the biological activity of hTNFα. This inhibition of the biological activity of hTNFα can be assessed by measuring one or more indicators of hTNFα biological activity, such as hTNFα-induced cytotoxicity (either in vitro or in vivo), hTNFα-induced cellular activation and hTNFα binding to hTNFα receptors. These indicators of hTNFα biological activity can be assessed by one or more of several standard in vitro or in vivo assays known in the art (see U.S. Pat. No. 6,090,382). Preferably, the ability of an antibody to neutralize hTNFα activity is assessed by inhibition of hTNFα-induced cytotoxicity of L929 cells. As an additional or alternative parameter of hTNFα activity, the ability of an antibody to inhibit hTNFα-induced expression of ELAM-1 on HUVEC, as a measure of hTNFα-induced cellular activation, can be assessed.

"Surface plasmon resonance" refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Example 1 of U.S. Pat. No. 6,258,562 and Jönsson et al. (1993) *Ann. Biol. Clin.* 51:19; Jönsson et al. (1991) *Biotechniques* 11:620-627; Jöhnsson et al. (1995) *J. Mol. Recognit.* 8:125; and Johnnson et al. (1991) *Anal. Biochem.* 198:268.

"$K_{off}$" refers to the off rate constant for dissociation of an antibody from the antibody/antigen complex.

"$K_d$" refers to the dissociation constant of a particular antibody-antigen interaction.

"$IC_{50}$" refers to the concentration of the inhibitor required to inhibit the biological endpoint of interest, e.g., neutralize cytotoxicity activity.

"Dose" refers to an amount of a substance, such as a TNFα inhibitor, which is administered to a patient preferably using the automatic injection device of the invention. In one embodiment, the dose comprises an effective amount, for example, including 20 mg, 30 mg, 40 mg, 50 mg, 60 mg, 70 mg, 80 mg, 90 mg, 100 mg, 110 mg, 120 mg, 130 mg, 140 mg, 150 mg, and 160 mg, of the TNFα inhibitor adalimumab.

"Dosing" refers to the administration of a substance (e.g., an anti-TNFα antibody) to achieve a therapeutic objective (e.g., treatment of rheumatoid arthritis).

"Dosing regimen" describes a treatment schedule for a substance, such as a TNFα inhibitor, e.g., a treatment schedule over a prolonged period of time and/or throughout the course of treatment, e.g. administering a first dose of a TNFα inhibitor at week 0 followed by a second dose of a TNFα inhibitor on a biweekly dosing regimen.

"Biweekly dosing regimen", "biweekly dosing", and "biweekly administration" refer to the time course of administering a substance (e.g., an anti-TNFα antibody) to a patient to achieve a therapeutic objective, e.g., throughout the course of treatment. The biweekly dosing regimen is not intended to include a weekly dosing regimen. Preferably, the substance is administered every 9 to 19 days, more preferably, every 11 to 17 days, even more preferably, every 13 to 15 days, and most preferably, every 14 days. In one embodiment, the biweekly dosing regimen is initiated in a patient at week 0 of treatment. In another embodiment, a maintenance dose is administered on a biweekly dosing regimen. In one embodiment, both the loading and maintenance doses are administered according to a biweekly dosing regimen. In one embodiment, biweekly dosing includes a dosing regimen wherein doses of a TNFα inhibitor are administered to a patient every other week beginning at week 0. In one embodiment, biweekly dosing includes a dosing regimen where doses of a TNFα inhibitor are administered to a patient every other week consecutively for a given time period, e.g., 4 weeks, 8 weeks, 16, weeks, 24 weeks, 26 weeks, 32 weeks, 36 weeks, 42 weeks, 48 weeks, 52 weeks, 56 weeks, etc. Biweekly dosing methods are also described in U.S. 2003/0235585.

"Combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent.

"Concomitant" as in the phrase "concomitant therapeutic treatment" includes administering an agent in the presence of a second agent. A concomitant therapeutic treatment method includes methods in which the first, second, third, or additional substances are co-administered. A concomitant therapeutic treatment method also includes methods in which the first or additional agents are administered in the presence of a second or additional substances, wherein the second or additional agents, for example, may have been previously administered. A concomitant therapeutic treatment method may be executed step-wise by different patients. For example, one subject may administer to a patient a first agent and a second subject may to administered to the patient a second substance, and the administering steps may be executed at the same time, or nearly the same time, or at distant times, so long as the first substance (and additional substances) are after administration in the presence of the second substance (and additional substances). The actor and the patient may be the same entity (e.g., human).

"Combination therapy" refers to the administration of two or more therapeutic substances, e.g., an anti-TNFα antibody and another drug. The other drug(s) may be administered concomitant with, prior to, or following the administration of an anti-TNFα antibody.

"Treatment" refers to therapeutic treatment, as well as prophylactic or suppressive measures, for the treatment of a disorder, such as a disorder in which TNFα is detrimental, e.g., rheumatoid arthritis.

A "patient" refers to any type of animal, human or non-human, that may be injected a substance using exemplary automatic injection devices.

An "automatic injection device" (or "autoinjector") refers to a device that enables a patient to self-administer a dose of a substance, such as a liquid medication, wherein the automatic injection device differs from a standard syringe by the inclusion of a firing mechanism assembly for automatically delivering the substance into the patient's body by injection when the firing mechanism assembly is engaged. In an exemplary embodiment, the automatic injection device may be wearable on the patient's body.

A "firing mechanism" refers to a mechanism that, when engaged by a firing engagement mechanism, automatically delivers a substance contained in an automatic injection device into a patient's body. A firing engagement mechanism may be any type of mechanism that engages and triggers the firing mechanism including, but not limited to, a firing button that may be pushed by a patient to trigger the firing mechanism.

"Force to fire" (or "FtF") refers to the minimum force that must be delivered to a firing engagement mechanism of an automatic injection device in order to trigger the firing mechanism so that it expels the substance contained in the device. Delivery of a force equal to or greater than the required FtF to a firing engagement mechanism causes the firing engagement mechanism to trigger the firing mechanism so that it expels the substance from the device. On the other hand, delivery of a force lower than the required FtF to the firing engagement mechanism does not trigger the firing mechanism, and the firing mechanism therefore does not expel the substance from the device. An exemplary FtF for an automatic injection device may range between about 5 N and about 25 N. Another exemplary FtF for an automatic injection device may range between about 10 N and about 15 N. Yet another exemplary FtF for an automatic injection device has a minimum value of about 25 N.

The FtF may be delivered to the firing engagement mechanism manually by a patient or automatically by an actuation mechanism. In an exemplary embodiment, the FtF may need to be delivered consistently for a minimum period of time, e.g. 5 seconds, 10 seconds, etc, in order to trigger the firing mechanism.

"Flexural modulus" (or "flex modulus" or "flexural modulus of elasticity") refers to the ratio of maximum stress to maximum strain of a material within the elastic limit of the material, as determined from a stress-strain diagram obtained in a flexure test. The flex modulus of a material is a measure of the material's elasticity, or the ability of the material to be deformed and to subsequently return to its original shape.

"Tabbed foot" or "tab foot" refers to a material attached to or projecting from one or both arms of a bifurcated end of a syringe plunger, and is configured to contact and engage a firing engagement mechanism.

"Initial contact surface" (or "ICS") refers to a portion of the outer surface of a tabbed foot formed at the bifurcated end of a syringe plunger. The ICS is formed between a top surface of the tabbed foot and a secondary contact surface (SCS) of the tabbed foot, and is configured to contact a firing engagement mechanism, e.g., a firing button.

"Secondary contact surface" (or "SCS") refers to a portion of the outer surface of a tabbed foot formed at the bifurcated end of a syringe plunger. The SCS is formed between the ICS of the tabbed foot and a bottom surface of the tabbed foot.

"Initial contact surface angle" or "ICS angle" refers to the angle formed by the ICS relative to the longitudinal axis of the plunger arm.

"Initial contact surface length" or "ICS length" refers to the length of the tabbed foot at a transition point between the ICS and the SCS as measured along an axis transverse to the longitudinal axis.

"Plunger arm width" refers to the distance between the arms of a bifurcated end of a syringe plunger.

"Plunger base bridge angle" (or "PBB angle") refers to the angle formed between the arms of a bifurcated end of a syringe plunger. For example, a PBB angle of 0° means that the plunger arms are parallel to each other. There is a direct relationship between the PBB angle and the plunger arm width in that increasing the PBB angle increases the plunger arm width and decreasing the PBB angle decreases the plunger arm width.

"Pre-filled syringe/device" encompasses a syringe/device that is filled with a substance immediately prior to administration of the substance to a patient and a syringe/device that is filled with a substance and stored in this pre-filled form for a period of time before administration of the substance to a patient.

A "thermoplastic material" refers to a material that has the property of softening or fusing when heated and of hardening and becoming rigid when cooled. A thermoplastic material is a polymer that turns into a liquid when heated sufficiently and freezes into a very glassy state when cooled sufficiently. Thermoplastic materials can be re-melted and cooled repeatedly without the materials undergoing any appreciable chemical change.

Most thermoplastics are high-molecular-weight polymers whose chains associate through weak Van der Waals forces (polyethylene), stronger dipole-dipole interactions and hydrogen bonding (nylon), or even stacking of aromatic rings (polystyrene). Thermoplastic polymers differ from thermosetting polymers (vulcanized rubber) as they, unlike thermosetting polymers, can be re-melted and re-molded. Many thermoplastic materials are addition polymers, e.g., vinyl chain-growth polymers such as polyethylene and polypropylene.

A "thermosetting material" refers to a polymeric material that softens when initially heated and then condenses (often cross-linking) into a hard permanent form. A thermosetting material cannot be softened or reprocessed through the subsequent application of heat.

Thermosetting materials are polymer materials that cure irreversibly. Curing may be performed by applying heat (generally above 200° Celsius) by a chemical reaction (two-part epoxy, for example), or by irradiation (electron beam processing, for example). Thermosetting materials are made of long-chain polymers that cross-link with each other after they have been cured by thermal radiation, ultraviolet (UV) radiation and/or visible radiation and/or after they have been heated. The curing process renders the material permanently hard. Thermosetting plastics are polymer materials that are usually liquid or malleable prior to curing and designed to be molded into their final form or used as adhesives. Some thermosetting plastics are solids, like the molding compounds typically used in semiconductors and integrated circuits.

Exemplary Automatic Injection Devices

Exemplary embodiments will be described below with reference to certain illustrative embodiments. While exemplary embodiments are described with respect to using an automatic injection device to provide an injection of a dose of a liquid medication, one of ordinary skill in the art will recognize that exemplary embodiments are not limited to the illustrative embodiments and that exemplary automatic injection devices may be used to inject any suitable substance into a patient. In addition, components of exemplary automatic injection devices and methods of making and using exemplary automatic injection devices are not limited to the illustrative embodiments described below.

"Distal" refers to a portion or end or component of an exemplary automatic injection device that is farthest from an injection site on the patient's body when the device is held against the patient for an injection or for mimicking an injection.

"Proximal" refers to a portion or end or component of an exemplary automatic injection device that is closest to an injection site on a patient's body when the device is held against the patient for an injection or for mimicking an injection.

FIGS. 1 and 2 illustrate an exemplary automatic injection device 10 suitable for injecting a dose of a substance, such as a liquid drug, into a patient. Figure illustrates a perspective view of the exemplary automatic injection device 10 in which caps that cover proximal and distal ends of the housing are removed. FIG. 2 illustrates a perspective view of the exemplary automatic injection device 10 of FIG. 1 in which the proximal and distal ends of the housing are capped.

Referring to FIG. 1, the automatic injection device 10 includes a housing 12 for housing a container, such as a syringe, containing a dose of a substance to be injected into a patient's body. The housing 12 preferably has a tubular configuration, although one of ordinary skill in the art will recognize that the housing 12 may have any suitable size, shape and configuration for housing a syringe or other container. While exemplary embodiments will be described with respect to a syringe mounted in the housing 12, one of ordinary skill in the art will recognize that the automatic injection device 10 may employ any suitable container for storing and dispensing a substance.

The exemplary syringe is preferably slidably mounted in the housing 12, as described in detail below. When the device is in an inactivated position, the syringe is sheathed and retracted within the housing 12. When the device 10 is actuated, a needle of the syringe projects from a first proximal end 20 of the housing 12 to allow ejection of the substance from the syringe into the patient's body. As shown, the first proximal end 20 of the housing 12 includes an opening 28 through which the needle of the syringe projects during actuation of the device 10.

Referring still to FIG. 1, a second distal end 30 of the housing 12 includes a firing engagement mechanism, e.g., a firing button 32, for actuating a firing mechanism. The housing 12 also houses the firing mechanism, e.g., one or more actuators, that moves the syringe from a sheathed position with the housing 12 to a projecting position and subsequently expels the substance from the syringe into the patient's body.

The exemplary automatic injection device 10 may also include a first removable cap 24 (or needle cap) for covering the first end 20 of the housing 12 to prevent exposure of the needle prior to an injection. In the illustrative embodiment, the first cap 24 may include a boss 26 for locking and/or joining the cap 24 of the device 10 until the patient is ready to activate the device 10. Alternatively, the first cap 24 may include a threaded screw portion, and the internal surface of the housing 12 at opening 28 may include a screw thread. Any suitable mating mechanism may be used in accordance with the teachings of exemplary embodiments.

The housing 12 and caps 24, 34 may further include graphics, symbols and/or numbers to facilitate use of the automatic injection device 10. For example, the housing 12 includes an arrow 125 on an outer surface pointing towards the first end 20 of the device 10 to indicate how the device 10 should be held relative to the patient (i.e., with the first end 20 adjacent to the injection site), as shown in FIG. 2. In addition, the first cap 24 is labeled with a "1" to indicate that a patient should remove the first cap 24 of the device first, and the second cap is labeled with a "2" to indicate that the second cap 34 should be removed after the first cap 24 is removed during preparation for and subsequent injection using the illustrative automatic injection device 10. One of ordinary skill in the art will recognize that the automatic injection device 10 may have any suitable graphics, symbols and/or numbers to facilitate patient instruction, or the automatic injection device may omit such graphics, symbols and/or numbers.

As shown in FIG. 2, the first end 20 of the housing 12 may have a wider diameter than the second end 30. A step 29 may be formed at the transition between the two diameters to accommodate the second cap 34 and to facilitate seating of the second cap 34 on the second end 30 of the housing.

The housing 12 may also preferably include a display window 130 to allow a patient to view the contents of the syringe housed within the housing 12. The window 130 may include an opening in the sidewall of the housing 12, or may include a translucent material in the housing 12 to allow viewing of the interior of the device 10.

The housing 12 may be formed of any suitable surgical material including, but not limited to, plastic and other known materials.

Figure 4:
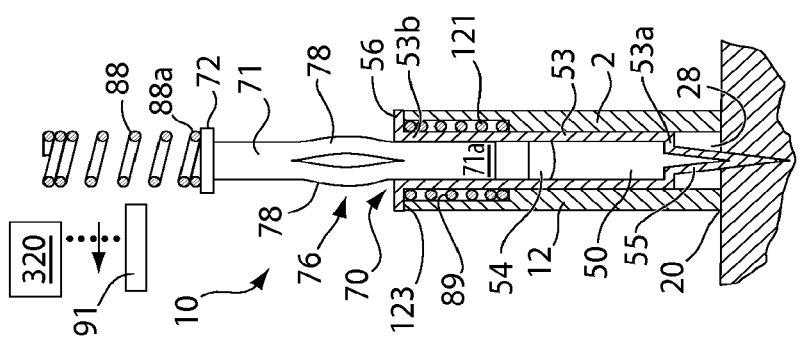
FIG. 4 (prior art) illustrates a cross-sectional schematic view of the exemplary automatic injection device of FIG. 3 during a subsequent stage of operation.
Figure 3:
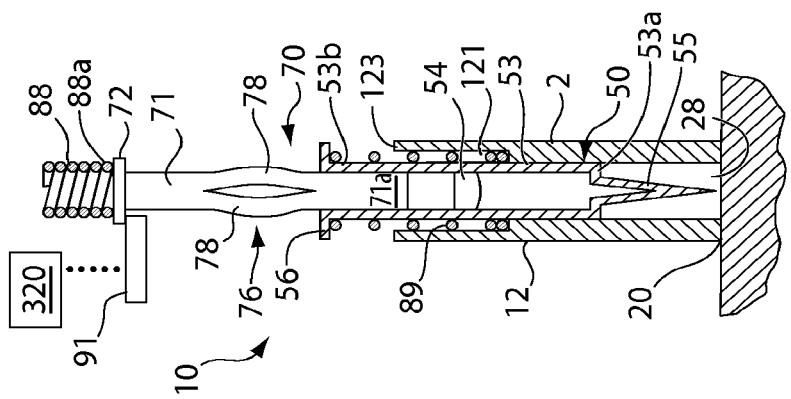
FIG. 3 (prior art) illustrates a cross-sectional schematic view of an exemplary automatic injection device prior to use.

FIGS. 3-5 (prior art) are schematic views of interior components of an exemplary automatic injection device 10. FIG. 3 (prior art) illustrates a cross-sectional schematic view of an exemplary automatic injection device prior to use. FIG. 4 (prior art) illustrates a cross-sectional schematic view of the exemplary automatic injection device of FIG. 3 during an intermediate stage of operation. FIG. 5 (prior art) illustrates a cross-sectional schematic view of the exemplary automatic injection device of FIGS. 3 and 4 during a post-injection stage of operation.

Still referring to FIGS. 3-5, a syringe 50 or other suitable container for a substance is disposed within the interior of the housing 12. An exemplary syringe 50 may include a hollow barrel portion 53 for holding a dose of a liquid substance to be injected into a patient's body. An exemplary barrel portion 53 is substantially cylindrical in shape, although one of ordinary skill in the art will recognize that the barrel portion 53 may have any suitable shape or configuration. A seal, illustrated as a bung 54, seals the dose within the barrel portion 53. The syringe 50 may also include a hollow needle 55 connected to and in fluid communication with the barrel portion 53, through which the dose can be ejected by applying pressure to the bung 54. The hollow needle 55 extends from a first proximal end 53a of the barrel portion 53. The second distal end 53b of the barrel portion 53 includes a flange 56, or other suitable mechanism, for abutting a stop (represented schematically as 123) in the housing 12 to limit the movement of the syringe 50 within the housing 12, as described below. One of ordinary skill in the art will recognize that exemplary embodiments are not limited to the illustrative embodiment of the syringe 50 and that any suitable container for containing a dose of a substance to be injected may be used in accordance with the teachings of exemplary embodiments.

In an exemplary embodiment, the needle 55 may be a fixed twenty-seven gauge one-half inch needle. The tip of an exemplary hollow needle 55 may include a number of bevels, e.g., five bevels, to facilitate insertion. However, the needle 55 may have any suitable size, shape and configuration suitable for piercing a patient's skin to deliver a substance to the patient's body, and is not limited to the illustrative embodiment. Suitable types of needles are well-known in the art.

The automatic injection device 10 shown in FIGS. 3-5 may include an exemplary syringe actuator 70, illustrated as a plunger, for selectively moving and actuating the syringe 50 to inject the dose contained in the syringe 50 into a patient's body. The exemplary plunger 70 may include a rod portion 71 having a first end 71a integral with, e.g., connected to and/or in fluid communication with, the bung 54 for selectively applying pressure to the bung 54 to expel the dose from the needle 55. The plunger 70 may include a flanged second end 72. In an exemplary embodiment, the plunger 70 may include multiple components than those illustrated in FIGS. 3-5. In an exemplary embodiment, the device 10 may include more or fewer actuators than those illustrated in FIGS. 3-5.

The plunger 70 may be biased forward towards the first end 20 of the device 10 by a first biasing mechanism, illustrated as a coil spring 88, disposed about or above the flanged second end 72 of the plunger 70. A proximal end 88a of the coiled spring 88 may abuts the flanged second end 72 of the plunger 70 to selectively apply pressure to the plunger 70 and to move the plunger 70 proximally. Alternatively, the plunger 70 may extend through the center of the spring 88.

As illustrated in FIG. 3, prior to use of the device 10, the coil spring 88 (or another suitable mechanism) may be compressed between the plunger 70 and the housing 12, thus storing energy. A trigger 91, which may be activated by any suitable actuation means such as the firing button 32, may retain the plunger 70 and the first biasing mechanism 88 in a retracted, latched position before the firing button 32 is activated. The trigger 91 may latch the flanged second end 72 of the plunger 70. When the firing button 32 or other actuation means is activated, the trigger 91 may release the flanged second end 72 of the plunger 70, allowing the coil spring 88 to propel the plunger 70 towards the first end of the device 10.

A second biasing mechanism, illustrated as an exemplary coil spring 89, may hold the syringe 50 in a retracted position within the housing 12 prior to use, as shown in FIG. 3. In the retracted position, the needle 55 may be preferably sheathed entirely within the housing 12. The exemplary syringe coil spring 89 may be disposed about the proximal portion of the barrel portion 53 and may be seated in a shelf 121 formed within the housing interior. The top end of the coil spring 89 may abut the flanged second end 56 of the syringe 50. The spring force of the second biasing mechanism 89 may push the flanged second end 56 of the syringe 50 away from the first end 20 of the housing 12, thereby holding the syringe 50 in the retracted position until activated. Other components of the device 10 may also position the syringe 50 relative to the housing 12.

The first biasing mechanism 88 and the second biasing mechanism 89 may have any suitable configuration and tension suitable for use in biasing certain components of the device. For example, the first biasing mechanism 88 may have any suitable size, shape, energy and properties suitable for moving the plunger 70 and the syringe 50 forward when released. The second biasing mechanism 89 may have any suitable size, shape, energy and properties suitable for retracting the syringe 50 prior to activation. Other suitable means for facilitating movement of the plunger 70 and/or syringe 50 may also be used.

Referring still to the illustrative embodiment of FIGS. 3-5, the plunger 70 may include an exemplary radially compressible expanded portion 76, e.g., in the center of the plunger 70. In an illustrative embodiment, the rod 71 may be split, e.g., in a central portion and expanded to form a pair of projecting elbows 78 that define the radially compressible expanded portion 76. The projecting elbows 78 may be pre-formed as part of the molded plunger 70 or, alternatively, may be attached to the plunger 70 separately. The projecting elbows 78 may be compressible so that they can be moved radially inwardly to cause that portion of the rod 71 to adopt a circumference similar to the rest of the rod 71. The compressible expanded portion 76 facilitates movement of the syringe 50, followed by expulsion of the dose in two substantially separate stages, as described below.

Referring to FIG. 4, when an activation means 320 activates the trigger 91 to release the plunger 70, the spring force of the coil spring 88 propels the plunger 70 forward (proximally). During a first operational stage, the moving plunger 70 pushes the syringe 50 forward such that the tip of the needle 55 projects from the first end 20 of the housing 12. The initial biasing force provided by the first coil spring 88 is sufficient to overcome the biasing force of the second coil spring 89 to allow movement of the syringe 50 against the backward biasing force of the second coil spring 89. In the first operational stage, the expanded region 76 of the plunger 70, formed by the projecting elbows 78, rests against the second end 56 of the barrel portion 53. This prevents the plunger 70 from traveling within the syringe barrel portion 53. In this manner, all biasing force from the first coil spring 88 is applied to move the syringe 50 forward towards the first end 20 of the device 10.

The activation means 320 may have any suitable size, shape, configuration and location suitable for releasing the plunger 70 or otherwise activating the device 10. For example, the activation means 320 may include a firing button 32 formed on a distal end 30 of the housing 12, and/or may include another suitable device, such as a latch, twist-activated switch and other devices known in the art. While the illustrative activation means 320 is located towards a distal end 30 of the device 10, one of ordinary skill in the art will recognize that the activation means 320 may be positioned in any suitable location on the device 10.

The forward motion of the syringe 50 towards the proximal end 20 of the device 10 may continue against the biasing force of the coil spring 89 until the flanged end 56 of the barrel portion 53 abuts the stop 123, such as a protrusion or flange, on the housing 12, as shown in FIG. 4, thereby forming a stopping mechanism 56, 123. One of ordinary skill in the art will recognize that alternate stopping mechanisms may be employed and that exemplary embodiments are not limited to the illustrative stopping mechanism.

As further shown in FIG. 4, the first operational stage may propel the tip of the needle 55 through the opening 28 at the first end 20 of the device 10, so that the needle 55 may pierce the patient's skin. During this stage, the syringe barrel portion 53 may preferably remain sealed without expelling the substance through the needle 55. The interference caused by the stopping mechanism 56, 123 may maintain the needle 55 in a selected position extending from the proximal open end 28 of the device 10 during subsequent steps. Until the stopping mechanism 56, 123 stops the movement of the syringe 50, the compressible expanded portion 76 of the plunger 70 may prevent movement of the plunger 70 relative to the barrel portion 53. The stopping mechanism 56, 123 may be positioned at any suitable location relative to the open first end 20 to allow the syringe 50 to penetrate the skin by any suitable depth suitable for an injection.

The second operational stage commences after the stop 123 of the housing 12 catches the flanged portion 56, stopping further movement of the barrel portion 53. During this stage, the continued biasing force of the coil spring 88 may continue to push the plunger 70 relative to the housing 12, as shown in FIG. 5. The biasing force may cause the elbows 78 of the plunger 70 to compress radially inward and slide into the interior of the barrel portion 53. While the interference between components 123 and 56 may retain the barrel portion 53 in a selected position (with the needle 55 exposed) and with the elbows 78 in a collapsed stage, the coil spring 88 may push the plunger 70 within the barrel portion 53. After the plunger 70 overcomes the necessary force to allow the elbows 78 to compress and extend into the barrel portion 53, the plunger 70 may apply pressure to the bung 54, causing ejection of the substance contained in the syringe 50 through the projecting needle 55. Because the needle 55 was made to penetrate the patient's skin in the first operational stage, the substance contained in the barrel portion 53 of the syringe 50 is injected directly into a portion of the patient's body.

Figure 6:
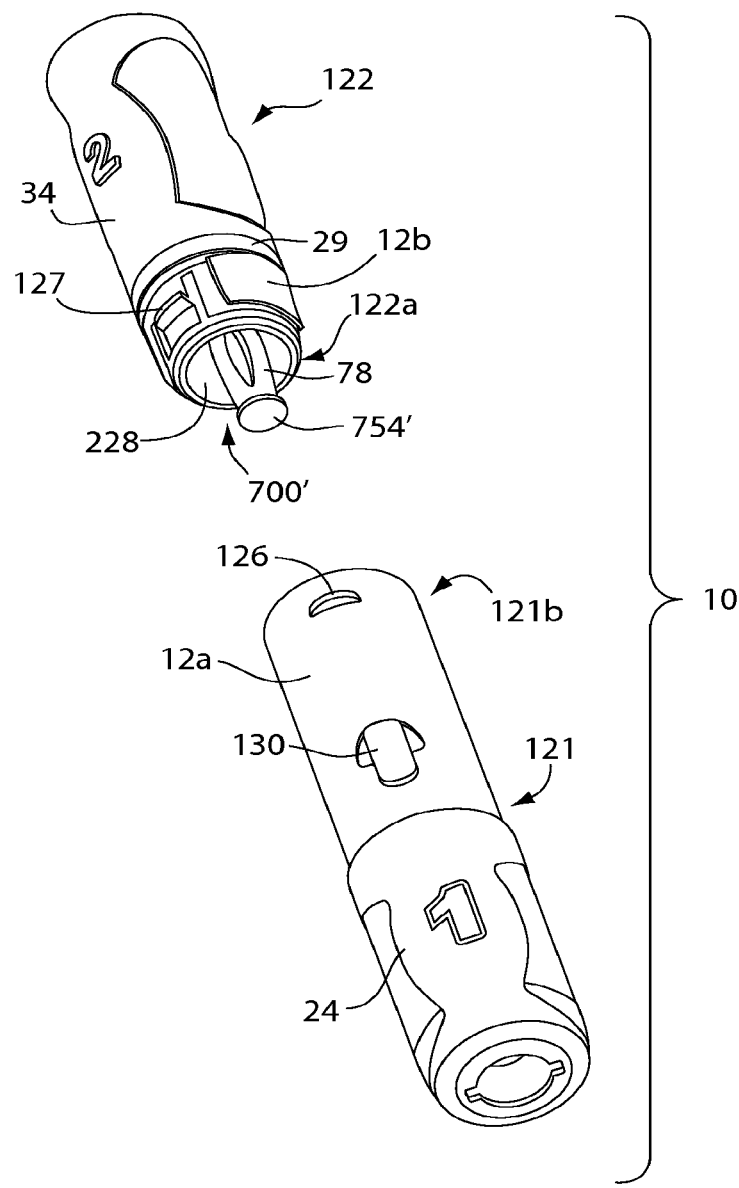
FIG. 6 illustrates a perspective view of an exemplary automatic injection device with a syringe housing assembly and a firing mechanism assembly.

FIG. 6 illustrates a perspective view of an exemplary automatic injection device 10 including a syringe housing assembly and a firing mechanism assembly. In an exemplary embodiment, the automatic injection device 10 may include two interlocking components: a syringe housing assembly 121 containing the proximal components of the device 10 (e.g., the syringe barrel 53, coil spring 89, needle 55 and other proximal components), and a firing mechanism assembly 122 containing the distal components of the device 10 (e.g., the means for actuating the syringe 50). The syringe housing assembly 121 and the firing mechanism assembly 122 may be coupled through any suitable means. In an exemplary embodiment, a proximal end 122a of the firing mechanism assembly 122 may be sized and configured to be inserted into a distal end 121b of the syringe housing assembly 121. In addition, one or more tabs 127 on the proximal end 122a of the firing mechanism assembly 122 may snap-fit into corresponding openings 126 on the distal end 121b of the syringe housing assembly 122 to ensure alignment and coupling of the two assemblies 121, 122 and the components housed therein.

Figure 7:
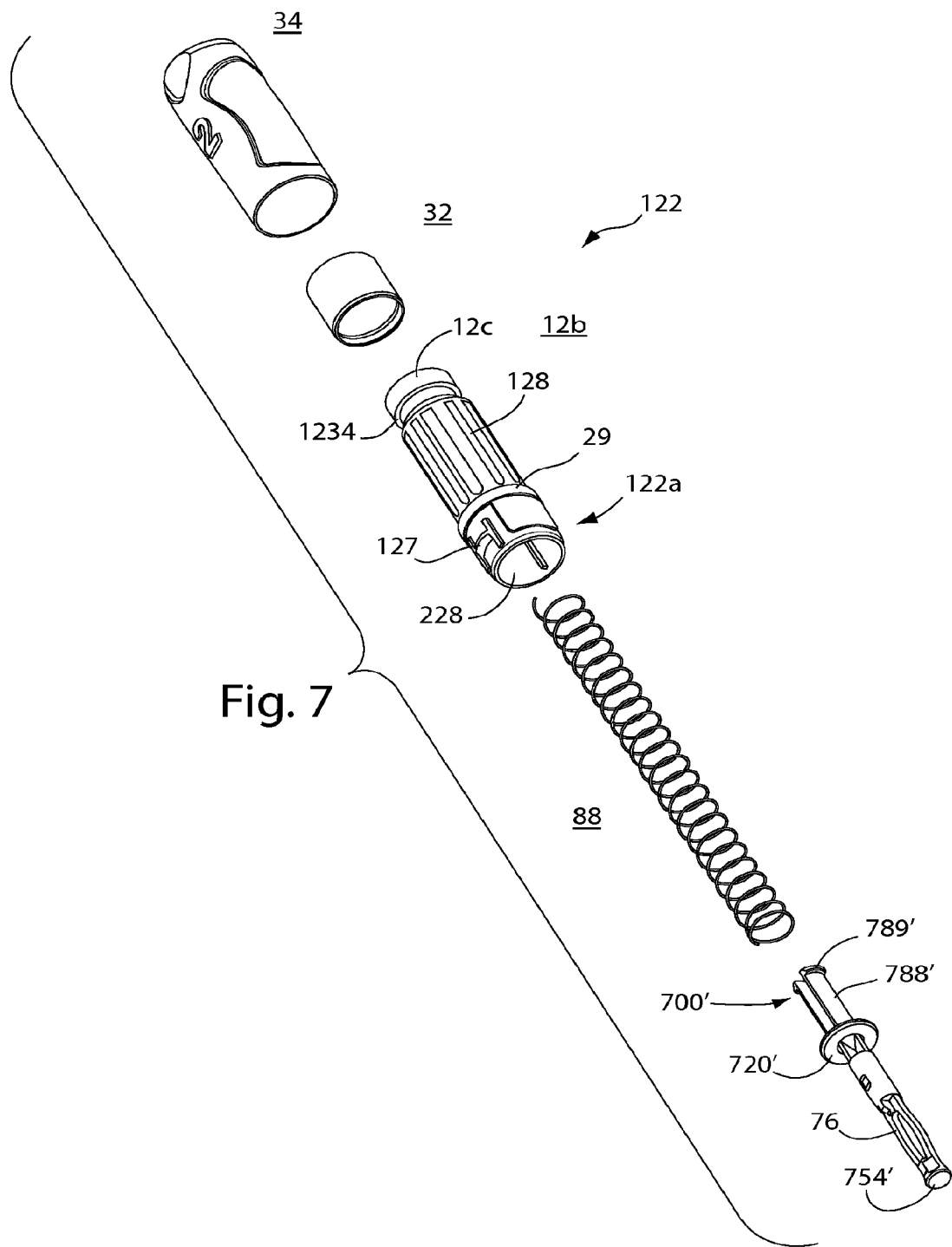
FIG. 7 illustrates a perspective view of the firing mechanism assembly of the exemplary automatic injection device of FIG. 6.

FIG. 7 illustrates a perspective view of the firing mechanism assembly of the exemplary automatic injection device of FIG. 6. The firing mechanism assembly 122 may include the exemplary firing button 32, the exemplary actuator cap 34, the exemplary distal housing component 12b (firing body), and the exemplary coil spring 88 or other biasing mechanism. The firing mechanism assembly 122 may also include a syringe actuator, illustrated as a syringe actuation component 700', which extends from the proximal end 122a of the distal housing component 12b for moving the syringe 50 forward within the housing 12 in a first stage, and for actuating the syringe 50 to expel its contents in a second stage.

Figure 8:
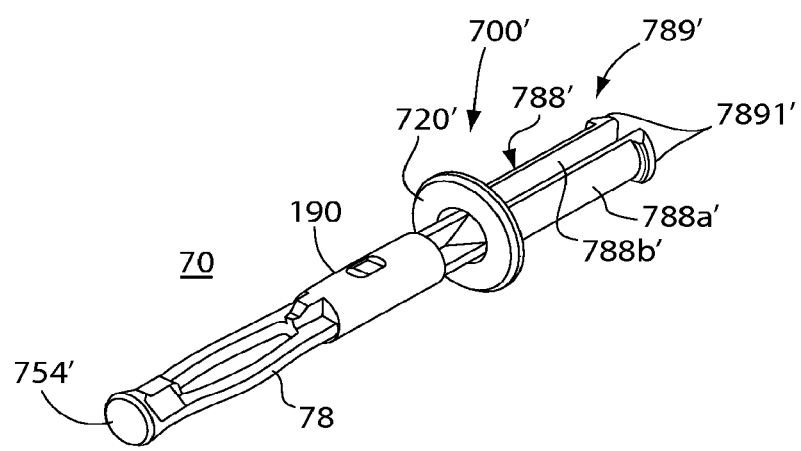
FIG. 8 illustrates a perspective view of a syringe actuation component of the exemplary firing mechanism assembly of FIG. 7.

The syringe actuation component 700' of FIGS. 2 and 8 further may include an indicator 190 in a solid rod portion 70 distal from the elbows 78. During operation of the device 10 and after completion of an injection, the indicator 190 is configured to align with the window 130 on the housing 12 to indicate at least partial completion of the injection. The indicator 190 preferably has a distinctive color or design to represent completion of an injection.

As shown in FIG. 8, the illustrative syringe actuation component 700' further includes a retaining flange 720' for holding the actuating coil spring 88 in a compressed position until actuation. The retaining flange 720' is sized, dimensioned and formed of a material that preferably allows the syringe actuation component 700' to slidably and easily move within the housing 12 when the device 10 is actuated. Extending distally from the retaining flange 720', the syringe actuation component 700' forms a base 788', for the actuating coil spring 88. The base 788' terminates in a trigger anchoring portion 789'. The illustrative base 788' may comprise flexible arms 788a', 788b' around which the spring 88 coils. The trigger anchoring portion 789' may comprise tabbed feet 7891' extending from the base 788' and configured to selectively engage the anchoring cap 12c and/or distal housing component 12b. The firing button 32 coupled to the distal end of the distal housing component 12b is configured to hold the trigger anchoring portion 789' until activation. When activated, the firing button 32 releases the trigger anchoring portion 789', allowing the coil spring 88 to propel the syringe actuation component 700' towards the proximal end 20 of the device 10 in an operation described above.

In a retracted, anchored position shown FIGS. 7 and 8 (corresponding to the schematic of FIG. 3), the trigger anchoring portion 789' interacts with the housing 12, which holds the tabbed feet 7891' in a latched position, against the biasing force of the coil spring 88, to maintain the syringe actuation component 700' in a retracted position. In this position, the flange 720' retracts the spring 88 against the back, distal wall 712' of the distal housing component 12b. An opening 713' in the anchoring cap 12c allows the firing button 32 access to the anchoring portion 789'. In the retracted position, the pressurizer 754' of the syringe actuation component 700' extends out of an opening 228 on the proximal end 122a of the distal housing component 12b. Also referring to FIG. 9, when the distal housing component 12b couples to a corresponding syringe actuation mechanism 121, the pressurizer 754' extends into the barrel portion of a syringe housed therein. The pressurizer 754' may be integral with, the same as, connected to, or otherwise in communication with the bung 54 of a syringe 50 housed in the device 10 and may have any suitable size, shape and configuration suitable for applying pressure to the bung 54. In one embodiment, the pressurizer 754' has a cross-section corresponding to the shape of the barrel portion 53 of a corresponding syringe 50 so as to substantially seal the barrel portion 53, and the pressurizer 754' is configured to slidably move within the barrel portion 53 to apply pressure to the bung 54 and actuate the syringe 50.

In the illustrative embodiment of FIGS. 7 and 8, the syringe actuation component 700' constitutes a single, integrated mechanism for anchoring a corresponding syringe 50, spring 88 and other components, actuating and moving the syringe 50 to a protracted position, and separately expelling the contents of the syringe 50.

Figure 9:
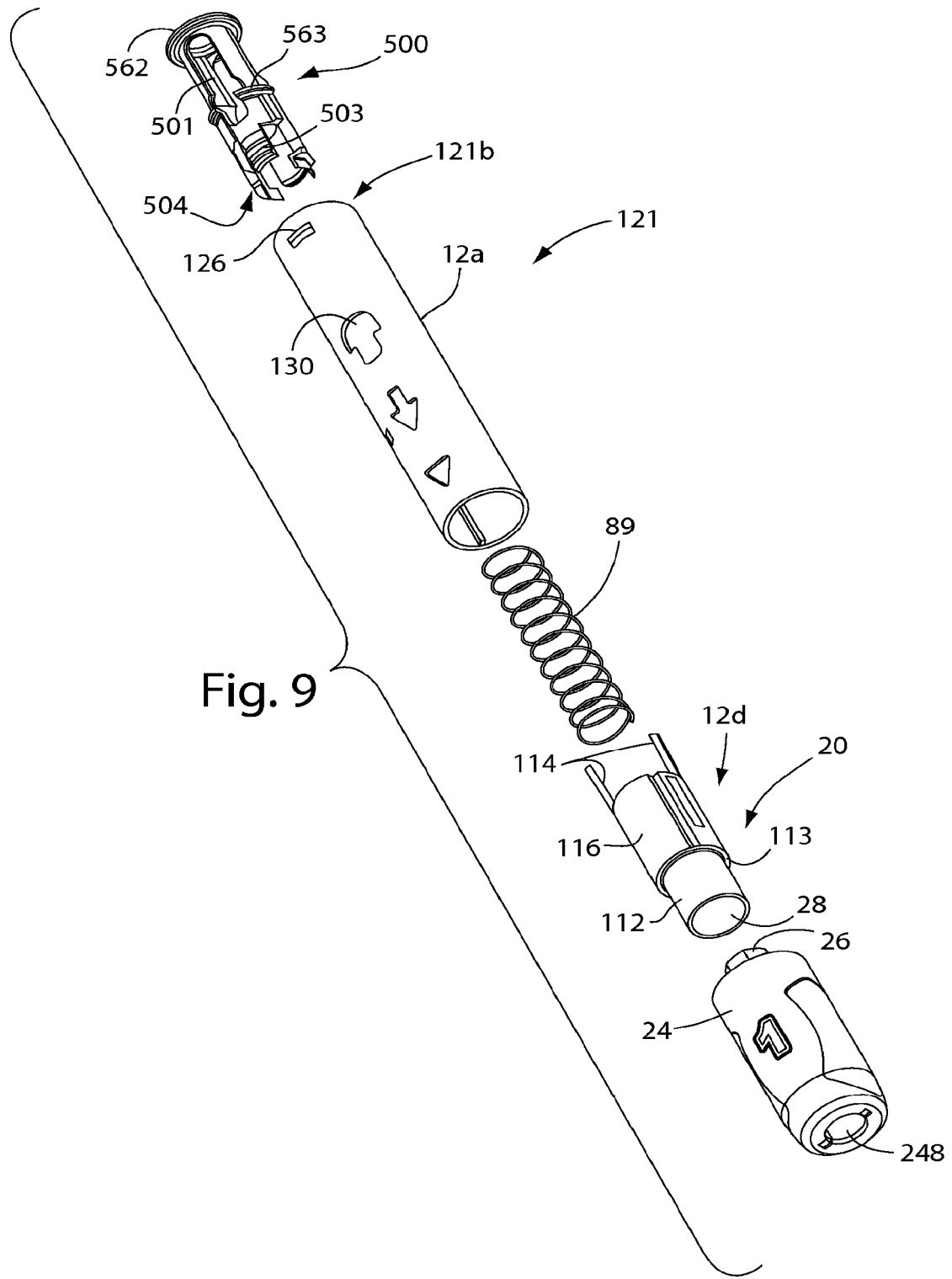
FIG. 9 illustrates a perspective view of the syringe housing assembly of the exemplary automatic injection device of FIG. 6.

FIG. 9 is an exploded view of the syringe housing assembly 121 of an illustrative embodiment of the invention, which is configured to couple to and interact with the FM assembly 122 of FIGS. 7 and 8. The illustrative syringe housing assembly 121 includes a proximal housing component 12a, the proximal cap 24, a proximal, second biasing mechanism 89, a syringe carrier 500 and a stepped shroud 12d forming a proximal portion 20 of the housing 12 when assembled and includes the proximal opening 28, as also shown in FIG. 2. The components 12a, 12d, 89, 500 and 24 cooperate to house a syringe 50 containing a substance to be injected and facilitate operation of the device 10 in the two different operational stages as described above.

Referring now to FIGS. 1, 2, and 9, the syringe carrier 500 of the illustrative embodiment envelopes the distal half of a syringe 50 used in the device 10. The syringe 50 rests in the carrier 500 and both are contained in the housing 12. During operation, the syringe 50 and the carrier 500 move forward (e.g., proximally) within the housing 12. The housing 12 stops and limits the movement of the carrier 500, and the carrier 500 in turn stops and limits the movement of the syringe 50. The illustrative syringe carrier 500 has a substantially tubular structure including window cutouts 501 preferably aligned with the window 130 on the housing 12a to allow a patient to view the contents of the syringe 50 prior to operation. The syringe carrier 500 may include a flanged distal end 562 configured to interface with a flanged distal end 56 (shown in FIG. 3) of the syringe 50. Referring to FIG. 9, the flanged distal end 562 may serve as a damper for the syringe 50. The syringe carrier 500 may further include an intermediate flange 563, which in the illustrative embodiment forms a stop for the syringe 50 that interacts with an interior stop 256 (shown in FIGS. 10A and 10B) on the proximal housing component 12a to limit forward motion of the syringe 50. Referring again to FIG. 9, the illustrative syringe carrier 500 may further include a proximal anchor portion 503 that limits movement of the syringe 50 in a distal, rearward direction. In the illustrative embodiment, the proximal anchor portion 503 includes a radial groove configured to engage the interior stop 256. A syringe carrier coupler 504 extends forward past the proximal anchor portion 503 to facilitate coupling of the syringe carrier 500 with the distal end of the spring 89 and the stepped shroud 12d. In one embodiment, the syringe carrier 500 is stationary within the housing 12 and the syringe 50 selectively and controllably slides within and relative to the syringe carrier 500. Alternatively, the syringe carrier 500 is slidably disposed within the housing 12 and selectively carries the syringe 50 within the housing 12. The syringe carrier 500 may have any suitable configuration and size suitable for carrying or guiding the syringe 50 within the housing 12.

Figure 10A:
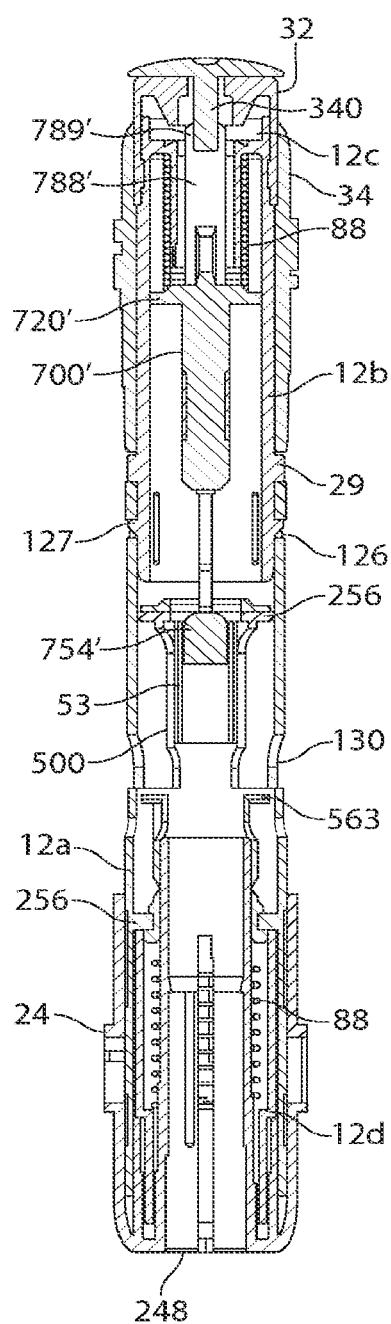
FIGS. 10A and 10B illustrate cross-sectional views of an exemplary assembled automatic injection device at 90° offset angles from each other, in which the syringe housing assembly and the firing mechanism assembly are coupled together, provided in accordance with exemplary embodiments.

Referring again to FIG. 9, the illustrative stepped shroud 12d forms a proximal end 20 of the housing 12. The illustrative stepped shroud 12d has a substantially tubular body, including a proximal boss 112 defining the proximal opening 28 of the device 10, through which the syringe needle 55 projects during operation of the device 10. A step 113 from the main tubular body portion 116 forms the proximal boss 112 of smaller diameter than the main tubular body portion 116 of the stepped shroud 12d. As shown in FIG. 10A, the step 113 forms a forward stop for the spring 89 to confine the spring 89 and prevent forward movement of the spring 89 towards the proximal end 20 of the device 10. In the illustrative embodiment, shown in FIG. 10A, the distal rim 115 of the stepped shroud 12d abuts the proximal side of the stop 256 of the proximal housing component 12a. Referring now to FIG. 9, distal arms 114 extend from the stepped shroud 12d to lock in the stepped shroud 12d to prevent accidental needle sticks.

Figure 10B:
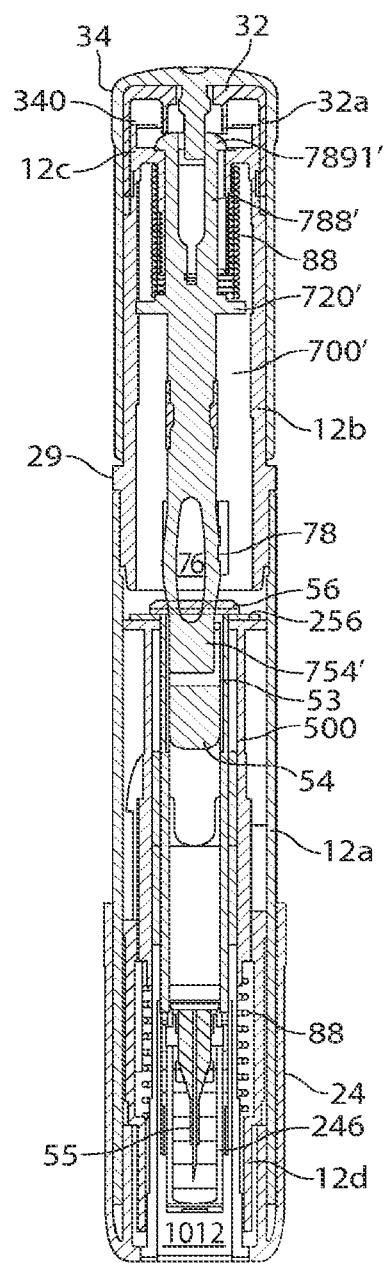

FIGS. 10A and 10B are cross-sectional views at 90° offset angles from each other, illustrating an assembled automatic injection device 10, wherein the syringe housing assembly 121 and a FM assembly 122 of FIG. 6 are coupled together, such that the pressurizer 754' of the syringe actuation component 700' extends into the barrel portion 53 of a syringe 50 housed in the syringe housing assembly 121 and in communication with a bung 54 of the syringe 50. Referring again to FIGS. 8 and 10B, the syringe actuation component 700' includes, at its proximal end 700a', a pressurizing end 754' for applying pressure to the bung 54, a plunger rod portion 70 with a compressible expanded portion 76 (illustrated as the plunger elbows 78), as well as other components, such as components for anchoring the coil spring 88 to the syringe actuation component 700', as described below. The compressible expanded portion 76 facilitates movement of a corresponding syringe 50 into a protracted position and expulsion of the contents of the syringe 50 in two separate steps, as described herein. Alternatively, the syringe actuation component 700' may comprise multiple actuators for moving and/or promoting expulsion of the syringe 50.

As shown, in FIG. 10B, the trigger anchoring portion 789' of the syringe actuation component 700' is anchored towards the distal end of the housing 12 by the firing button 32. When a patient depresses the firing button 32, driving arms 32a connected to the firing button 32 compress the tabbed feet 7891' of the trigger anchoring portion 789' inwards, thereby decreasing the distance (plunger arm width) between the tabbed feet of the plunger arms 788a', 788b', releasing the syringe actuation mechanism 700' and releasing the spring 88. Prior to operation, the compressible expanded portion 76, illustrated as elbows 78, of the syringe actuation component 700' rests above the flange 56 of the syringe 50 to allow the compressible expanded portion 76, when pushed by a released coil spring 88, to apply pressure to the syringe barrel portion 53, thereby moving the syringe 50 forward within the housing 12 when actuated. As described above, once a stop, such as a stop 256 on the proximal housing component 12a shown in FIG. 10B, catches the syringe 50 and halts additional forward motion of the projecting syringe 50, the continued biasing force on the spring 88 will continue to move the syringe actuation component 700' forward, causing the compressible expanded portion 76 to compress and move into the barrel portion 53 of the syringe 50. The forward motion of the syringe actuation component 700' within the barrel portion 53 causes the pressurizer 754' to apply pressure to the bung 54, causing expulsion of the syringe contents into an injection site.

As also shown in FIGS. 10A and 10B, the actuator cap 34 may include a stabilizing protrusion 340 that extends through the activator button 32 and between the feet tabbed 7891' of the syringe actuation component 700' to stabilize the components of the device prior to activation.

Figure 11A:
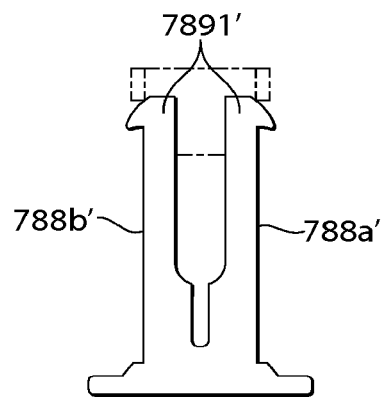
FIGS. 11A-11C illustrate cross-sectional views of the syringe actuation component of the firing mechanism assembly of FIG. 7, provided in accordance with exemplary embodiments, showing the position of the plunger arms at various stages of actuation.
Figure 11B:
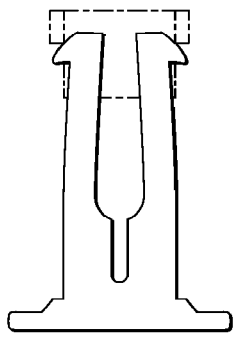
Figure 11C:
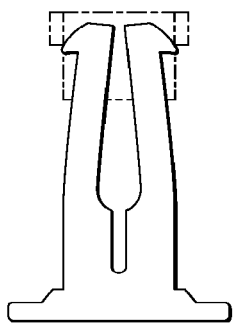

FIGS. 11A-11C illustrate cross-sectional views of the syringe actuation component of the firing mechanism assembly of FIG. 7, provided in accordance with exemplary embodiments, showing the position of the plunger arms at various stages of actuation. In FIG. 11A, the syringe actuation component 700' is preloaded by the first biasing mechanism 88 before actuation of the firing button. The plunger arms are spread apart with the plunger arm width being a first, larger width. In FIG. 11B, the plunger arms are pushed together at the start of actuation of the firing button. In FIG. 11C, the plunger is released during actuation of the firing button. The plunger arms are disposed closer to each other with the plunger arm width being a second, smaller width.

Figure 12:
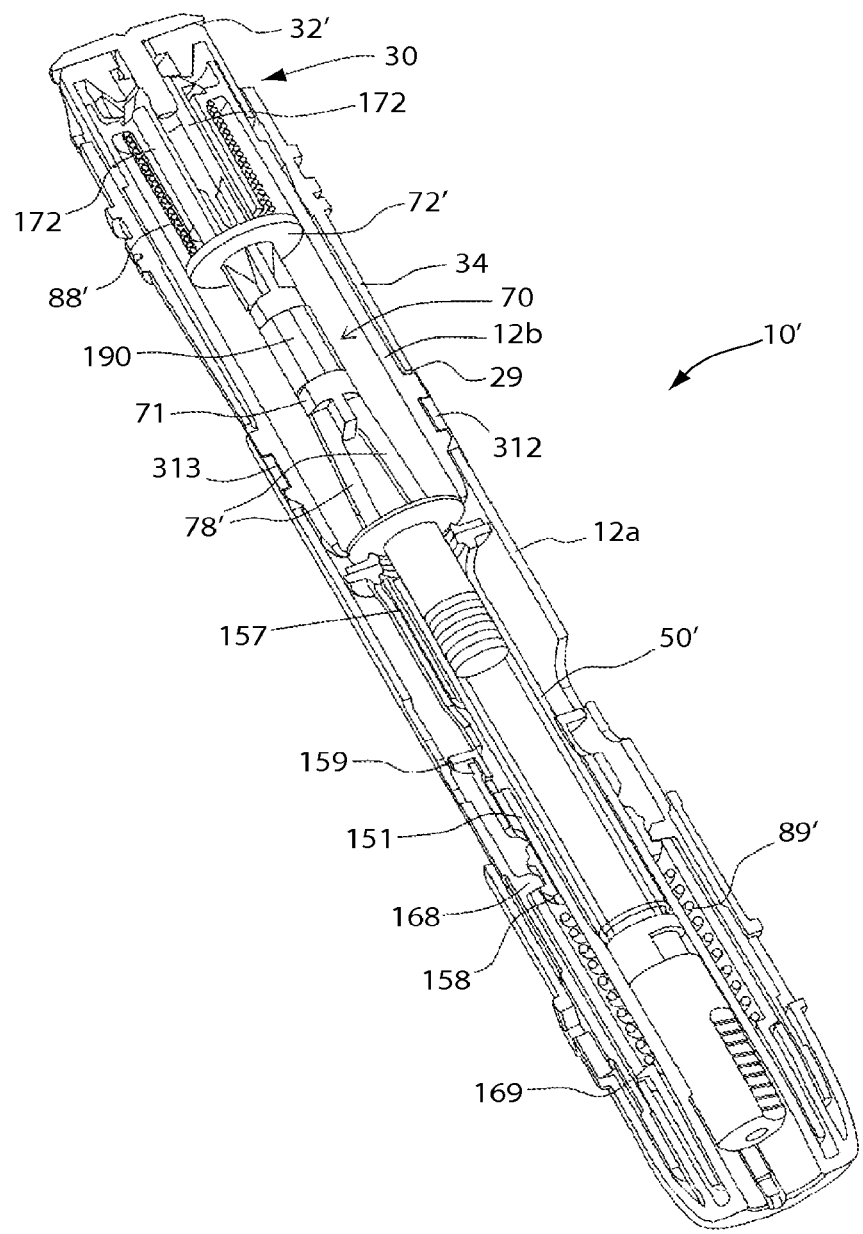
FIG. 12 illustrates a cross-sectional view of an exemplary automatic injection device, provided in accordance with exemplary embodiments.

FIG. 12 is a cross-sectional view of an assembled automatic injection device 10' according to an illustrative embodiment of the invention. The illustrative embodiment of the automatic injection device 10' includes two mating proximal and distal housing components 12a, 12b. The proximal and distal housing components 12a, 12b mate to form a complete housing 12. As shown, a proximal housing component 12a, forming a proximal end of the housing 12, receives a proximal end of the distal housing components 12b. A cooperating projection 312 and groove 313, or a plurality of cooperating projections 312 and grooves 313, facilitate mating of the proximal and distal housing components 12a, 12b in the illustrative embodiment. Other suitable mating mechanisms may alternatively be employed. A shelf 29 formed on an outer surface of the distal housing component 12b may form a stop for the second removable cap 34.

As shown, the firing button 32' may be a cap covering the distal end of the distal housing component 12b. The illustrative firing button 32' slides relative to the distal housing component 12b to actuate a syringe actuator, such as the plunger 70. The illustrative firing button 32' releasably retains flexible anchoring arms 172 of the plunger 70'. When depressed, the firing button 32' releases the flexible anchoring arms 172 to allow a first biasing mechanism, illustrated as spring 88' to propel the plunger 70' towards the proximal end of the device 10'.

In the embodiment of FIG. 12, the plunger 70' further includes a flange 72' located between the compressible expanded portion 78' and the distal end of the plunger rod 71'. A first biasing mechanism 88' is seated between an interior distal end of the housing 12 and the flange 72' to bias the plunger 70 towards the proximal end of the housing 12'. As described above, when the firing button 34' releases the anchoring arms 172, the coil spring 88', or other suitable biasing mechanism propels the plunger 70' towards the proximal end 20 of the device 10.

The illustrative embodiment 10' further includes an indicator 190 formed at an intermediate portion of the plunger rod 71' between the flange 72' and the compressible expanded portion 76, illustrated as flexible elbows 78'.

The syringe 50' of FIG. 12 may include protrusions or other suitable component to facilitate controlled movement of the syringe within the housing 12'. For example, with reference to FIG. 12, the syringe 50' includes a sleeve 157 forming a proximal protrusion 158 for abutting a proximal side of a first protrusion 168 formed on an inner surface of the housing 12' for limited movement of the syringe 50' in the distal direction within the housing 12'. The sleeve 157 may also form a flange 159 that may abut the distal side of the first protrusion 168 to limit movement of the syringe 50' in the proximal direction during an injection.

In the embodiment of FIG. 12, the second biasing mechanism, illustrated as coil spring 89' is disposed about a proximal portion of the syringe 50'. A shelf 169 formed at a proximal inner surface of the housing 12' receives a proximal end of the coil spring 89'. The proximal protrusion 158 of the syringe sleeve 157, or another suitably disposed mechanism, receives the distal end of the coil spring 89'. As described above, the second biasing mechanism 89' biases the syringe 50' in a retracted position within the housing 12' until activation of the device 10.

As shown in FIGS. 10A, 10B and 12, the automatic injection device 10' incorporates an indicator 190 to indicate to the patient of the device 10' when the dose from the syringe 50 has been fully or substantially fully ejected. In the illustrative embodiment, the indicator 190 is formed on a portion of the plunger rod 71' between the compressible expanded central portion 76 and the flange 72'. As the plunger rod 71 moves during operation, the indicator 190 advances towards and aligns with window 130 as the dose empties from the syringe. The indicator 190, which is preferably a different color or pattern from the substance being injected, fills the window 130 entirely to indicate that the dosage has been ejected. Any suitable indicator may be used.

After injection of the dose from the device 10' via the needle 55, a needle sheath 112, which may be formed by the proximal end 20 of the shroud 12d may automatically advance over the exposed needle 55 extending from the housing proximal end 20 to prevent accidental needle sticks.

The syringe actuation component 700', or distal portion thereof, may be composed at least partially of any suitable material, such as an acetal-based plastic, though other suitable materials may also be used. In exemplary embodiments, the syringe actuation component 700' may be made at least partially of a thermoplastic material or a thermosetting material.

Thermoplastic materials include polyacetal, polycarbonate, polyacrylate, polyamide, acryonitrile-butadiene-styrene (ABS), polyvinyl chloride (PVC) and their copolymers, terpolymers, and filled composites thereof. Polyacetal materials include acetal homopolymers, copolymers, and filled materials thereof. Hostaform C copolymer is an exemplary acetal polyoxymethylene (POM) copolymer. Acetal copolymers, e.g., Hostaform C copolymer, may be filled materials and may be glass sphere filled and glass fiber filled materials thereof.

Thermosetting materials include epoxy, acrylic, urethane, ester, vinyl ester, epoxy-polyester, acrylic-urethane, and fluorovinyl. In exemplary embodiments, acrylic materials may include a reactive functionality such as an acid and a hydroxyl. In an embodiment, the epoxy material includes a reactive functionality that can be cured by a method selected from the group consisting of visible, UV and thermal crosslinking. Exemplary thermosetting materials include, but are not limited to, different kinds of stereolithography resins that may be photopolymers (e.g., Somos 9420, protoGen O-XT 18420, Watershed 11120, DMX-SL100, Prototherm 12120, Nanoform 15120, Waterclear Ultra 10122, and ProtoCast AF 19120). In an embodiment, the thermosetting material is an epoxy homopolymer, copolymer or filled composite thereof.

In an exemplary embodiment, the material composing the syringe actuation component 700' may have a flex modulus of between about 1000 MPa and about 6000 MPa. In another exemplary embodiment, the material may have a flex modulus of between about 2000 MPa and about 5500 MPa. In another exemplary embodiment, the material may have a flex modulus of between about 3000 MPa and about 5000 MPa. In yet another exemplary embodiment, the material may have a flex modulus of about 3800 MPa.

Figure 13A:
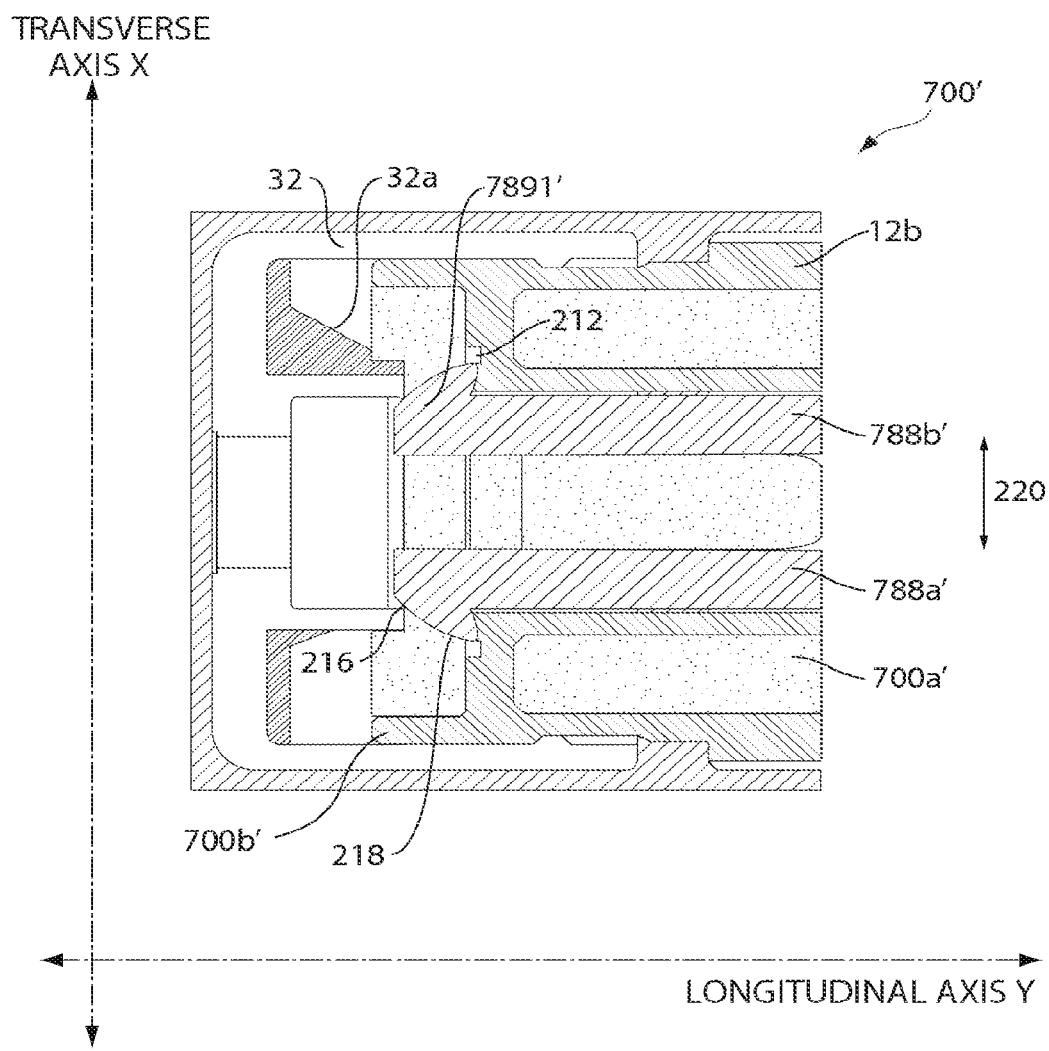
FIG. 13A illustrates a cross-sectional schematic view of the proximal end of the firing mechanism assembly of FIG. 7, provided in accordance with exemplary embodiments.

FIG. 13A illustrates a cross-sectional schematic view of a distal end 700b' of the syringe actuation component 700', i.e., the end disposed farther away from the bung 54. The distal end 700b' of the syringe actuation component 700' may be bifurcated into a pair of plunger arms 788a' and 788b'. Each plunger arm 788a', 788b' may have a tabbed foot 7891' at a distal end closest to the firing button 32. Along the longitudinal axis Y of the syringe actuation component 700', each tabbed foot 7891' may have a distal end 211 closest to the firing button 32 and a proximal end 213 farthest from the firing button 32. Each tabbed foot 7891' may have a top surface 215 disposed at the distal end 211 that is substantially flat along the transverse axis X of the syringe actuation component 700', and a bottom surface 219 disposed at the proximal end 213 that is substantially flat along the transverse axis X.

Each tabbed foot 7891' may have a first outer conical surface—initial contact surface (ICS) 216—formed between the top surface 215 and the secondary contact surface (SCS) 218 of the tabbed foot 7891' that is configured to initially contact the firing button 32. The ICS may form an angle—the ICS angle—relative to the longitudinal axis Y of the syringe actuation component 700'. In an exemplary embodiment, the ICS angle is between about 0° and about 90°. In another exemplary embodiment, the ICS angle is between about 40° and about 80°. In another exemplary embodiment, the ICS angle is about 28°. In yet another exemplary embodiment, the ICS angle is about 38°. In still another exemplary embodiment, the ICS angle is about 48°. The tabbed foot 7891' may have a first transition edge 217 formed between the top surface 215 and the ICS 216.

The tabbed foot 7891' may have a second outer conical surface—SCS 218—disposed between the ICS 216 and the bottom surface 219 of the tabbed foot 7891' that is configured to subsequently contact the firing button 32 after the firing button 32 has contacted the ICS 216. The SCS 218 may form an angle—the SCS angle—relative to the longitudinal axis Y. In an exemplary embodiment, the SCS angle is between about 0° and about 90°. In another exemplary embodiment, the SCS angle is between about 6° and about 38°. In another exemplary embodiment, the SCS angle is between about 8° and about 25°. The tabbed foot 7891' may have a second transition edge 221 disposed between the ICS 216 and the SCS 218, and a third transition edge 223 disposed between the SCS 218 and the bottom surface 219.

In an exemplary embodiment, a first contact surface is formed by the first outer conical surfaces ICS 216 of the two tabbed feet 7891' of the two plunger arms 788a' and 788b'. The first contact surface includes at least one open segment between the two plunger arms 788a' and 788b', such that the two ICS 216 are non-contiguous. A conical contact surface is formed by the second outer conical surfaces SCS 218 of the two tabbed feet 7891' of the two plunger arms 788a' and 788b'. The second contact surface includes at least one open segment between the two plunger arms 788a' and 788b', such that the two SCS 218 are non-contiguous. The first and second contact surfaces are configured to contact the firing button 32. The first contact surface makes initial contact with the firing button 32, and the second contact surface makes subsequent contact with the firing button 32 after the first contact surface has made initial contact with the firing button 32.

In an exemplary embodiment, the ICS and SCS angles may be different. In another exemplary embodiment, the ICS and SCS angles may be the same.

In an exemplary embodiment, the tabbed foot 7891' may have a third outer surface 225, which may or may not be conical. In exemplary embodiments including third outer surface 225, the SCS 218 is disposed between the ICS 216 and the third surface 225, and the third surface is disposed between the SCS 218 and the bottom surface 29 of the tabbed foot 7891'. The third surface 225 may be configured to contact the firing body 12b. The third surface 225 may form an angle—the protrusion angle—relative to the longitudinal axis Y. In an exemplary embodiment, the protrusion angle may range between about 0° and about 90°. In another exemplary embodiment, the protrusion angle may range between about 62° and about 82°. In another exemplary embodiment, the protrusion angle may range between about 65° and about 79°. In another exemplary embodiment, the protrusion angle may range between about 68° and about 76°.

The third surface 225 may project from and extend beyond the SCS 218 to a particular height—the protrusion height—as measured along the longitudinal axis Y. In an exemplary embodiment, the protrusion height ranges between about 0.17 mm and about 0.47 mm. In another exemplary embodiment, the protrusion height ranges between about 0.20 mm and about 0.42 mm. In another exemplary embodiment, the protrusion height ranges between about 0.23 mm and about 0.37 mm.

The firing body 12b may include a firing body conical surface (FBCS) 212 that is configured to contact the third outer surface 225. When the firing button 32 is pushed down, the contact between the third outer surface 225 and the FBCS 212 causes the plunger to move up slightly.

Figure 13B:
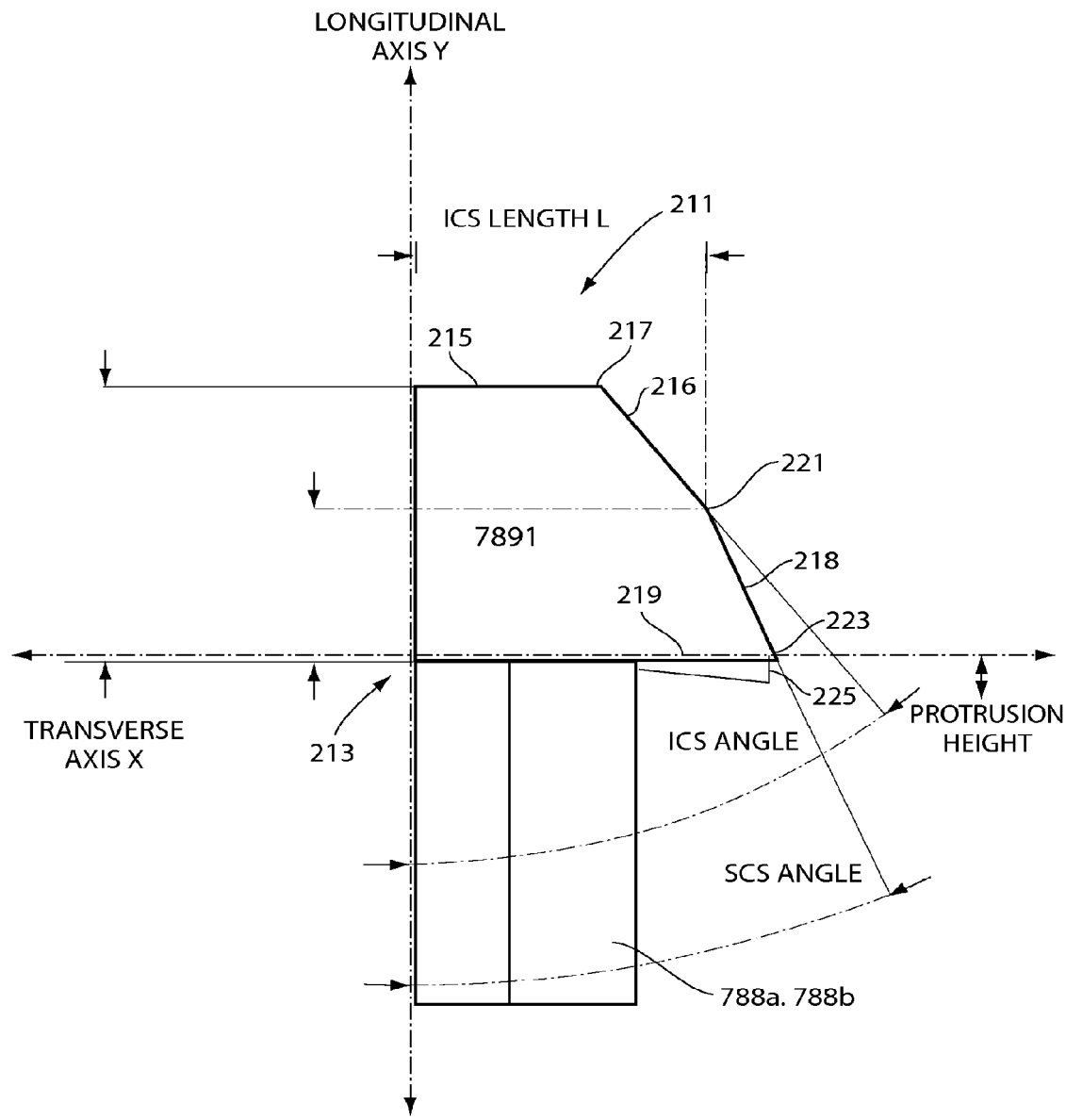
FIG. 13B illustrates a cross-sectional schematic outline of a plunger arm at the proximal end of the firing mechanism assembly of FIG. 13A, provided in accordance with exemplary embodiments.

FIG. 13B illustrates a cross-sectional schematic outline of a plunger arm 788a'/788b' disposed at the distal end 700b' of the syringe actuation component 700'. FIG. 13B also pictorially indicates the ICS angle, the SCS angle, and the ICS length L which is the length of the tabbed foot 7891' along the transverse axis X at its second transition edge 221 (ICS-SCS transition edge).

During activation of the firing mechanism assembly 122, the spring 88 which holds the plunger 70 in place does not move when the button 32 is pressed. The angle of the firing body 12*b* and the underside of the plunger 70 interact, while the firing button 32 and ICS 216 interact. The firing button 32 moves down along the longitudinal axis Y of the firing mechanism assembly, and the tabbed foot 7891' bends inward. When the tabbed foot 7891' enters the firing button 32, the plunger 70 collapses in a bending motion.

In an exemplary embodiment, the ICS angle is between about 40° and about 58°, about 38° and about 48°, about 38° and about 54°, about 38° and about 50°, or about 48° and about 58°. In another exemplary embodiment, the ICS angle is about 38°, about 48°, or about 58°. In another embodiment, the ICS angle is about 45°. Numbers intermediate to the recited ranges are also included in the invention.

In an exemplary embodiment, the ICS length is between about 2.64 mm and about 3.03 mm. In another exemplary embodiment, the ICS length is between about 2.84 mm and about 3.03 mm. In another exemplary embodiment, the ICS length is about 3.00 mm.

In an exemplary embodiment, the SCS angle is between about 9° and about 25°. In another exemplary embodiment, the SCS angle is about 9°. In another exemplary embodiment, the SCS angle is about 23°.

In an exemplary embodiment, one or more parameters of the syringe actuation component 700' are singly or cooperatively configured to improve the FtF. In an exemplary embodiment, for thermosetting materials, FtF may be improved by modifying one or more of the following parameters: a) flex modulus of the plunger material, b) ICS angle, c) ICS length, d) PBB angle, and e) plunger width. In another exemplary embodiment, for thermoplastic materials, FtF may be improved by modifying one or more of the following parameters: a) flex modulus of the plunger material and b) molding condition. In another exemplary embodiment, FtF may be improved by modifying the protrusion height and/or the protrusion angle.

In another exemplary embodiment, one or more of the following parameters are singly or cooperatively configured in various combinations to increase FtF: a) flex modulus of the plunger material, b) protrusion angle (PA) or protrusion height (PH), c) ICS angle, d) ICS length, and e) PBB angle. For example, such combinations can comprise altering two factors, such as: a) flex modulus and PA, b) flex modulus and ICS angle, c) flex modulus and ICS length, d) flex modulus and PBB angle, e) PA and ICS angle, f) PA and ICS length, g) PA and PBB angle, h) ICS angle and ICS length, i) ICS angle and PBB angle, and j) ICS length and PBB angle.

In another exemplary embodiment, such combinations can comprise altering three factors, such as: a) flex modulus, PA, and ICS angle, b) flex modulus, PA, and ICS length, c) flex modulus, PA, and PBB angle, d) flex modulus, ICS angle, and ICS length, e) flex modulus, ICS angle, and PBB angle, f) flex modulus, ICS length, and PBB angle, g) PA, ICS angle, and ICS length, h) PA, ICS angle, and PBB angle, i) PA, ICS length, and PBB angle, and j) ICS angle, ICS length, and PBB angle.

In another exemplary embodiment, such combinations can comprise altering four factors, such as, for example, a) flex modulus, PA, ICS angle, and ICS length, b) flex modulus, PA, ICS angle, and PBB angle, c) flex modulus, ICS angle, ICS length, and PBB angle, and d) PA, ICS angle, ICS length, and PBB angle.

In another exemplary embodiment, such combinations can comprise altering five factors, such as: flex modulus, PA, ICS angle, ICS length, and PBB angle. Exemplary ranges for these parameters can be found in Table 1.

Table 1 tabulates five exemplary factors associated with the plunger that may be varied, singly or in combination, to alter the FtF: flex modulus, PA, ICS angle, ICS length, and PBB angle. Table 1 summarizes exemplary ranges, preferred ranges and most preferred ranges of the five factors.

TABLE 1

Factors Configurable to Achieve Improved FtF

| Factor | Materials* Flex Modulus (MPa) | Protrusion Angle (°) | ICS Angle (°) | ICS Length (mm) | PBB Angle (°) |
|---|---|---|---|---|---|
| Range | 1,000-6,000 | 82-62 | 28-58 | 2.44-3.03 | 0.3-3.0 |
| Preferred Range | 2,000-5,500 | 79-65 | 33-54 | 2.64-3.03 | 0.4-2.5 |
| Most Preferred Range | 3,000-5,000 | 76-68 | 34-50 | 2.84-3.03 | 0.5-2.0 |

In an exemplary embodiment, the width 220 between the plunger arms 788*a'*, 788*b'* (plunger arm width) is between about 2.55 mm and about 3.45 mm. In another exemplary embodiment, the plunger arm width 220 is between about 2.55 mm and about 5.15 mm. In another exemplary embodiment, the plunger arm width 220 is between about 2.55 mm and about 4.25 mm. In another exemplary embodiment, the plunger arm width 220 is between about 2.85 mm and about 3.45 mm. In another exemplary embodiment, the plunger arm width 220 is about 3.05 mm.

Substances for Use in Exemplary Automatic Injection Devices

The methods and compositions of the invention can be used with automatic injection devices that administer essentially any substance or medication that is suitable for administration by injection. Typically, the substance or medication will be in a fluid, e.g., liquid form, although medications in other forms such as gels or semi-solids, slurries, particulate solutions, etc. also may suitable for use if the automatic injection device is designed to permit the administration of such forms of the medication.

Preferred medications are biological agents, such as antibodies, cytokines, vaccines, fusion proteins and growth factors. Methods of making antibodies are described above.

Non-limiting examples of other biological agents that can be used as the medication in the automatic injection device include but are not limited to antibodies to or antagonists of human cytokines or growth factors, for example, TNF, LT, IL-1, IL-2, IL-3, IL-4, IL-5, IL-6, IL-7, IL-8, IL-15, IL-16, IL-18, IL-21, IL-23, interferons, EMAP-II, GM-CSF, FGF, and PDGF; antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD 154 (gp39 or CD40L); TNFα converting enzyme (TACE) inhibitors; IL-1 inhibitors (Interleukin-1-converting enzyme inhibitors, IL-1RA etc.); Interleukin 11; IL-18 antagonists including IL-18 antibodies or soluble IL-18 receptors, or IL-18 binding proteins; non-depleting anti-CD4 inhibitors; antagonists of the co-stimulatory pathway CD80 (B7.1) or CD86 (B7.2) including antibodies, soluble receptors or antagonistic ligands; agents which interfere with signaling by proinflammatory cytokines such as TNFα or IL-1 (e.g. IRAK, NIK, IKK, p38 or MAP kinase inhibitors); IL-1β converting enzyme (ICE)

inhibitors; T-cell signaling inhibitors such as kinase inhibitors; metalloproteinase inhibitors; angiotensin converting enzyme inhibitors; soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R); antiinflammatory cytokines (e.g. IL-4, IL-10, IL-11, IL-13 and TGF-beta); Rituximab; IL-1 TRAP; MRA; CTLA4-Ig; IL-18 BP; anti-IL-18; anti-IL15; IDEC-CE9.1/SB 210396 (non-depleting primatized anti-CD4 antibody; IDEC/SmithKline; see e.g., Arthritis & Rheumatism (1995) Vol. 38; S185); DAB 486-IL-2 and/or DAB 389-IL-2 (IL-2 fusion proteins; Seragen; see e.g., Arthritis & Rheumatism (1993) Vol. 36; 1223); Anti-Tac (humanized anti-IL-2Ra; Protein Design Labs/Roche); IL-4 (anti-inflammatory cytokine; DNAX/Schering); IL-10 (SCH 52000; recombinant IL-10, anti-inflammatory cytokine; DNAX/Schering); IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., Arthritis & Rheumatism (1996) 39(9, supplement); S284; Amer. J. Physiol.—Heart and Circulatory Physiology (1995) 268:37-42); R973401 (phosphodiesterase Type IV inhibitor; see e.g., Arthritis & Rheumatism (1996) 39(9, supplement); S282); MK-966 (COX-2 Inhibitor; see e.g., Arthritis & Rheumatism (1996) 39(9, supplement); S81); Iloprost (see e.g., Arthritis & Rheumatism (1996) 39(9, supplement); S82); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); TNF-convertase inhibitors; anti-IL-12 antibodies; anti-IL-18 antibodies; interleukin-11 (see e.g., Arthritis & Rheumatism (1996) 39(9, supplement), S296); interleukin-13 (see e.g., Arthritis & Rheumatism (1996) 39(9, supplement), S308); interleukin-17 inhibitors (see e.g., Arthritis & Rheumatism (1996) 39(9, supplement), S120); anti-thymocyte globulin; anti-CD4 antibodies; CD5-toxins; ICAM-1 antisense phosphorothioate oligo-deoxynucleotides (ISIS 2302; Isis Pharmaceuticals, Inc.); soluble complement receptor 1 (TP10; T Cell Sciences, Inc.); and anti-IL2R antibodies.

TNFα Inhibitors for Use in Exemplary Embodiments

According to one embodiment of the invention, the illustrative automatic injection device may be used to deliver a dose of a TNF inhibitor used to treat arthritis and other diseases. In one embodiment, the solution contained in the syringe contains 40 or 80 milligrams of drug product (TNFα blocker or inhibitor)/1 mL, for example, 40 or 80 mg adalimumab, 4.93 mg sodium chloride, 0.69 mg monobasic sodium phosphate dehydrate, 1.22 mg dibasic sodium phosphate dehydrate, 0.24 mg sodium citrate, 1.04 mg citric acid monohydrate, 9.6 mg mannitol, 0.8 mg polysorbate 50 and water for injection, with USP sodium hydroxide added as necessary to adjust pH to be about 5.2.

The present invention can be used to administer a dose of a substance, such as a liquid drug, e.g., a TNFα inhibitor, to a patient. In one embodiment, the dose delivered by the automatic injection device of the invention comprises a human TNFα antibody, or antigen-binding portion thereof.

In one embodiment, the TNF inhibitor used in the methods and compositions of the invention includes isolated human antibodies, or antigen-binding portions thereof, that bind to human TNFα with high affinity and a low off rate, and have a high neutralizing capacity. Preferably, the human antibodies of the invention are recombinant, neutralizing human anti-hTNFα antibodies, such as, e.g., the recombinant, neutralizing antibody referred to as D2E7, also referred to as HUMIRA® or adalimumab (Abbott Laboratories; the amino acid sequence of the D2E7 VL region is shown in SEQ ID NO: 1 of U.S. Pat. No. 6,090,382 the amino acid sequence of the D2E7 VH region is shown in SEQ ID NO: 2 of U.S. Pat. No. 6,090,382). Properties of D2E7 have been described in Salfeld et al., U.S. Pat. Nos. 6,090,382, 6,258,562, and 6,509,015. Other examples of TNFα inhibitors include chimeric and humanized murine anti-hTNFα antibodies that have undergone clinical testing for treatment of rheumatoid arthritis (see e.g., Elliott et al. (1994) Lancet 344:1125-1127; Elliot et al. (1994) Lancet 344:1105-1110; and Rankin et al. (1995) Br. J. Rheumatol. 34:334-342).

An anti-TNFα antibody (also referred to herein as a TNFα antibody), or an antigen-binding fragment thereof, includes chimeric, humanized, and human antibodies. Examples of TNFα antibodies that may be used in the invention include, but not limited to, infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), and CNTO 148 (golimumab; Medarex and Centocor, see WO 02/12502). Additional TNF antibodies that may be used in the invention are described in U.S. Pat. Nos. 6,593,458; 6,498,237; 6,451,983; and 6,448,380.

Other examples of TNFα inhibitors which may be used in the methods and compositions of the invention include etanercept (Enbrel, described in WO 91/03553 and WO 09/406476), soluble TNF receptor Type I, a pegylated soluble TNF receptor Type I (PEGs TNF-R1), p55TNFR1gG (Lenercept), and recombinant TNF binding protein (r-TBP-I) (Serono).

In one embodiment, exemplary embodiments provide improved uses and compositions for treating a disorder in which TNFα is detrimental, e.g., rheumatoid arthritis, with a TNFα inhibitor, e.g., a human TNFα antibody, or an antigen-binding portion thereof, through an automatic injection device.

A TNFα inhibitor includes any agent (or substance) that interferes with TNFα activity. In a preferred embodiment, the TNFα inhibitor can neutralize TNFα activity, particularly detrimental TNFα activity which is associated with disorders in which TNFα activity is detrimental, including, but not limited to, rheumatoid arthritis, juvenile rheumatoid arthritis, ankylosing spondylitis, Crohn's disease, psoriasis, and psoriatic arthritis.

Pharmaceutical Compositions

Pharmaceutical compositions may be loaded into the automatic injection device of the invention for delivery to a patient. In one embodiment, antibodies, antibody-portions, as well as other TNFα inhibitors, can be incorporated into pharmaceutical compositions suitable for administration to a patient using the device of the invention. Typically, the pharmaceutical composition comprises an antibody, antibody portion, or other TNFα inhibitor, and a pharmaceutically acceptable carrier. "Pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody, antibody portion, or other TNFα inhibitor.

The compositions for use in the methods and compositions of the invention may be in a variety of forms in accordance with administration via the device of the invention, including, for example, liquid solutions (e.g., injectable and infusible solutions), dispersions or suspensions. In a preferred embodiment, the antibody or other TNFα inhibitor is administered by subcutaneous injection using the device of the invention. In one embodiment, the patient administers the TNFα inhibitor, including, but not limited to, TNFα antibody, or antigen-binding portion thereof, to himself/herself using the device of the invention Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody, antibody portion, or other TNFα inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, exemplary embodiments provide an automatic injection device, e.g., autoinjector pen, comprising an effective TNFα inhibitor and a pharmaceutically acceptable carrier. Thus, the invention provides a prefilled automatic injection device comprising a TNFα inhibitor.

In one embodiment, the antibody or antibody portion for use in the methods of the invention is incorporated into a pharmaceutical formulation as described in PCT/IB03/04502 and U.S. Patent Publication No. 2004/0033228. This formulation includes a concentration 50 mg/ml of the antibody D2E7 (adalimumab), wherein an automatic injection device contains 40 mg of antibody for subcutaneous injection. In one embodiment, the automatic injection device of the invention (or more specifically the syringe of the device) comprises a formulation of adalimumab having the following formula: adalimumab, sodium chloride, monobasic sodium phosphate dihydrate, dibasic sodium phosphate dihydrate, sodium citrate, citric acid monohydrate, mannitol, polysorbate 80 and water, e.g., water for injection. In another embodiment, the automatic injection device comprises a volume of adalimumab including 40 mg adalimumab, 4.93 mg sodium chloride, 0.69 mg monobasic sodium phosphate dihydrate, 1.22 mg dibasic sodium phosphate dihydrate, 0.24 mg sodium citrate, 1.04 mg citric acid monohydrate, 9.6 mg mannitol, 0.8 mg polysorbate 80 and water, e.g., water for injection. In one embodiment, sodium hydroxide is added as necessary to adjust pH.

The dose amount of TNFα inhibitor in the automatic injection device may vary according to the disorder for which the TNFα inhibitor is being used to treat. In one embodiment, the invention includes an automatic injection device comprising a dose of adalimumab of about 20 mg of adalimumab; 40 mg of adalimumab; 80 mg of adalimumab; and 160 mg of adalimumab. It should be noted that for all ranges described herein, including the dose ranges, all numbers intermediary to the recited values are included in the invention, e.g., 36 mg of adalimumab, 48 mg of adalimumab, etc. In addition ranges recited using said numbers are also included, e.g. 40 to 80 mg of adalimumab. The numbers recited herein are not intended to limit the scope of the invention.

The TNFα antibodies and inhibitors used in the invention may also be administered in the form of protein crystal formulations that include a combination of protein crystals encapsulated within a polymeric carrier to form coated particles. The coated particles of the protein crystal formulation may have a spherical morphology and be microspheres of up to 500 micro meters in diameter or they may have some other morphology and be microparticulates. The enhanced concentration of protein crystals allows the antibody of the invention to be delivered subcutaneously. In one embodiment, the TNFα antibodies of the invention are delivered via a protein delivery system, wherein one or more of a protein crystal formulation or composition, is administered to a patient with a TNFα-related disorder. Compositions and methods of preparing stabilized formulations of whole antibody crystals or antibody fragment crystals are also described in WO 02/072636, which is incorporated by reference herein. In one embodiment, a formulation comprising the crystallized antibody fragments described in PCT/IB03/04502 and U.S. Patent Publication No. 2004/0033228 is used to treat rheumatoid arthritis using the methods of the invention.

Supplementary active compounds can also be incorporated into the compositions. In certain embodiments, an antibody or antibody portion for use in the methods of the invention is coformulated with and/or co-administered with one or more additional therapeutic agents, including a rheumatoid arthritis inhibitor or antagonist. For example, an anti-hTNFα antibody or antibody portion may be coformulated and/or co-administered with one or more additional antibodies that bind other targets associated with TNFα related disorders (e.g., antibodies that bind other cytokines or that bind cell surface molecules), one or more cytokines, soluble TNFα receptor (see e.g., PCT Publication No. WO 94/06476) and/or one or more chemical agents that inhibit hTNFα production or activity (such as cyclohexane-ylidene derivatives as described in PCT Publication No. WO 93/19751) or any combination thereof. Furthermore, one or more antibodies of the invention may be used in combination with two or more of the foregoing therapeutic agents. Such combination therapies may advantageously utilize lower dosages of the administered therapeutic agents, thus avoiding possible side effects, complications or low level of response by the patient associated with the various monotherapies. Additional agents that may be used in combination with a TNFα antibody or antibody portion are described in U.S. application Ser. No. 11/800,531, which is incorporated in its entirety herein.

Devices of the invention and methods for making and using same are described in more detail below in the following examples.

EXEMPLIFICATION

Plungers provided by exemplary embodiments were compared against various control plungers to determine the structural, functional and operational characteristics of the plungers that affect the FtF of an automatic injection device. Exemplary embodiments provide methods for determining the FtF of an automatic injection device, testing factors that affect the FtF of an automatic injection device, determining how to modulate the FtF by configuring such factors, and improving the FtF in a device by configuring such factors. Exemplary embodiments also provide systems for determining the FtF of an automatic injection device, testing factors that affect the FtF of an automatic injection device, and improving the FtF in a device by configuring such factors. Exemplary embodiments provide automatic injection devices having one or more features that have been configured, singly or in combination, to improve the FtF required to fire the devices.

Methods and Materials

Exemplary plungers discussed herein are composed at least partly of acetal polyoxymethylene (POM) copolymers, e.g., from Ticona, Hostaform C 13031, unless otherwise stated. Exemplary plungers may also be composed of other thermoplastic and thermosetting materials are provided herein below in Tables 2 and 3.

Table 2 tabulates different thermoplastic materials that may be used to make exemplary plungers, the vendors of the materials, the material grades, the material densities, the melt volumes, the tensile modulus, and the flex modulus. The tensile modulus is a measure of the stiffness of the material, and the flex modulus is a measure of the tendency of the material to bend.

Additional Hostaform grades of polyacetal beyond Table 2, sourced from: http://tools.ticona.com/tools/mcbasei/product-tools.php?sPolymer=POM&sProduct=HOSTAFORM and http://love8ff.diytrade.com/sdp/450410/4/pd-2493053/3735737-1249560.html include, but are not limited to, HOSTAFORM AM90S, HOSTAFORM AM90S Plus, HOSTAFORM C 13021, HOSTAFORM C 13021 RM, HOSTAFORM C 13031, HOSTAFORM C 13031 K, HOSTAFORM C 13031 XF, HOSTAFORM C 2521, HOSTAFORM C 2521 G, HOSTAFORM C 2552, HOSTAFORM C 27021, HOSTAFORM C 27021 AST, HOSTAFORM C 27021 GV3/30, HOSTAFORM C 52021, HOSTAFORM C 9021. HOSTAFORM C 9021 10/1570, HOSTAFORM C 9021 AW, HOSTAFORM C 9021 G, HOSTAFORM C 9021 GV1/10, HOSTAFORM C 9021 GV1/20, HOSTAFORM C 9021 GV1/20 XGM, HOSTAFORM C 9021 GV1/30, HOSTAFORM C 9021 GV1/30 GT, HOSTAFORM C 9021 GV3/10, HOSTAFORM C 9021 GV3/20, HOSTAFORM C 9021 GV3/30, HOSTAFORM C 9021 GV3/30 TF2, HOSTAFORM C 9021 K, HOSTAFORM C 9021 M, HOSTAFORM C 9021 SW, HOSTAFORM C 9021 TF, HOSTAFORM C 9021 TF5, HOSTAFORM C 9021 XAP®, HOSTAFORM CP15X, HOSTAFORM EC140CF10, HOSTAFORM EC140XF (POM), HOSTAFORM EC270TX, HOSTAFORM FK 1:25, HOSTAFORM FK 2:25, HOSTAFORM LM140LG, HOSTAFORM LM140LGZ, HOSTAFORM LM25, HOSTAFORM LM90, HOSTAFORM LU-02XAP®, HOSTAFORM LW15EWX, HOSTAFORM LW90BSX, HOSTAFORM LW90EWX, HOSTAFORM M15HP, HOSTAFORM M25AE, HOSTAFORM M90XAP®, HOSTAFORM MR130ACS, HOSTAFORM MT12R01, HOSTAFORM MT12U01, HOSTAFORM MT12U03, HOSTAFORM MT24F01, HOSTAFORM

TABLE 2

Exemplary Thermoplastic Materials

| Material ID | Vendor | Grade | Density (mg/cm$^3$) | Melt Volume Rate (cm$^3$/10 minutes) | Tensile Modulus (Psi × 10$^5$/MPa) (ISO 527-2/1°) | Flex Modulus (Psi × 10$^5$/MPa) (ISO 178) |
|---|---|---|---|---|---|---|
| 1 | Ticona | Hostaform C 13031 (copolymer) | 1.41 | 12 | 4.42/3,050 | 4.35/3,000 |
| 2 | Ticona | Hostaform C 27021 GV3/30 (30% glass spheres) | 1.59 | 16 | 5.50/3,800 | 5.07/3,500 |
| 3 | Ticona | Hostaform C 9021 GV3/20 (20% glass spheres) | 1.53 | 8.5 | 4.93/3,400 | 4.64/3,200 |
| 4 | Ticona | Hostaform C 9021 GV3/10 (10% glass spheres) | 1.47 | 9.0 | 4.50/3,100 | 4.35/3,000 |
| 5 | Ticona | Hostaform C 9021 GV1/30 (30% glass fibers) | 1.60 | 4.0 | 13.35/9,200 | |
| 6 | Ticona | Hostaform C 9021 GV1/20 (20% glass fibers) | 1.57 | 4.5 | 10.45/7,200 | |
| 7 | Ticona | Hostaform C 9021 GV1/10 (10% glass fibers) | 1.48 | 6.0 | 6.97/4,800 | |

MT24U01, HOSTAFORM MT8F01, HOSTAFORM MT8F02, HOSTAFORM MT8R02, HOSTAFORM MT8U01, HOSTAFORM S 27063, HOSTAFORM S 27064, HOSTAFORM S 27072 WS 10/1570, HOSTAFORM S 9063, HOSTAFORM S 9064, HOSTAFORM S 9243, HOSTAFORM S 9244, HOSTAFORM S 9364, HOSTAFORM TF-10XAP®, and HOSTAFORM WR140LG.

Table 3 tabulates different thermosetting materials that may be used to make exemplary plungers and their flex moduli, as measured, for example, per ASTM D790M (sourced from www.DSMSOMOS.com). The flex modulus is a measure of the tendency of the material to bend. The flex moduli of plungers produced from the resins identified in Table 3 depend, in part, on the production resolution as well as type and level of curing, and, therefore, may vary and are reflected in the ranges provided.

TABLE 3

Exemplary Thermosetting Materials

| Material (derived from DSM Somos which is an epoxy based material) | Flex Modulus (MPa)* by ASTM D790M |
|---|---|
| Somos 9420 | 810 (768-900) |
| ProtoGen O-XT 18420 | 2060 (1990-2130) |
| Watershed 11120 | 2200 (2040-2370) |
| DMX-SL100 | 2290 (2282-2298) |
| ProtoTherm 12120 | 3320 (3060-3320) |
| Nanoform 15120 | 3630 (3630-4450) |
| Somos 8110 Epoxy Photopolymer | 310 |
| Somos 8120 Epoxy Photopolymer | 690 |
| Somos 9110 Epoxy Photopolymer | 1450 |
| Somos 9120 Epoxy Photopolymer | 1310-1455 |
| WaterShed 11110 | 2140 |
| Somos 14120 White | 2250 |
| ProtoTherm 12110 | 3350 |
| ProtoCast AF 19120 | 2430 |
| NanoTool | 10,500 |

A force tester may be used to determine the FtF of an automatic injection device. Before determining the FtF, the Firing Mechanism (FM) subassembly of the automatic injection device may be disassembled and the original plunger removed. An exemplary plunger may be assembled into the FM with the other components from the disassembled FM. A stopper may be inserted into the syringe with the aid of a hollow metal tube (where the stopper is within the hollow tube and then pushed down) to the desired position to stay at a pre-set (height) location in the syringe. The syringe may be inserted into a syringe housing subassembly. The housing and FM subassemblies may be assembled into an automatic injection device. In this way, the complete automatic injection device may be assembled with an exemplary plunger instead of the original plunger.

A force tester, e.g., a Zwick force tester, may be used to measure the FtF. First, a test, e.g., a PUSH Suitability Test, may be run to confirm that the force tester was measuring the force correctly. Then, the actual FtF test may be run. For this test, two specific fixtures may be used in the force tester. One fixture may hold the automatic injection device in a vertical position. The other fixture may be a disc that may be used to push down on the firing button of the automatic injection device. The fixture to hold the automatic injection device may be attached to the bottom part of the force tester machine, while the disc may be attached to the top part. Once these fixtures are assembled on the force tester machine, the automatic injection devices and the force tester may be ready for the FtF test.

During the force testing, caps 24 and 34 may be removed from the automatic injection device 10, and the automatic injection device may be placed into the automatic injection device holder fixture with the firing button 32 facing up. The device 10 may be locked into place in this fixture so that every automatic injection device tested may be placed at the same level in the fixture. The automatic injection device 10 may be placed in this fixture with the firing button 32 facing up.

When the FtF test is started, the disc may begin to move down and push the firing button 32. In an example, the distance that the firing button is pushed down may be specified at typically 2.4 mm. When the program is initiated, the force tester machine may start to record the force that was experienced by the load cell sensors of the machine. A force graph may be plotted for the distance that the firing button is pushed down. The minimum force required to fire the automatic injection device may be read from the force graph and was defined as the FtF.

The method may be run automatically and the data may be displayed on the screen of the tester. When the method is complete, the automatic injection device may be removed from the fixtures. If analyzing multiple syringes within a single test series, the above steps may be repeated for each automatic injection device tested.

Conventional automatic injection devices can prematurely activate (fire) if the FtF is below a first optimal level. Some patients are not able to activate conventional automatic injection devices when the FtF is over a second optimal level. Exemplary devices and methods overcome this problem by providing automatic injection devices with an improved FtF and methods of making and using the same, as described herein.

Exemplary embodiments identify one or more parameters that may be configured, singly or in combination, in a plunger that is used in the firing mechanism of an automatic injection device. An increased FtF (e.g., over 5 N) may be achieved by configuring, for example, the ICS angle, molding conditions, or resin material, or any combination thereof. In one embodiment, the FtF of the firing mechanism of the automatic injection device ranges from greater than 5 N, about 10 N to about 25 N, or about 10 N to about 20 N, based on the use of a modified plunger. It should be noted that all numbers included in the range of FtF described herein are also intended as part of exemplary embodiments, e.g., 6 N, 7 N, 8 N, 9 N, 10 N, 11 N, 12 N, 13 N, 14 N, 15 N, 16 N, 17 N, 18 N, 19 N, 20 N, 21 N, 22 N, 23 N, 24 N, 25 N, and so forth. Ranges including the numbers recited herein are also included as part of exemplary embodiments for the FtF, e.g., about 6 N to about 19 N. A number of additional controllable factors may be configured to increase or decrease the FtF, e.g., molding conditions of the plunger (mold temperature and cooling time).

Each of the above controllable factors may have its own weight function for increasing FtF. The weight function of a given factor on FtF may be dependent on the flex modulus of the plunger material. For example, the effect of the ICS angle on FtF may be more pronounced when a plunger is made of a higher-modulus material than that of a plunger made of a lower-modulus material. An example of weight functions is: FtF=a(ICS angle)+b(ICS length), where "a" is the weight function of ICS angle and "b" is the weight function of ICS length, wherein both "a" and "b" are dependent on plunger material modulus.

Example 1

Relationship Between Plunger Arm Width and FtF

An exemplary plunger in an exemplary firing mechanism assembly may be bifurcated into two plunger arms. During activation of the firing mechanism, the firing button may move downwardly. As it moves downward, the firing button may exert pressure against portions of the plunger arms that contact the firing button, causing the plunger arms to deform and move toward each other.

The plunger arm width is the distance between the plunger arms. The plunger arm width may affect the minimum force required to activate the firing mechanism so that a substance is expelled from the syringe into the patient's body. As such, the plunger arm width may have an effect on the FtF of a firing mechanism assembly.

A study was designed to determine the relationship between the plunger arm width and the FtF. In a control plunger, the plunger arm width was about 3.05 mm. A baseline study was performed on ten control plungers that were assembled into firing mechanism and syringe housings. Results show that the control plungers had an FtF of between about 8.3 N and about 11.7 N, with an average FtF of about 10.2 N.

Figure 14A:
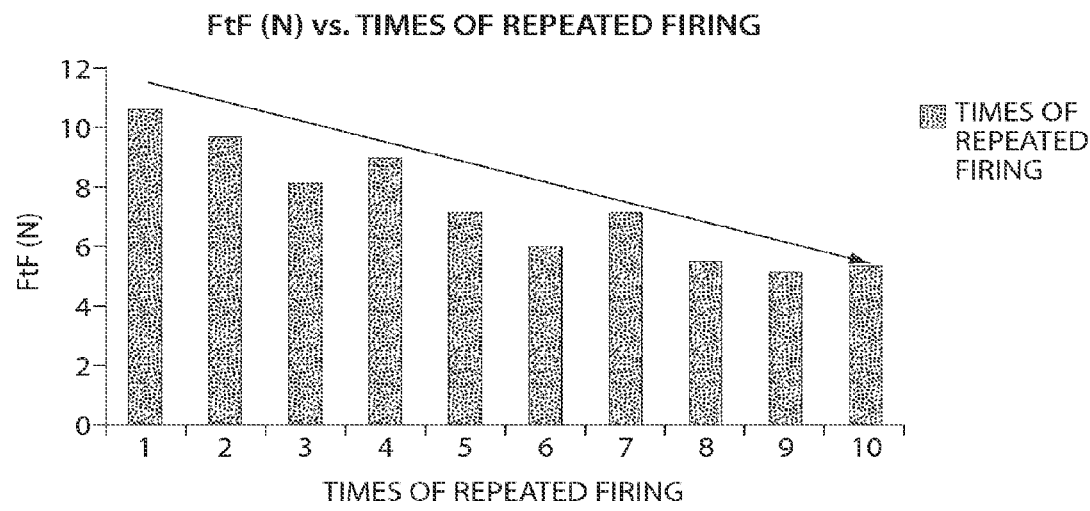
FIG. 14A shows a graph of FtF of a first syringe actuation component after firing the plunger ten times.
Figure 14B:
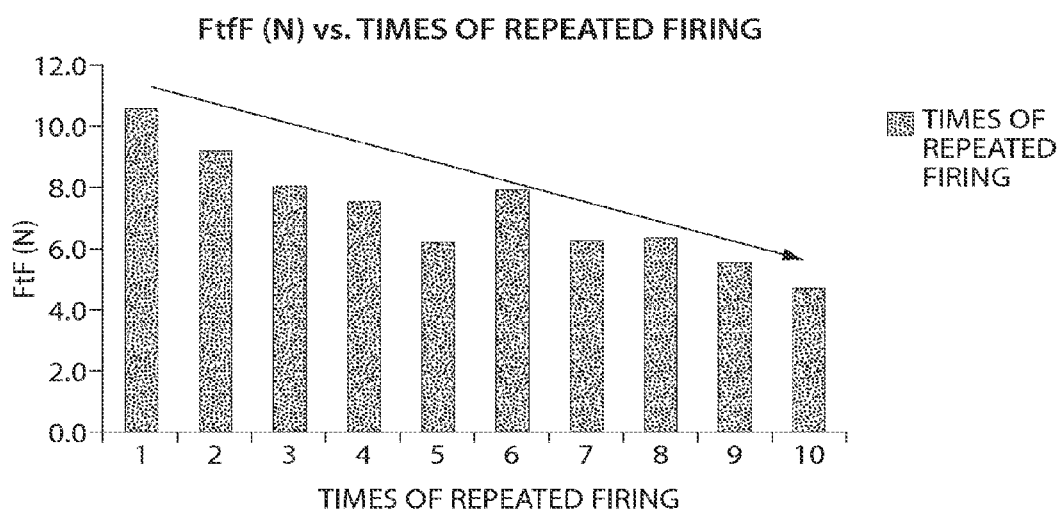
FIG. 14B shows a graph of FtF of a second syringe actuation component after firing the plunger ten times.

The plunger arm width was modulated using different methods. The effect of modifying the number of repeated firings on FtF was tested. The object of the following study was to explore whether modifying the plunger arm width, by changing the number of repeated firings, would affect the FtF. FIG. 14A shows a graph of FtF of a first syringe actuation component after firing the plunger ten times. FIG. 14B shows a graph of FtF of a second syringe actuation component after firing the plunger ten times. Results indicate that, for a given plunger, the FtF decreases with repeated firing.

Figure 15:
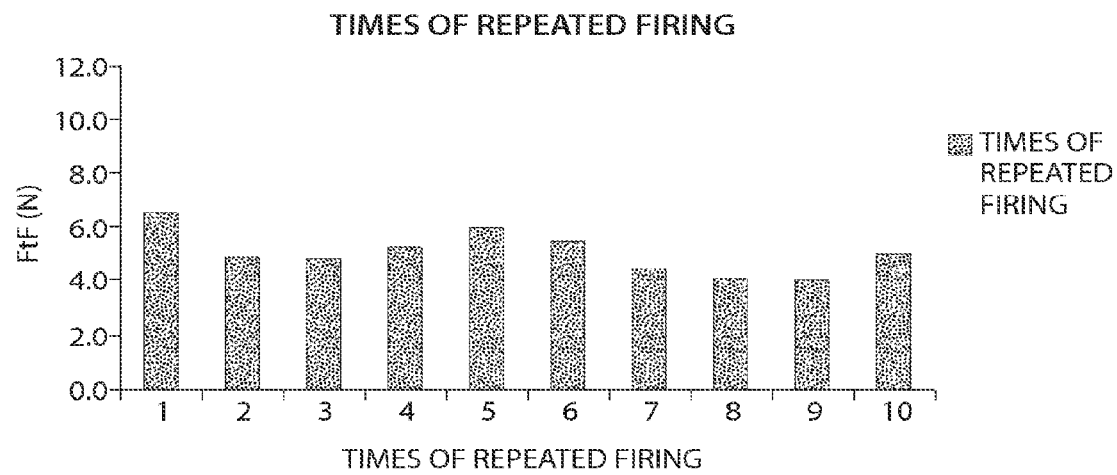
FIG. 15 shows a graph of FtF of a syringe actuation component after firing the plunger ten times after five days of assembly (i.e., exposure to spring force).

The object of the following study was to explore whether modifying the plunger arm width would affect the FtF. Certain plungers were re-assembled into a firing mechanism assembly and stored for five days (i.e., under the spring pulling force condition of the device). The firing mechanism was then fired ten times. FIG. 15 shows a graph of FtF of a syringe actuation component after firing the plunger ten times after five days of assembly (i.e., exposure to spring force). Results indicate that the FtF remains lower after 5 days exposure to the spring force and remains low after reassembly (about 4.1 N to about 6.5 N), with an average of about 5.1 N.

The effect of modifying molding conditions for molding the plunger on FtF was tested. The object of the following study was to explore whether modifying the plunger arm width, by changing the molding conditions, would affect the FtF of the plunger. Molding the plunger under certain conditions increases the width between the plunger arms which, in turn, is found to increase the FtF.

The effect of modifying the plunger arm width on FtF was tested. The plunger arm width was widened from a starting point of about 2.55-3.05 mm to about 5 mm during oven heating at 60° C. for three days. The other components of the firing mechanism (e.g., firing body and firing button) were not heated. After heating, the two plunger arms were not parallel but were opened outwards after removal from the oven. The width between the arms was measured at about 5 mm (compared to an unheated control plunger which had a plunger arm width of about 3 mm). Results show that the FtF increased to about 8.3-9.6 N, with an average of about 9.0 N, as the plunger arms width was widened to about 5 mm as compared to the control plunger.

Figure 16:
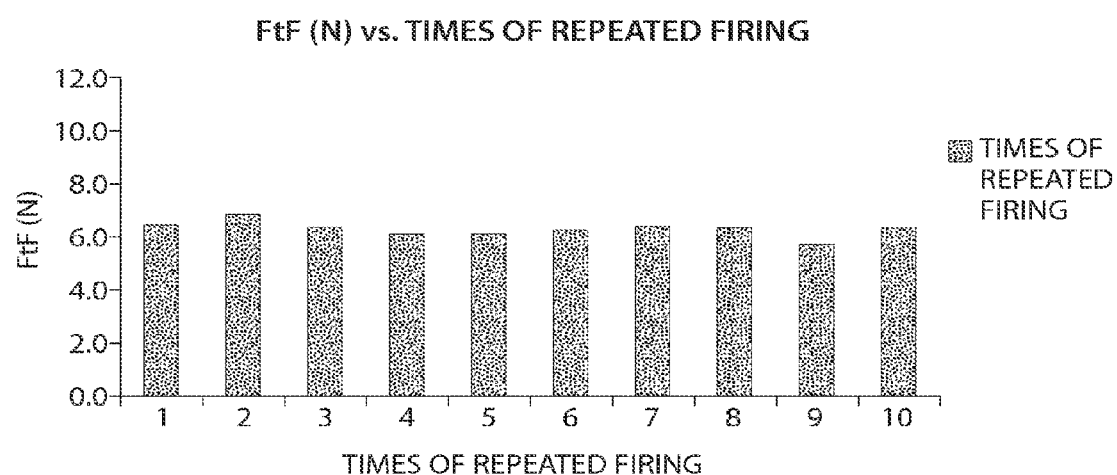
FIG. 16 shows a graph of FtF of a syringe actuation component after firing the plunger ten times after being reassembled for three days.

Certain plungers were oven conditioned, reassembled into a firing mechanism, and a spring force applied on the plungers for three days before FtF testing. The width between the plunger arms was noted to have reduced to about 3.5 mm from about 5 mm width. FIG. 16 shows a graph of FtF of a syringe actuation component after firing the plunger ten times after being reassembled for three days. Results indicate that this reduced the arms' width and resulted in a lower FtF (about 5.8 N to about 6.9 N).

Exemplary embodiments provide a method to configure a plunger in a firing mechanism assembly to achieve an improved FtF by modifying the plunger arm width. In an exemplary embodiment, the plunger is configured to have a large plunger arm width to achieve a higher FtF. In another exemplary embodiment, the plunger is configured to have a small plunger arm width to achieve a lower FtF. The plunger arm width may be increased to increase the FtF, and decreased to decrease the FtF.

Exemplary embodiments provide automatic injection devices in which the plunger arm width in the firing mechanism assembly is configured, singly or in combination with other factors, to improve the FtF. In an exemplary embodiment, the plunger arm width is about 5.0 mm.

The object of the following study was to explore whether increasing the plunger arm width, by changing the molding conditions and/or using a higher flex modulus material, would increase the FtF. The goal of the study was also to achieve an improved FtF while not changing the overall design of the device. This goal was attained by using a modified set of molding parameters and/or a higher flex modulus material of new resin grades. By altering the molding parameters and/or using a different type of resin grade, an improved plunger was created having an improved FtF.

Two different polyacetal (POM) resin grades were studied, i.e., an unfilled resin grade (3,050 MPa; control plunger) and a filled resin grade (30% sphere grade glass-sphere-filled; 3,800 MPa). Molding conditions for exemplary plungers included 100° F./25 seconds (mold temperature/cooling time) using the filled resin (3,800 MPa). Control molding conditions tested included 200° F./10 seconds (mold temperature/cooling time) using the unfilled resin grade (3,050 MPa). The plunger arm width was measured following molding. There was no design change in this study with respect to the ICS angle, which was kept at about 38°.

Analysis of the various resin and molding conditions reveal that plunger arm width increases as both the cooling time increased and the mold temperature is reduced. The plunger FtF increases with an increase in the plunger arm width, and also increases with a longer cooling time with a lower mold temperature. Results also reveal that the plunger FtF increases as the resin material modulus increases. FtF values increase 76% from about 7.68 N to about 13.52 N based on the combination of both an increased resin material modulus and modified molding process parameters.

Table 4 summaries the FtF achieved for different combinations of resin material grades of the plunger material and molding conditions of the plunger. More specifically, Table 4 compares the control plunger (Hostaform C 13031 copolymer) to the 30% sphere filled resin material under both control molding conditions and an alternative molding condition, i.e., 100° F./25 seconds. As described in Table 4, FtF increases with an increase in plunger arm width. In addition, a plunger with the filled resin had a higher FtF (plunger material modulus (filled grade) increased) than the control plunger with a lower modulus.

TABLE 4

Relationship between FtF and Combinations of Resign Material Grade and Molding Condition

| Materials/ Conditions | Width (mm) Hostaform C 13031 (control) | Width (mm) Hostaform C 27021 (30% sphere-filled) | FtF (N) Hostaform C 13031 (control) | FtF (N) Hostaform C 27021 (30% sphere-filled) |
|---|---|---|---|---|
| 200 F./10 sec | 2.49 | 2.88 | 7.68 | 12.06 |
| 100 F./25 sec | 3.07 | 3.15 | 10.68 | 13.52 |
| % Increase | 23% | 9% | 39% | 12% |

Ten percent glass fiber-filled resin (modulus at about 4,800 MPa), used under the two molding conditions described in Table 4, increases the FtF relative to the control at the given molding parameters (about 8.1 N at 200° F./10 seconds and about 10.4 N at 110° F./25 seconds). Two other molding conditions, i.e., about 100° F./10 seconds (mold temperature/cooling time) and about 200° F./25 seconds (mold temperature/cooling time) using the filled resin (3,800 MPa) also result in increases in the FtF.

In sum, FtF may be increased by configuring the molding conditions and the flex modulus of the plunger material. The above experiments also reveal that the plunger arm width may be increased in accordance with certain molding conditions and/or flex moduli. Thus, FtF may be modified without altering the ICS angle of the plunger.

Example 2

Relationship Between ICS Angle and FtF

An exemplary plunger arm in an exemplary firing mechanism assembly may have a head portion that includes a tabbed foot. The ICS is a portion of the plunger arm head that is configured to contact a firing engagement mechanism, e.g., a firing button. The ICS angle is the angle formed by the ICS with the longitudinal axis of the plunger.

During activation of the firing mechanism, the firing button may move downwardly. As it moves downward, the firing button may exert pressure against the ICS, causing the plunger arms to deform and move toward each other. The ICS angle may affect the minimum force required to activate the firing mechanism so that a substance is expelled from the syringe into the patient's body. As such, the ICS angle may have an effect on the FtF of a firing mechanism assembly.

Figure 17:
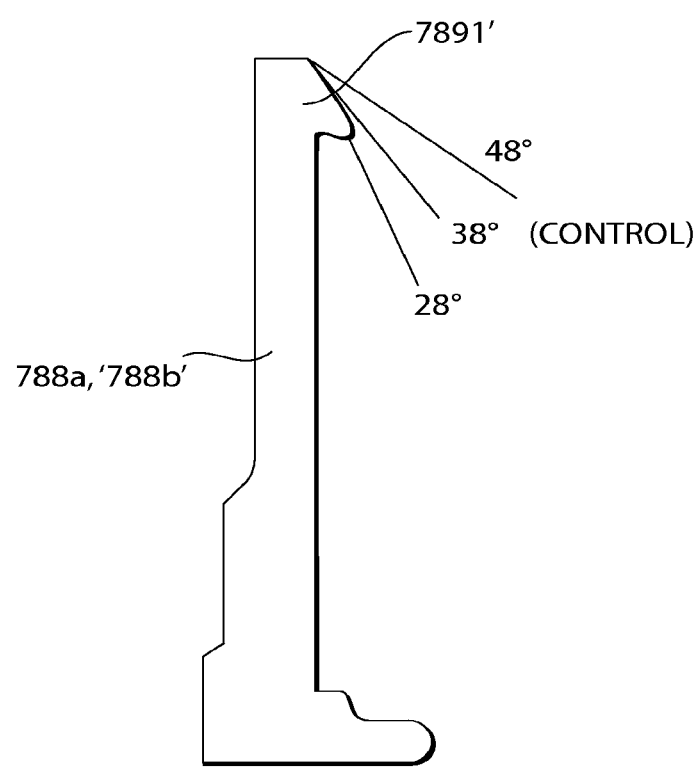
FIG. 17 illustrates a side view of a plunger arm of the syringe actuation component, provided in accordance with exemplary embodiments, showing three exemplary ICS angles.

A study was designed to determine the relationship between the ICS angle and the FtF. In a first set of experiments, a volume of glue was placed on top of the tabbed foot in various amounts and at various positions such that the ICS angle (a reversely sloped conical surface) was altered. The slope of the tabbed foot was altered from that of a control plunger with an ICS angle of 38° to four different ICS angles. The resultant slopes of the tabbed foot were as follows: glued plunger (d) (lowest ICS angle)<original plunger (a)<glued plunger (e)<glued plunger (b)<glued plunger (c) (highest ICS angle). FIG. 17 illustrates a side view of a plunger arm of the syringe actuation component, provided in accordance with exemplary embodiments, showing three exemplary ICS angles (28°, 38° as in the control plunger, 48°). The FtF was measured for each plunger according using a force tester.

Table 5 tabulates the FtF measurements for exemplary plungers.

TABLE 5

FtF Measurements for Different Glued Plungers

| Plunger Source | FtF (N) |
|---|---|
| Original Plunger (a) | 2.5 |
| Original Plunger (a) | 4.3 |
| Original Plunger (a) | 7.0 |
| Original Plunger (a) | 5.5 |
| Glued Plunger (b) | 29.4 |
| Glued Plunger (c) | 40.3 |
| Glued Plunger (c) | 44.3 |
| Glued Plunger (d) | 3.7 |
| Glued Plunger (e) | 21.5 |

Results show that the FtF was lowest at about 3.7 N for glued plunger (d) which had the lowest ICS angle, second lowest at an average of about 4.8 N for the control plunger (a) which had the second lowest ICS angle, third lowest at about 21.5 N for the glued plunger (e) which had the third lowest ICS angle, second highest at about 29.4 N for the glued plunger (b) with the second highest ICS angle, and highest at an average of about 42.3 N for the glued plunger (c) with the highest ICS angle.

In summary, results demonstrate that the higher the ICS angle of the tabbed foot, the higher the FtF. Thus, the ICS angle of the tabbed foot may be configured to control the FtF and to achieve an improved FtF.

In a second set of experiments, plungers were redesigned by software, e.g., 3D CAD software (Solidworks, Concord, Mass.), to achieve different ICS angles. Exemplary ICS angles were about 28° and about 48° as compared with the control plunger having an ICS angle of about 38°. The plungers were created using thermosetting materials 11120 and 12120. FtF as measured as compared to the 38° ICS angle of the control plunger comprised of a polyacetal (polyoxymethylene; POM) copolymer, e.g., Hostaform C 13031. The 11120 plunger had a flex modulus of about 2200 MPa, and the 12120 plunger had a flex modulus of about 3320 MPa, as compared to the control plunger which had a flex modulus of 3,000 MPa.

Figure 18:
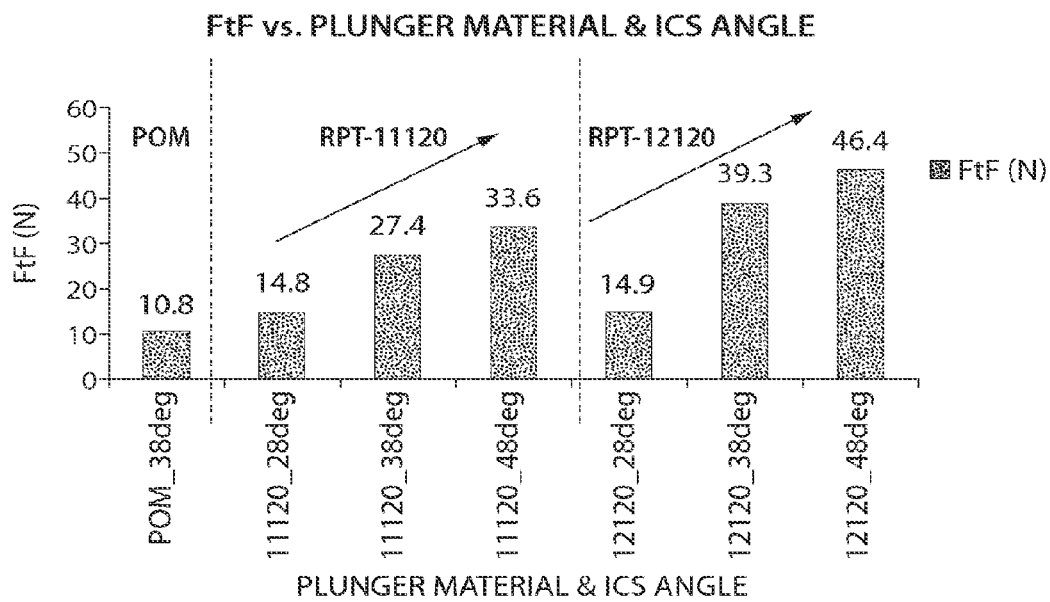
FIG. 18 shows a graph of the average FtF of plungers having various ICS angles (28°, 38°, 48°) and composed of various polymeric materials.

FIG. 18 shows a graph of the average FtF of plungers having various ICS angles (28°, 38°, 48°) and composed of various materials (POM, 11120, and 12120). FtF increases with increase in ICS angle as well as increase in the flex modulus, regardless of the material grades used for plunger production (e.g., grades 11120 and 12120). For the polyacetal (POM) plunger having an ICS angle of 38°, the FtF was about 10.8 N. For the 11120 plunger, the FtF was about 14.8 N, 27.4 N and 38.1 N for ICS angles of about 28°, 38° and 48°, respectively. For the 12120 plunger, the FtF was about 14.9 N, 39.3 N and 49.2 N for ICS angles of about 28°, 38° and 48°, respectively.

Figure 19:
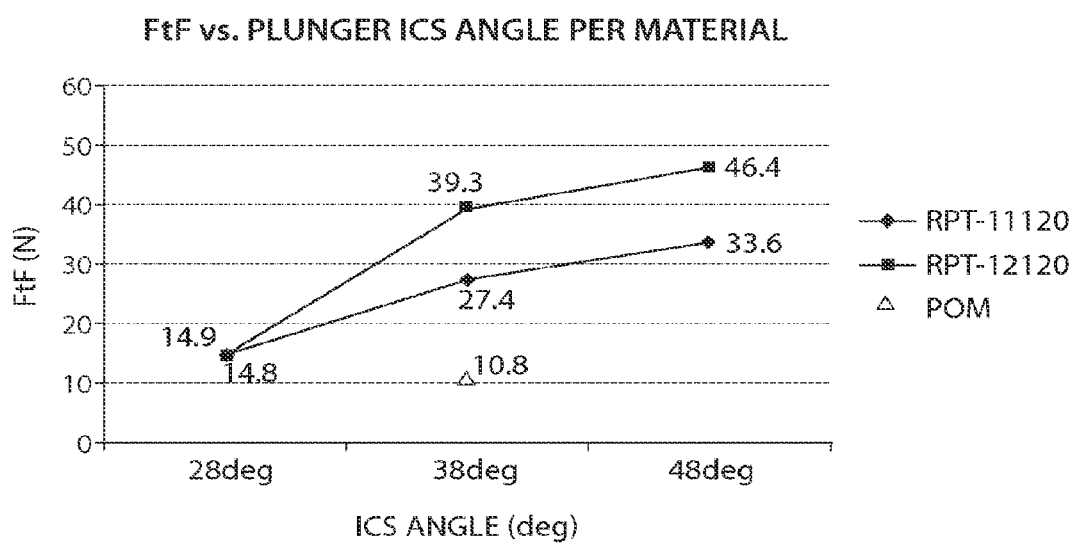
FIG. 19 shows a graph of the average FtF of plungers having various ICS angles (28°, 38°, 48°) and composed of various polymeric materials.

FIG. 19 shows a graph of the average FtF of plungers having various ICS angles (28°, 38°, 48°) and materials (POM, 11120, and 12120). The FtF for the 12120 plunger was increased by 24 N by changing the ICS angle from about 28° to 38°, and increased another 10 N by increasing the ICS angle by another 10°. Likewise, the FtF for the 11120 plunger was increased by about 13 N by changing the ICS angle from 28° to 38°, and increased another 10 N by increasing the ICS angle by about another 10°. Thus, a high flex modulus material (grade 12120) had an increased FtF over that of a lower modulus material (grade 11120), for the same ICS angles. The increase became more pronounced when the ICS angle was over 38°. In addition, the weight function of ICS angle on FtF changes with the plunger material modulus.

Thus, the ICS angle may be configured to control the FtF and to achieve an optimal FtF.

Exemplary embodiments provide a method to configure a plunger in a firing mechanism assembly to achieve an improved FtF by modifying the ICS angle. In an exemplary embodiment, the plunger is configured to have a large ICS angle (e.g., larger than 38°) to achieve a higher FtF. In another exemplary embodiment, the plunger is configured to have a small ICS angle (e.g., smaller than 38°) to achieve a lower FtF. The ICS angle may be increased to increase the FtF, and decreased to decrease the FtF. Exemplary embodiments also provide a method to configure a plunger in a firing mechanism assembly to achieve an improved FtF by modifying a combination of the ICS angle and the flex modulus of the plunger material.

Exemplary embodiments provide automatic injection devices in which the ICS angle is configured to improve the FtF. In an exemplary embodiment, the ICS angle is about 48°.

Example 3

Relationship Between Plunger Material and FtF

The plunger in an exemplary firing mechanism assembly may be composed at least partly of a specific plunger material. In an exemplary embodiment, the plunger material may be a thermoplastic material. In another exemplary embodiment, the plunger material may be a thermosetting material.

During activation of the firing mechanism, the firing button may move downwardly. As it moves downward, the firing button may exert pressure against the portions of the plunger arms that contact the firing button, causing the plunger arms to deform and move toward each other. The flex modulus of a material is the ratio of stress to strain in flexural deformation of the material, and determines the tendency of the material to bend under stress. The flex modulus may modulate how the plunger arms deform during activation of the firing mechanism and, in turn, affect the minimum force required to activate the firing mechanism so that a substance is expelled from the syringe into the patient's body. More specifically, if a plunger is composed of a higher flex modulus material, a higher force may be required to bend the plunger's arms, increasing the FtF.

Figure 20:
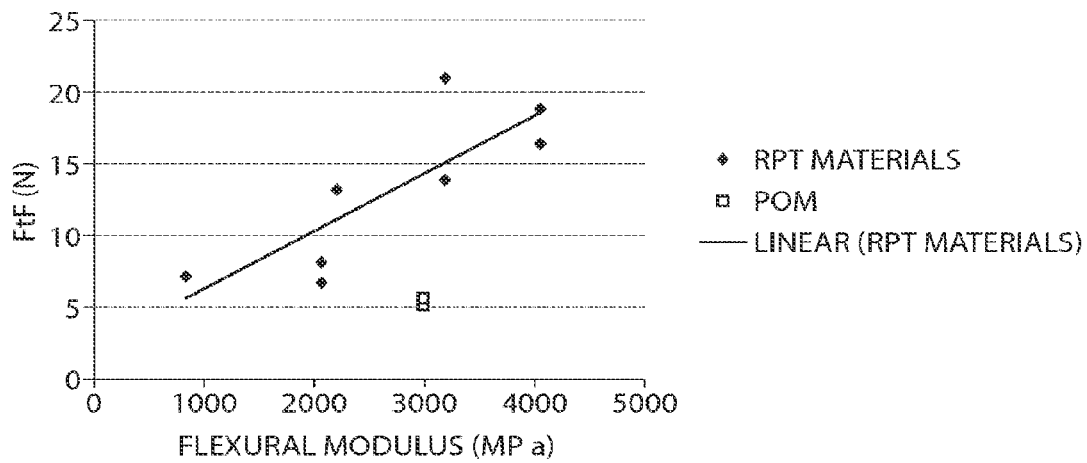
FIG. 20 shows a graph of the average FtF of the plungers composed of various polymeric materials.

A study was designed to determine the relationship between the flex modulus of the plunger material and the FtF. Different plunger materials having different flex moduli (9420, 18420, 11120, 12120, 15120, which are described in Table 3) were tested. The plungers all had a constant ICS angle of about 38°. FIG. 20 shows a graph of the average FtF of the plungers. Results of the study demonstrate that FtF increases with increasing flex moduli of the plunger material. Plungers that were made of resins with higher flex moduli result in higher FtFs than plungers that were made of resins with lower flexural moduli.

Exemplary embodiments provide a method to configure a plunger in a firing mechanism assembly to achieve an improved FtF by modifying the flex modulus of the plunger material. In an exemplary embodiment, the plunger is composed of a material with a high flex modulus to achieve a higher FtF. In another exemplary embodiment, the plunger is composed of a material with a low flex modulus to achieve a lower FtF. The plunger material can be changed to a higher flex modulus material to increase the FtF, and to a lower flex modulus material to decrease the FtF. Exemplary embodiments also provide automatic injection devices in which the flex modulus of the plunger material is configured, singly or in combination with other factors, to improve the FtF.

A further study was performed to determine if changing the plunger material flex modulus affected the time required to eject all the substance from the syringe. In the study, syringes filled with 0.8 mL of buffer were assembled into syringe housing subassemblies. The syringe housing subassemblies including syringes and the firing mechanism subassemblies including plungers were assembled into automatic injection devices. Tape was used to mimic skin for injection. For each device, the needle of the device was placed onto the tape to mimic an injection. The firing button and a stop watch were pressed at the same time at the start of the mimicked injection. The time required for the ejection of the entire substance in the syringe was recorded.

Figure 21:
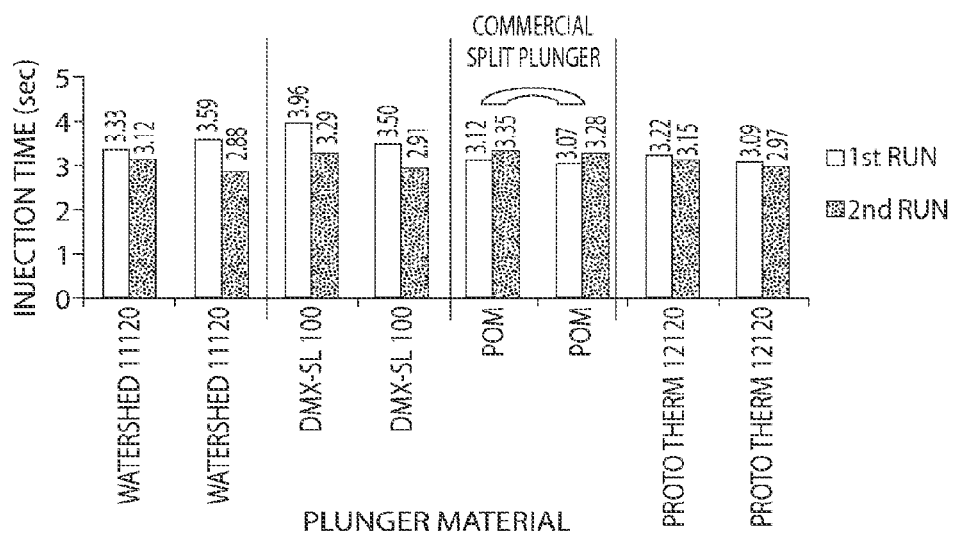
FIG. 21 shows a graph of the ejection times recorded for plungers composed of various polymeric materials having different flex moduli.

FIG. 21 shows a graph of the ejection times recorded for plungers composed of various materials having different flex moduli (11120, DMX-SL100, POM, and 12120 Prototherm). All exemplary plungers (having a wide range of modulus) had substantially the same ejection time. The results indicate that dispense, ejection or injection time of 0.8 mL of the substance remained substantially the same regardless of the flex modulus of the plunger material.

Example 4

Relationship Between Plunger Surface Texture and FtF

The head surfaces of the plunger arms in an exemplary firing mechanism assembly may have a particular surface texture. In an exemplary embodiment, the surface of the plunger head may have a substantially smooth texture. In another exemplary embodiment, the surface of the plunger head may have a substantially rough texture.

During activation of the firing mechanism, the firing button may move downwardly. As it moves downward, the firing button may exert pressure against portions of the plunger arms that contact the firing button, causing the plunger arms to deform and move toward each other. The texture of the plunger arm surfaces may provide static friction resistance. The texture may thus affect the minimum force required to activate the firing mechanism so that a substance is expelled from the syringe into the patient's body. As such, the surface texture of the head surfaces of the plunger arms may have an effect on the FtF of a firing mechanism assembly.

A study was designed to determine the relationship between the surface texture and the FtF. Plungers were produced having different flex moduli and having either a substantially smooth or a substantially rough ICS and/or SCS that contacts the firing button during activation.

Figure 22:
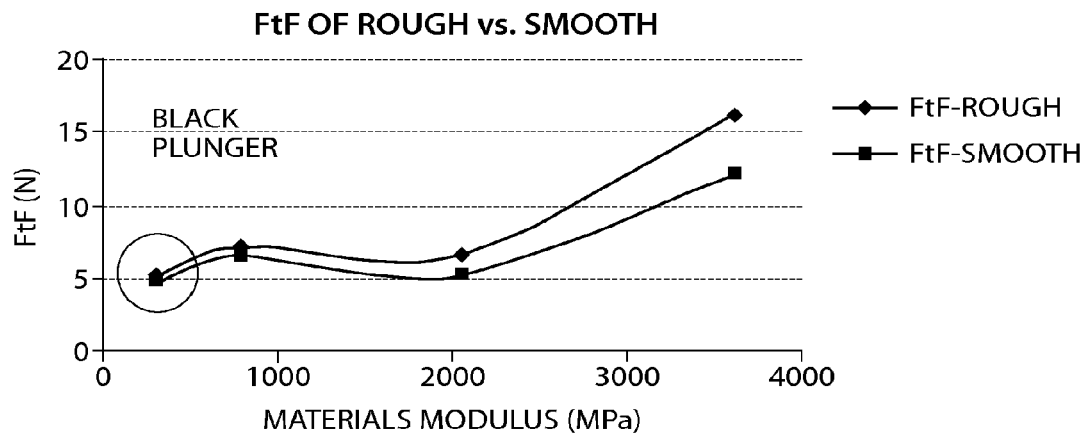
FIG. 22 shows a graph of the FtF of a plunger having varying flex moduli, wherein the surface material is either rough or smooth.

FIG. 22 shows a graph of the FtF of a plunger having varying flex moduli, wherein the surface material is either rough or smooth. Results show that a rough plunger had a higher FtF, and that this effect was more pronounced with plunger materials of a higher flex modulus.

Exemplary embodiments provide a method to configure a plunger in a firing mechanism assembly to achieve an improved FtF by modifying the surface texture of the plunger arms. In an exemplary embodiment, the plunger surface is made substantially rough to achieve a higher FtF. In another exemplary embodiment, the plunger surface is made substantially smooth to achieve a lower FtF. The plunger material can be made rougher to achieve a higher FtF, or made smoother to achieve a lower FtF. Thus, the surface texture of the plunger arms may be configured to control the FtF and to improve the FtF. Exemplary embodiments also provide automatic injection devices that provide automatic injection devices in which the surface texture of the ICS and/or the SCS is configured, singly or in combination with other factors, to improve the FtF.

Example 5

Relationship Between PBB Angle, Plunger Arm Width on FtF

An exemplary plunger in an exemplary firing mechanism assembly may be bifurcated into two plunger arms. The PBB angle is the angle formed between the plunger arms. In an exemplary embodiment, the PBB angle is about 0° and the plunger arms are substantially parallel to each other. In another exemplary embodiment, the PBB angle is higher than 0° and the plungers are not parallel to each other.

During activation of the firing mechanism, the firing button may move downwardly. As it moves downward, the firing button may exert pressure against portions of the plunger arms that contact the firing button, causing the plunger arms to deform and move toward each other. The PBB angle formed between the plunger arms may affect the minimum force required to activate the firing mechanism so that a substance is expelled from the syringe into the patient's body. As such, the PBB angle formed between the plunger arms may have an effect on the FtF of a firing mechanism assembly.

The relationship between PBB angle and plunger arm width was tested. Plungers were made with varied PBB angles (0°, 1°, 2°, 3°, 4°). The configuration of the plungers with 1°, 2°, 3°, 4° PBB angles results in the following plunger arm widths as read from the 3D CAD files of the configurations and as measured from plunger samples. These widths are summarized in Table 6. Table 6 tabulates PBB angles of 0°, 1°, 2°, 3°, and 4°, the corresponding plunger arm width as read from 3D CAD files, the corresponding measured average width of Watershed 11120 Rapid Prototype Plunger (RPT) samples, and the corresponding measure average width of Prototherm 12120 RPT samples. It is seen in Table 6 that different RPT materials result in different plunger arm widths, although the plunger configurations for each PBB angle were the same.

TABLE 6

Relationship between PBB Angle, Plunger Arm Width and FtF

| PBB Angle (°) | Width (mm) read from 3D CAD files | Measured average width (mm) of Watershed 11120 RPT samples | Measured average width (mm) of Prototherm 12120 RPT samples |
|---|---|---|---|
| 0° | 3.05 | 3.00 | 2.77 |
| 1° | 3.38 | 3.28 | 2.98 |
| 2° | 3.71 | 3.67 | 3.32 |
| 3° | 4.05 | 3.91 | 3.50 |
| 4° | 4.38 | 4.19 | 3.88 |

Figure 23:
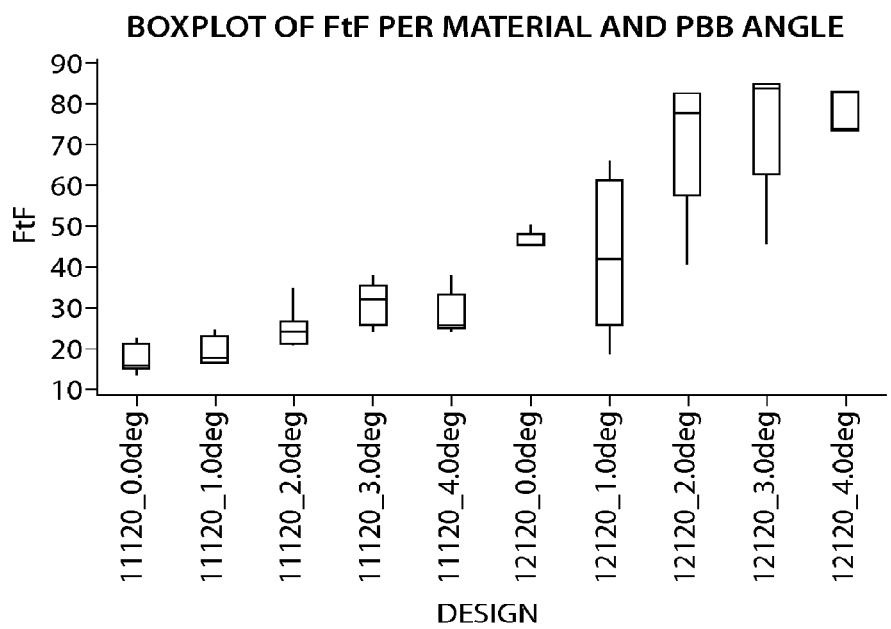
FIG. 23 shows a graph of FtF for plunger arms having various PBB angles.

A study was designed to determine the relationship between the PBB angle and the FtF. Different plungers made of different materials (11120 or 12120 described in Table 3) and having varied PBB angles (0°, 0.5°, 1°, 1.5°, 2°) were tested. FIG. 23 shows a graph of FtF for plunger arms made of either 11120 or 12120 and having various PBB angles. Results show that FtF increases with an increase in the PBB angle. In addition, a high modulus plunger material such as 12120 had a more pronounced increase in FtF with increasing PBB angle, than a lower modulus material such as 11120.

Results of the study show that increasing the PBB angle increases the plunger arm width, which in turn increases the FtF. With increasing PBB angles, the higher flexural modulus material (ProtoTherm 12120) had a more pronounced increase in FtF than a lower flexural modulus material (Watershed 11120). That is, FtF was influenced by both the plunger arm width and the material flexural modulus. In this study, the material flexural modulus of ProtoTherm 12120 was the dominant factor on FtF. Although the plunger arm width was smaller in plungers made of ProtoTherm 12120 than in plungers made of Watershed 11120 per PBB angle, plungers made of ProtoTherm 12120 yielded a higher FtF.

Exemplary embodiments provide a method to configure a plunger in a firing mechanism assembly to achieve an improved FtF by modifying the PBB angle formed between the plunger arms. In an exemplary embodiment, the PBB angle is increased to achieve a higher FtF. In another exemplary embodiment, the PBB angle is decreased to achieve a lower FtF. Thus, the PBB angle may be configured to control the FtF and to improve the FtF.

Exemplary embodiments also provide a method to configure a plunger in a firing mechanism assembly to achieve an improved FtF by modifying a combination of the PBB angle formed between the plunger arms and the flex modulus of the plunger material.

Exemplary embodiments also provide automatic injection devices in which the PBB angle is configured, singly or in combination with other factors, to improve the FtF.

Example 6

Relationship Between ICS Length and FtF

An exemplary plunger arm in an exemplary firing mechanism assembly has a head portion that may include a tabbed foot. The ICS is a portion of the plunger arm head that is configured to contact a firing engagement mechanism, e.g., a firing button. The ICS length is the length of the ICS that is in contact with the firing engagement mechanism.

During activation of the firing mechanism, the firing button moves downwardly. As it moves downward, the firing button exerts pressure against the ICS, causing the plunger arms to deform and move toward each other. The firing button travels along the ICS over the ICS length. The ICS length affects the minimum force required to activate the firing mechanism so that a substance is expelled from the syringe into the patient's body. As such, the ICS length has an effect on the FtF of a firing mechanism assembly.

A study was designed to determine the relationship between the ICS length and the FtF. The study used a control plunger with an ICS angle of about 38° angle and an SCS angle of about 23°. In exemplary plungers, the ICS angle was kept at about 38° and the ICS length was varied from about 2.44 mm to about 2.64 mm, 2.84 mm, and 3.03 mm (increases of about 0.2 mm, 0.4 mm, and 0.6 mm, respectively). In addition, a plunger was tested in which both the ICS angle and the SCS angle were at about 38° (i.e., the ICS and SCS formed one continuous surface without a transitional area). This allowed the firing button to contact the ICS over a larger area (that now encompassed both the ICS and the SCS) before the plunger was released from the firing body.

Figure 24:
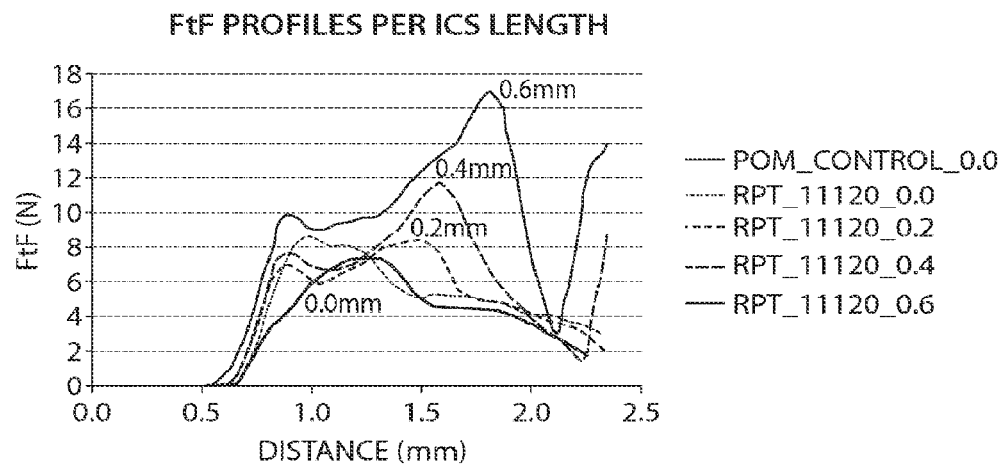
FIG. 24 shows a graph of FtF profiles for plungers in which the ICS length is increased by 0.2 mm, 0.4 mm, and 0.6 mm to 2.64 mm, 2.84 mm, and 3.03 mm, respectively.

FIG. 24 shows a graph of FtF profiles for plungers composed of different materials (a control POM plunger with an original ICS length, a 11120 plunger with an original ICS length, a 11120 plunger with an ICS length increased by about 0.2 mm, a 11120 plunger with an ICS length increased by about 0.4 mm, and a 11120 plunger with an ICS length increased by about 0.6 mm), in which the ICS length was increased by about 0.2 mm, 0.4 mm, and 0.6 mm to about 2.64 mm, 2.84 mm, and 3.03 mm, respectively. Results show that the FtF increased with increases in ICS length. As the ICS length increased, the peaks in the FtF force profile shifted to the right.

Exemplary embodiments provide a method to configure a plunger in a firing mechanism assembly to achieve an improved FtF by modifying the ICS length. In an exemplary embodiment, the ICS length is increased to achieve a higher FtF. In another exemplary embodiment, the ICS length is decreased to achieve a lower FtF. Thus, the ICS length may be configured to control the FtF and to improve the FtF.

Exemplary embodiments also provide a method to configure a plunger in a firing mechanism assembly to achieve an improved FtF by modifying a combination of the ICS length and the ICS angle.

Exemplary embodiments also provide a method to configure a plunger in a firing mechanism assembly to achieve an improved FtF by modifying a combination of the ICS length and the flex modulus of the plunger material.

Exemplary embodiments also provide a method to configure a plunger in a firing mechanism assembly to achieve an improved FtF by modifying a combination of the ICS length, the ICS angle and the flex modulus of the plunger material.

Exemplary embodiments further provide automatic injection devices in which the ICS length is configured, singly or in combination with other factors, to improve the FtF.

Example 7

Relationship Between Plunger Molding Conditions and FtF

An exemplary plunger arm in an exemplary firing mechanism assembly may be molded under different conditions. These conditions may include, but are not limited to, mold temperature, cooling time, etc. Molding conditions of the plunger may affect the physical properties of the plunger, and may in turn affect the minimum force required to activate the firing mechanism so that a substance is expelled from the syringe into the patient's body. As such, molding conditions may have an effect on the FtF of a firing mechanism assembly.

A study was designed to determine the relationship between the plunger molding conditions and the FtF. In the study, plungers made of three polyacetal grade thermoplastic materials were molded using different mold temperatures and cooling times. The normal mold temperature for the polyacetal thermoplastic copolymers (e.g., Hostaform C 13031, Hostaform C 27021 GV 3/30, and Hostaform C 9021 GV1/10 grades) was 200° F. with a 10 second cooling time. The molding condition was changed from 200° F. with a 10 second cooling time to 100° F. with a 25 second cooling time.

Table 7 summarizes the FtF achieved by plungers of different materials molded under different molding conditions.

TABLE 7

Relationship between FtF and Molding Condition for Different Plunger Materials

| Ticona Materials Hostaform C | FtF Study Molding Conditions (F/sec) | Modulus (MPa) | Molding A 10 plungers Mean +/− StDev (N) | Molding B 30 plungers Mean +/− StDev (N) | Molding A 10 plungers Mean +/− StDev (N) | Molding B 10 plungers Mean +/− StDev (N) | FtF Summary FtF (N): Range |
|---|---|---|---|---|---|---|---|
| 13031 (0%) | 200/10 | 3,050 | 7.68 +/− 1.03 | 5.67 +/− 0.81 | 5.22 +/− 0.48 | 5.25 +/− 0.61 | 5.22-7.68 |
| 13031 (0%) | 100/25 | 3,050 | 10.68 +/− 0.81 | 8.27 +/− 0.79 | 6.45+/− 0.60 | 6.44 +/− 0.78 | 6.44-10.68 |
| 27021 GV 3/30 (30%-S) | 200/10 | 3,800 | 12.06 +/− 1.13 | 10.43 +/− 1.19 | — | 9.83 +/− 1.40 | 9.83-12.06 |
| 27021 GV 3/30 (30%-S) | 100/25 | 3,800 | 13.52 +/− 1.18 | 10.71 +/− 1.40 | — | 11.01 +/− 1.01 | 10.71-13.52 |
| 9021 GV 1/10 (10%-F) | 200/10 | 4,800 | — | 8.09 +/− 1.28 | — | 7.84 +/− 1.21 | 7.84-8.09 |
| 9021 GV 1/10 (10%-F) | 100/25 | 4,800 | — | 10.43 +/− 1.02 | — | 9.12 +/− 1.10 | 9.12-10.43 |

The FtF of the Hostaform C 13031 increased from about 5.22-7.68 N to about 6.44-10.68 N when the plunger was molded at a mold temperature of about 100° F. with a cooling time of about 25 seconds. The FtF of the Hostaform C 27021 GV 3/30 increased from about 9.83-12.06 N to about 10.71-13.52 N when the plunger was molded at a mold temperature of about 100° F. with a 25 second cooling time. The FtF of the Hostaform C 9021 GV1/10 increased from 7.84-8.09 N to about 9.12-10.43 N when the plunger was molded at a mold temperature of about 100° F. with a 25 second cooling time.

A plunger molded with a 10% glass-fiber filled grade (e.g., Hostaform C 9021 GV1/10) had a lower FtF than a plunger molded with 30% glass sphere-filled grade even when both plungers were molded under the same molding conditions. The 10% grade plunger was noted to bend inward and to have a smaller width between two arms. This inward bend resulted in the 10% grade having a lower FtF.

Plungers made of thermoplastic materials exhibit the same trends observed for thermosetting materials with regard to material modulus. In addition, results indicate that FtF was dependent on both plunger material inherent properties (e.g., flex modulus) and molding parameters. Thus, the FtF can be an integrated property of both plunger material inherent properties and molding parameters.

Exemplary embodiments provide a method to configure a plunger in a firing mechanism assembly to achieve an improved FtF by modifying molding conditions for molding the plunger (e.g., mold temperature, cooling time, etc). In an exemplary embodiment, the mold temperature may be lowered and the cooling time increased to achieve a higher FtF. In another exemplary embodiment, the mold temperature may be raised and the cooling time decreased to achieve a lower FtF. Thus, the mold temperature and the cooling time may be configured to control the FtF and to improve the FtF.

Exemplary embodiments also provide a method to configure a plunger in a firing mechanism assembly to achieve an improved FtF by modifying a combination of molding conditions (e.g., mold temperature, cooling time) and the flex modulus of the plunger material.

Exemplary embodiments further provide automatic injection devices in which one or more molding conditions of the plunger are configured, singly or in combination with other factors, to improve the FtF.

Example 8

Relationship Between Protrusion Height, Protrusion Angle and FtF

A study was designed to determine the relationship between the protrusion height and the FtF, and the relationship between the protrusion angle and the FtF. The protrusion height and the protrusion angle were altered and the FtF measured to determine the effect of these parameters on the FtF. Protrusion height and angle are interdependent. An increase in protrusion height will automatically decrease the protrusion angle. This is because the base plane line of the protrusion pad at the inside plane remained unchanged as the height was increased.

Table 8 tabulates the results of changing the protrusion height and the protrusion angle on FtF.

TABLE 8

Relationship between FtF and Combinations of Protrusion Height and Protrusion Angle

| Plunger Configuration | Sample Size | Protrusion Height | Protrusion Angle | FtF (N) |
|---|---|---|---|---|
| Configuration #1 | 20 | 0.17 mm | 82° | 5-8N |
| Configuration #2 | 20 | 0.22 mm | 79° | 8-10N |
| Differences | — | 0.05 mm | 3° | — |

The protrusion angle of the plunger was decreased from about 82° (in Configuration #1) to about 79° (in Configuration #2), and protrusion height was increased from about 0.17 mm (in Configuration #1) to about 0.22 mm (in Configuration #2). Results indicate that FtF increased significantly by these changes from about 5-8 N (in Configuration #1) to about 8-10 N (in Configuration #2).

Thus, the protrusion height and the protrusion angle may be configured to control FtF and to achieve an improved FtF.

Example 9

Relationship Between Plunger Configuration and FtF

A study was designed to determine the relationship between the plunger configuration and the FtF. More particularly, two plunger configurations—mid point fixed (MPF) and top point fixed (TPF)—were tested, both with an ICS angle of 48°, to determine their effect on the FtF. In the MPF configuration, the transition point between the ICS and the SCS was kept fixed as the ICS angle was varied. In the TPF configuration, the transition point between the top flat surface and the ICS was kept fixed as the ICS angle was varied.

Figure 25:
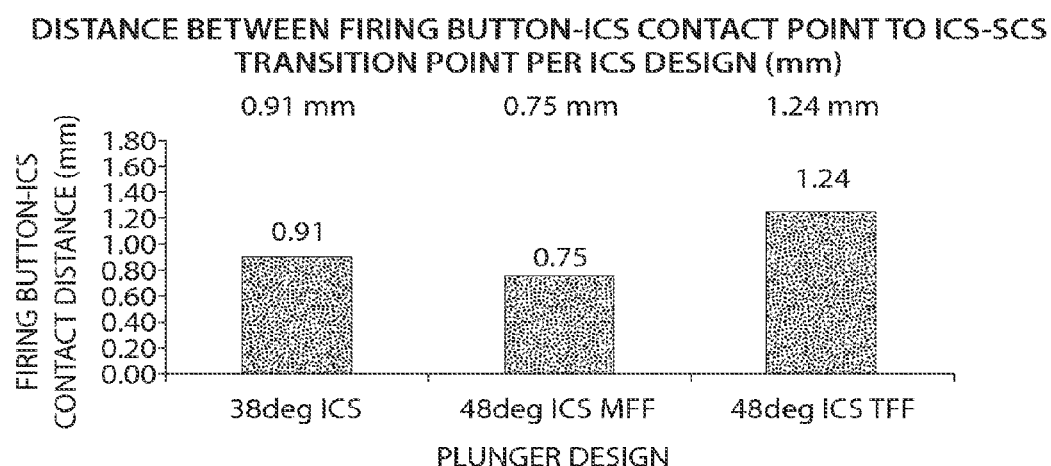
FIG. 25 is a bar graph showing exemplary distances between the initial firing button-ICS contact point and the ICS-SCS transition point for a control plunger with an ICS angle of 38° (about 0.91 mm), an exemplary plunger with a mid point fixed (MPF) configuration and an ICS angle of 48° (about 0.75 mm), and an exemplary plunger with a top point fixed (TPF) configuration and an ICS angle of 48° (about 1.24 mm).

The distance traveled by the firing button along the ICS during firing of the automatic injection device was higher in the TPF configuration than in the MPF configuration. This distance was typically the distance from the initial contact point between the firing button and the ICS to the ICS-SCS transition point. FIG. 25 is a bar graph showing exemplary distances between the initial firing button-ICS contact point and the ICS-SCS transition point for a control plunger with an ICS angle of 38° (about 0.91 mm), the exemplary MPF plunger with an ICS angle of 48° (about 0.75 mm), and the exemplary TPF plunger with an ICS angle of 48° (about 1.24 mm).

Figure 26A:
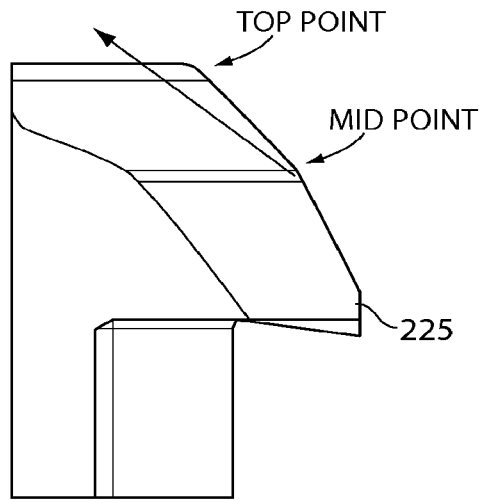
FIG. 26A provides a perspective view of a control plunger with an ICS angle of about 38°.
Figure 26B:
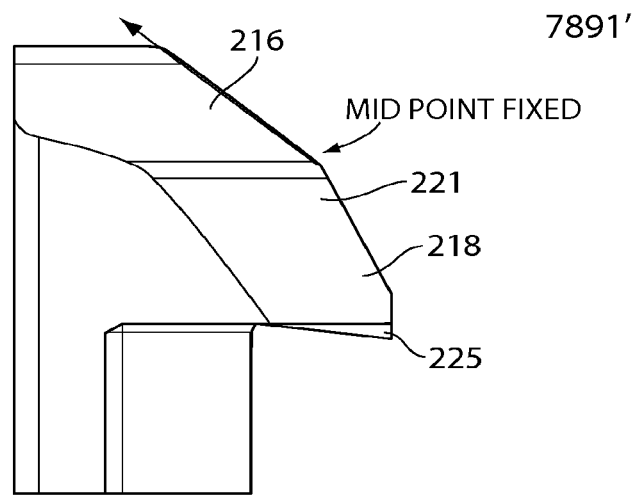
FIG. 26B provides a perspective view of an exemplary plunger with an MPF configuration and an ICS angle of about 48°.
Figure 27A:
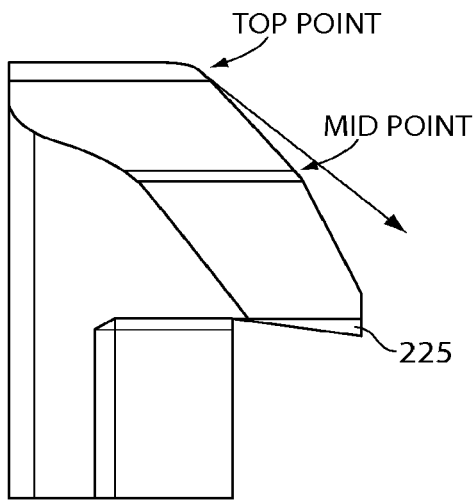
FIG. 27A provides a perspective view of a control plunger with an ICS angle of about 38°.
Figure 27B:
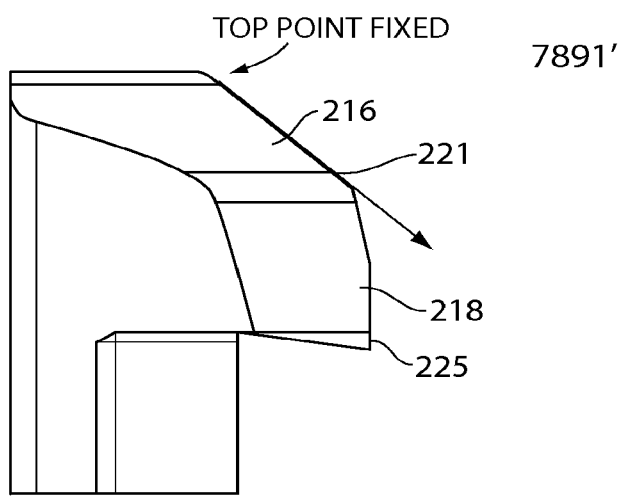
FIG. 27B provides a perspective view of an exemplary plunger with a TPF configuration and an ICS angle of about 48°.

FIG. 26A provides a perspective view of a control plunger with an ICS angle of about 38°. FIG. 26B provides a perspective view of an exemplary plunger with an MPF configuration and an ICS angle of about 48°. FIG. 27A provides a perspective view of a control plunger with an ICS angle of about 38°. FIG. 27B provides a perspective view of an exemplary plunger with a TPF configuration and an ICS angle of about 48°.

Figure 28A:
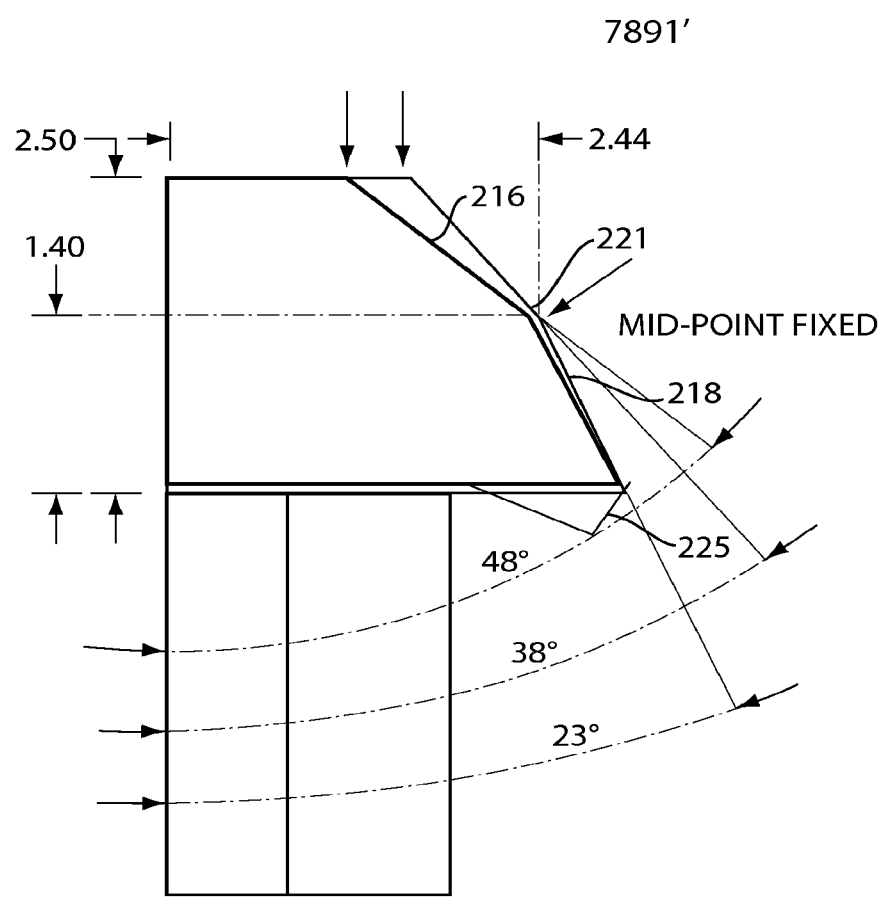
FIG. 28A illustrates a schematic diagram of an exemplary plunger arm having an MPF configuration and an ICS angle of about 48°. In this example, the plunger arm has an SCS angle of about 23°.
Figure 28B:
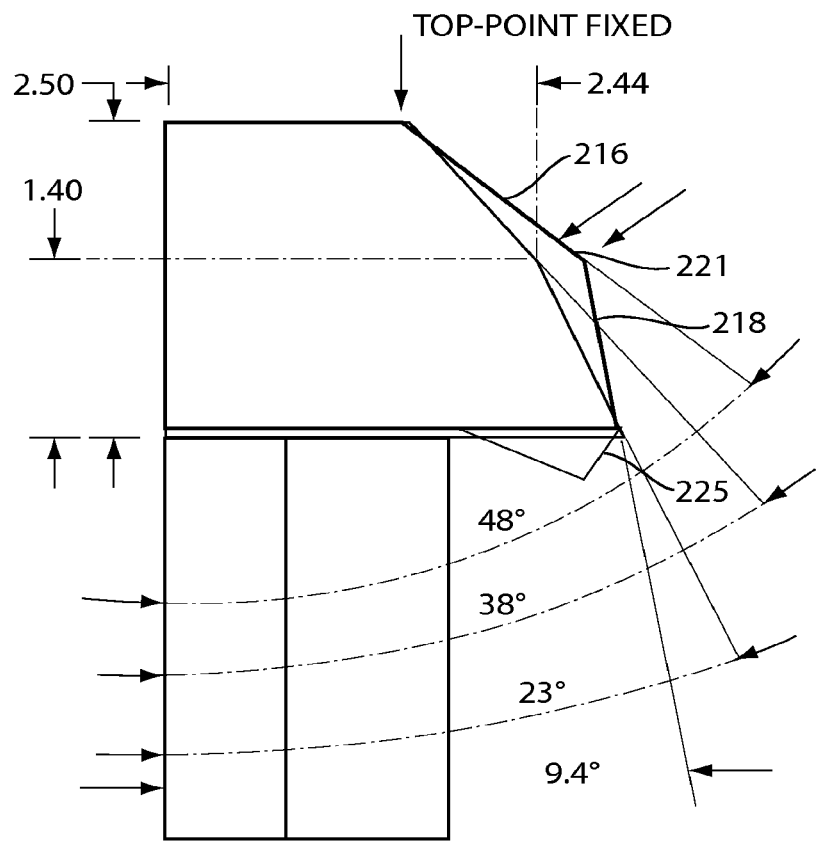
FIG. 28B illustrates a schematic diagram of an exemplary plunger arm having a TPF configuration and an ICS angle of about 48°. In this example, the plunger arm has an SCS angle of about 9.4°.

FIG. 28A illustrates a schematic diagram of an exemplary plunger arm having an MPF configuration and an ICS angle of about 48°. In this example, the plunger arm had an SCS angle was about 23°. FIG. 28B illustrates a schematic diagram of an exemplary plunger arm having a TPF configuration and an ICS angle of about 48°. In this example, the plunger arm had an SCS angle of about 9.4° because the diameter of the plunger arm was kept constant between the MPF and TPF configurations. An exemplary diameter of the plunger arm was about 8.9 mm.

Plungers composed of different materials and molded under different conditions were tested to determine the effect of MPF and TPF configurations on the FtF. The exemplary plungers included: Hostaform C 13031 (molded under 200° F./10 seconds, 200° F./25 seconds, 100° F./10 seconds, 100° F./25 seconds), Hostaform C 27021 GV 3/30 (molded under 200° F./10 seconds, 200° F./25 seconds, 100° F./10 seconds, 100° F./25 seconds), Hostaform C 9021 GV 1/10 (molded under 200° F./10 seconds, 200° F./25 seconds, 100° F./10 seconds, 100° F./25 seconds). Results show that the FtF of plungers with TPF configuration were consistently higher than the FtF of plungers with MPF configuration at each combination of plunger material and molding condition. A switch from MPF configuration to TPF configuration were unexpectedly found to consistently increase FtF in plungers molded from different resins under different molding conditions. The mean FtF of MPF configuration plungers molded from Hostaform C 13031 at 200° F./10 seconds was about 11.33 N, and the mean FtF of TPF configuration plungers molded from the same resin under the same molding condition was about 14.55 N.

Figure 29A:
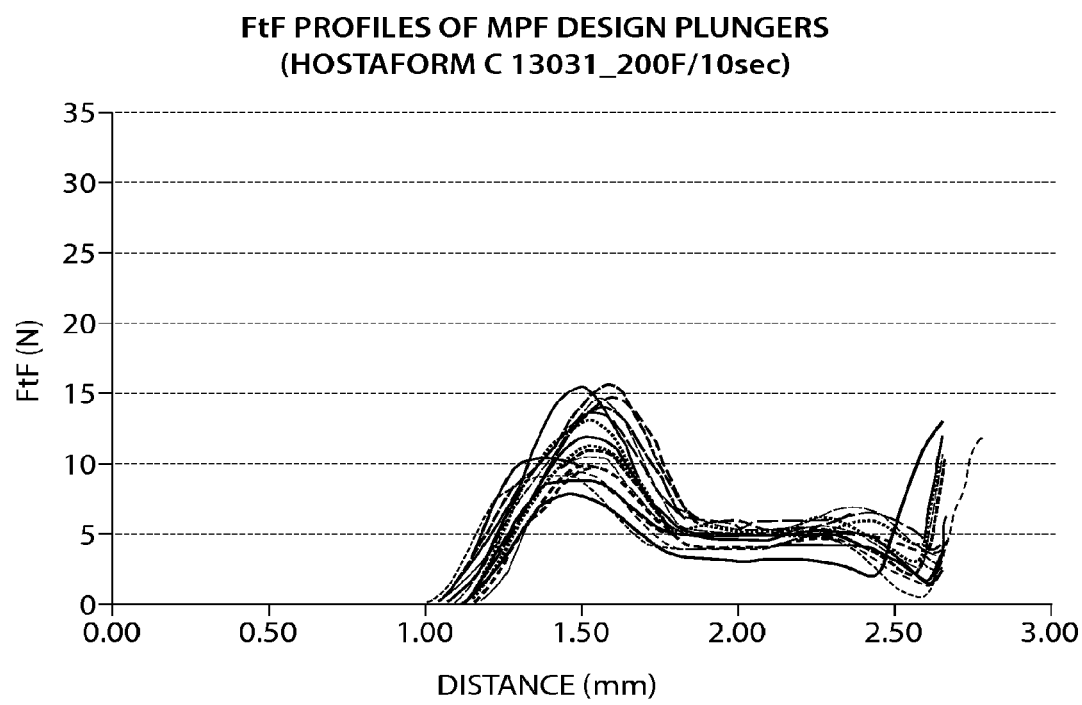
FIG. 29A shows a graph of the FtF profile of an exemplary plunger with an MPF configuration.
Figure 29B:
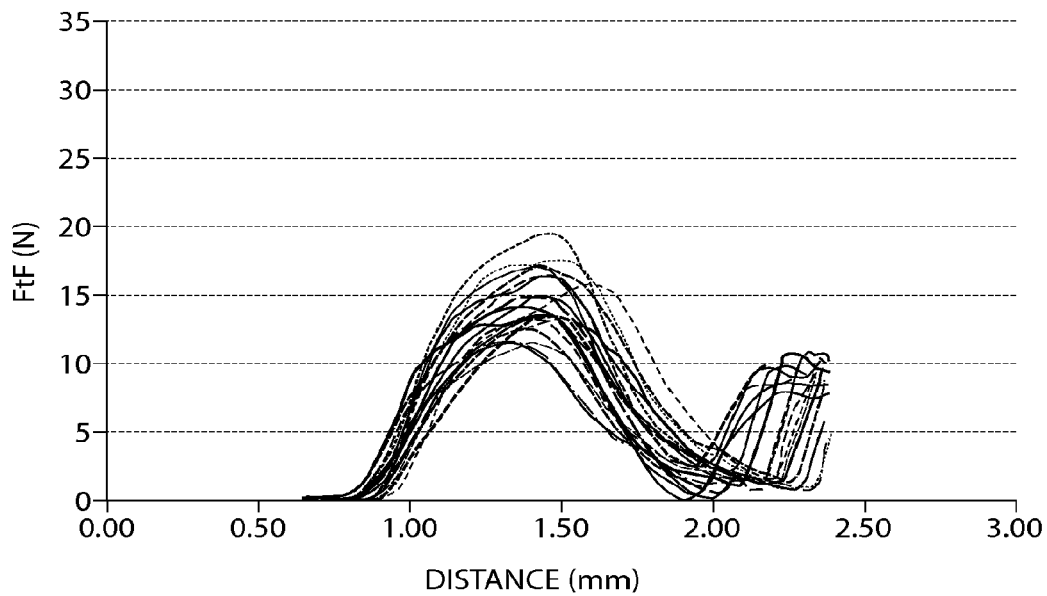
FIG. 29B shows a graph of the FtF profile of an exemplary plunger with a TPF configuration.

FtF force profiles were determined for MPF and TPF configurations of Hostaform C 13031 molded under 200° F./10 seconds. FIG. 29A shows a graph of the FtF (N) profile of the MPF configuration. FIG. 29B shows a graph of the FtF (N) profile of the TPF configuration plunger. FIG. 29A (MPF configuration) shows two peaks, while FIG. 29B (TPF configuration) shows one peak. The absence of the second peak in the TPF configuration is due to the steeper SCS angle of about 9.4°, as compared to the SCS angle of about 23° in the MPF configuration.

FIG. 29A (MPF configuration) shows that the force profile starts at around 1.00 mm, while FIG. 29B (TPF configuration) shows that the force profile starts at around 0.6 mm. This is because, in the MPF configuration, the firing button sits lower on the plunger's ICS compared to the TPF configuration. In addition, the distance between the start point in the force diagram to the first peak is longer in FIG. 29B (TPF configuration) than in FIG. 29A (MPF configuration), since the firing button travels a longer distance along the ICS in the TPF configuration than in the MPF configuration.

A surprising result, shown in FIGS. 29A and 29B, is that the TPF plunger configuration typically achieves higher FtFs than the MPF plunger configuration at each ICS angle for plungers composed of the same material. That is, a TPF plunger with a particular ICS angle typically achieves a higher FtF than an MPF plunger with the same ICS angle and composed of the sample plunger material. As such, at each ICS angle, higher FtFs may be achieved by using a TPF plunger configuration for a plunger composed of the same material rather than an MPF plunger configuration.

Exemplary embodiments provide a method to configure a plunger in a firing mechanism assembly to achieve an improved FtF by modifying the plunger configuration. In an exemplary embodiment, the plunger configuration is changed from MPF to TPF to increase the FtF. In another exemplary embodiment, the plunger configuration is changed from TPF to MPF to decrease the FtF.

In an exemplary embodiment, a TPF plunger configuration is used with an ICS angle of about 48°. In another exemplary embodiment, an MPF plunger configuration is used with an ICS angle of about 48°.

Exemplary embodiments also provide a method to configure a plunger in a firing mechanism assembly to achieve an improved FtF by modifying a combination of the plunger configuration (TPF or MPF) and the plunger material.

Exemplary embodiments also provide a method to configure a plunger in a firing mechanism assembly to achieve an improved FtF by modifying a combination of the plunger configuration (TPF or MPF), the plunger material, and the molding conditions for molding the plunger.

Exemplary embodiments also provide automatic injection devices in which the plunger configuration is configured, singly or in combination with other factors, to improve the FtF.

Example 10

Relationship Between Plunger Material, Protrusion Configuration Combinations on FtF A study was designed to determine the relationship between the plunger material, protrusion configuration combinations on FtF. The plunger material flex modulus, protrusion height and protrusion angle were altered and the FtF measured to determine the effect of these parameters on the FtF.

Table 9 tabulates the flex modulus and protrusion height combinations that are preferred and most preferred to achieve an improved FtF.

TABLE 9

Alteration of Material Flex Modulus and Protrusion Height

| Plunger Configuration | Materials Flex* Modulus (MPa) | Protrusion Height (mm) |
|---|---|---|
| Range | 1,000-6,000 | 0.17-0.47 |
| Preferred Range | 2,000-5,500 | 0.20-0.42 |
| Most Preferred Range | 3,000-5,000 | 0.23-0.37 |

Table 10 tabulates the flex modulus and protrusion angle combinations that are preferred and most preferred to achieve an improved FtF.

TABLE 10

Alteration of Material Flex Modulus and Protrusion Angle

| Plunger Configuration | Materials Flex Modulus (MPa) | Protrusion Angle (°) |
|---|---|---|
| Range | 1,000-6,000 | 82-62 |
| Preferred Range | 2,000-5,500 | 79-65 |
| Most Preferred Range | 3,000-5,000 | 76-68 |

Example 11

Relationship Between ICS Angle, Flex Modulus, Molding Parameter Combinations and FtF The goal of the following study was to determine whether an even higher FtF could be achieved by incorporating an ICS angle change, in addition to modifying plunger material and molding process factors. The ICS angle was increased from about 38° to about 48°.

Table 11 provides results of the measured FtF resulting from plungers made with two resin grades with different material moduli and under two molding conditions. Table 11 also summarizes the FtF achieved for different combinations of initial contact surface (ICS) angles, plunger material, and molding conditions of the plunger. Table 11 also shows that the FtF increases at each combination of plunger material and molding condition with rising ICS angles.

TABLE 11

Relationship between FtF and ICS Angles for Different Plunger Materials

| FtF (N) | Hostaform C 13031 (control) | Hostaform C 13031 (control) | Hostaform C 27021 (30% sphere-filled) | Hostaform C 27021 (30% sphere-filled) |
|---|---|---|---|---|
| | Molding Conditions | | | |
| | 200° F./ 10 sec | 100° F./ 25 sec | 200° F./ 10 sec | 100° F./ 25 sec |
| ICS = 38° | 5.7N | 8.3N | 10.4N | 10.7N |
| ICS = 48° | 14.2N | 13.2N | 21.8N | 23.8N |
| FtF % Increase | 150% | 60% | 110% | 120% |

The FtF increased with increase in ICS angle (from 38° to 48°). The increase in ICS angle (from 38° to 48°) had more impact on the increase of the FtF than the increase in the studied resin material modulus and molding conditions.

Nonetheless, all three parameters were found to affect FtF and, thus, can singly or in combination, be used to improve the FtF of the plunger.

Results show that the FtF at an ICS angle of about 48° was higher than the FtF for an ICS angle of about 38° for each combination of plunger material and molding condition. For example, for the control resin plunger (Hostaform C 13031) molded at a mold temperature of about 200° F. for 10 seconds, the FtF was about 5.7 N and 14.2 N at ICS angles of about 38° and 48°, respectively. For the control resin plunger (Hostaform C 13031) molded at a mold temperature of about 100° F. and cooled for 25 seconds, the FtF was about 8.3 N and 13.2 N at ICS angles of about 38° and 48°, respectively. For the 30% sphere-filled resin plunger (Hostaform C 27021) molded at a mold temperature of about 200° F. and cooled for 10 seconds, the FtF was about 10.4 N and 21.8 N at ICS angles of about 38° and 48°, respectively. For the 30% sphere-filled resin plunger (Hostaform C 27021) molded at a mold temperature of about 100° F. and cooled for 25 seconds, the FtF was about 10.7 N and 23.8 N at ICS angles of about 38° and 48°, respectively.

In addition, FtF values at an ICS angle of about 48° were higher for the filled resin than the unfilled resin, and plunger FtF values at an ICS angle of about 48° were higher at a material modulus of about 3,800 MPa rather than that at 3,050 MPa. FtF increases based on ICS angle increases of about 10° were greater than FtF increases based on resin material modulus changes from 3000 MPa to 4000 MPa, although both ICS angle and resin material modulus changes show improvements in FtF. Similarly, plunger FtF increases attributed to an ICS angle increase of about 10° were greater than FtF increases resulting from either a mold temperature decrease from 200° F. to 100° F. or a molding cooling time increase from 10 second to 25 seconds, although both ICS angle and molding conditions show increases in FtF.

Plungers made of 10% glass fiber-filled resin (4,800 MPa) were also tested using an increased ICS angle under the two molding conditions. For the 10% filled resin plunger having an ICS angle of about 48° molded under 200° F./10 second conditions, the resulting average FtF was similar to the control plunger with a 48° ICS angle (i.e., 14.2 N control vs. 14.2 10% fiber-filled). Interestingly, however, while the FtF average had an average of 13.2 N for the control plunger) (48° under modified molding conditions (110° F./25 seconds), the average FtF for the 10% filled resin plunger was 21.7 N.

In sum, FtF can be increased by altering the ICS angle, the molding conditions, or the resin material, as well as any combination thereof. The aforementioned parameters increase the FtF from about 5 N to about 24 N. Notably the materials used in the above studies are exemplary and non-limiting, as other types of materials may be suitable as well and are contemplated as part of the invention.

Example 12

Relationship Between Material Flex Modulus, Molding Conditions, ICS Angle Combinations and FtF The goal of the following study was to determine whether an even higher FtF could be achieved by incorporating an ICS angle change, in addition to material and process factors. FtF was measured on Hostaform C GV 3/30 and Hostaform C 13031 materials molded using different molding conditions and with altered ICS Angles as shown in Table 12.

Table 12 summarizes the FtF achieved by varying the flex modulus of the plunger material, the molding conditions for molding the plunger, and the ICS angle in the plunger.

TABLE 12

Relationship between FtF and Combinations of Material Flex Moduli, Molding Conditions and ICS Angles

| Plunger Configuration | Materials | Molding Condition (° F./seconds) | Protrusion Angle (°) | ICS Length (mm) | PBB (°) | ICS Angle (°) | FtF (N) |
|---|---|---|---|---|---|---|---|
| 1 | Hostaform C GV 3/30 | 200 F./10 sec | 79 | 2.44 | 0 | 38 | 10.4 |
| 2 | Hostaform C GV 3/30 | 200 F./10 sec | 79 | 2.44 | 0 | 48 | 21.8 |
| 3 | Hostaform C GV 3/30 | 100 F./25 sec | 79 | 2.44 | 0 | 38 | 10.7 |
| 4 | Hostaform C GV 3/30 | 100 F./25 sec | 79 | 2.44 | 0 | 48 | 23.8 |
| 5 | Hostaform C 13031 | 200 F./10 sec | 79 | 2.44 | 0 | 38 | 5.7 |
| 6 | Hostaform C 13031 | 200 F./10 sec | 79 | 2.44 | 0 | 48 | 14.2 |
| 7 | Hostaform C 13031 | 100 F./25 sec | 79 | 2.44 | 0 | 38 | 8.3 |
| 8 | Hostaform C 13031 | 100 F./25 sec | 79 | 2.44 | 0 | 48 | 13.2 |

Thus, a combination of the plunger material, molding conditions and ICS angle may be configured to control FtF and to achieve an improved FtF.

Example 13

Relationship Between Plunger Configuration, Plunger Material Molding Condition Combinations and FtF Various conditions of the plunger (including plunger configuration, plunger materials, and molding parameters) were studied in an effort to improve the FtF. Three resins of various moduli (of the polyacetal family) were also studied, including the control Hostaform C 13031, 27021 GV3/30 (30% sphere material), and 9021 CV1/10 (a 10% fiber material). The molding conditions tested includes 200° F./10 seconds (control); 200° F./25 seconds; 100° F./10 seconds; and 100° F./25 seconds. The impact of the plunger configuration (TPF vs. MPF) on ejection time was also studied.

Figure 30:
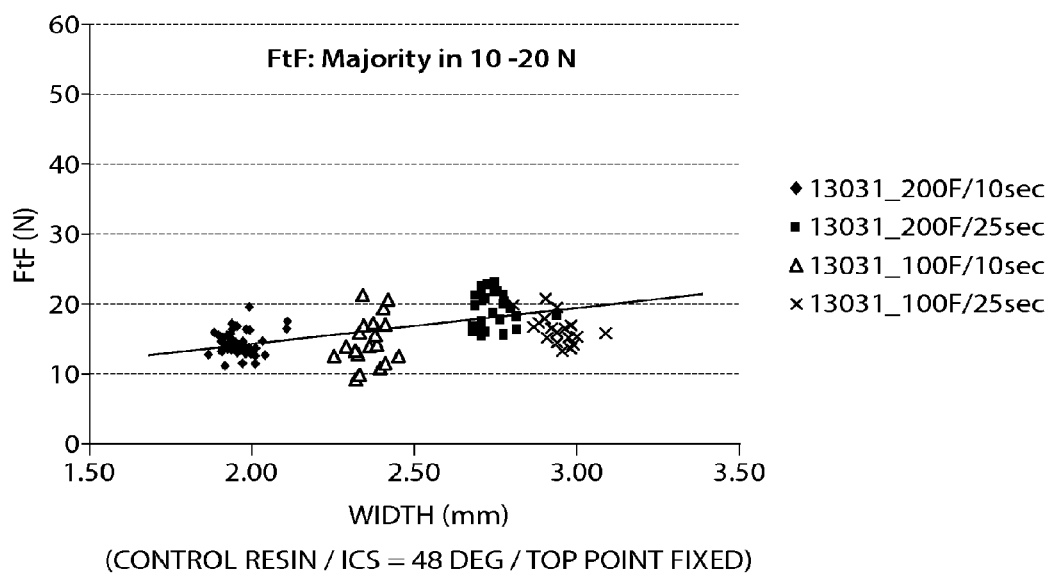
FIG. 30 shows a graph of the FtF versus the plunger arm width.

The FtF was determined for various TPF configuration plungers molded from one of the four molding conditions described above using the control resin (Hostaform C 13031). FIG. 30 shows a graph of the FtF (N) values versus the width (mm) of plungers made from the control resin (13031) with an ICS of 48°, top point fixed (TPF) made under various molding conditions. The majority of the plungers exhibit an FtF between 10-20 N, with a range of 9.2-23.9 N. The combination of the control resin with the TPF 48° ICS configuration was found not to be sensitive to the molding conditions, as described below in Table 12.

Table 13 tabulates the FtF achieved using the resin Hostaform 13031 molded under four different molding conditions: at 200° F. for 10 seconds, at 100° F. for 10 seconds, at 200° F. for 25 seconds, and at 100° F. for 25 seconds. An FtF of between 10 and 20 N was achieved for all four molding conditions. However, there were variations in the FtF achieved between the different molding conditions. The FtF was substantially the same—at 14.6 N and 14.7 N, respectively—for molding at 200° F. for 10 seconds and at 100° F. for 10 seconds. The FtF was higher at about 16.8 N for molding at 100° F. for 25 seconds, and substantially higher at 19.2 N for molding at 200° F. at 25 seconds.

TABLE 13

| FtF (ICS = 48°) for a Control Resin (e.g., Hostaform 13031) at Different Molding Conditions | | | | |
| --- | --- | --- | --- | --- |
| | 13031_200° F./ 10 sec | 13031_100° F./ 10 sec | 13031_200° F./ 25 sec | 13031_100° F./ 25 sec |
| Average FtF (N) | 14.6 | 14.7 | 19.2 | 16.8 |

Figure 31:
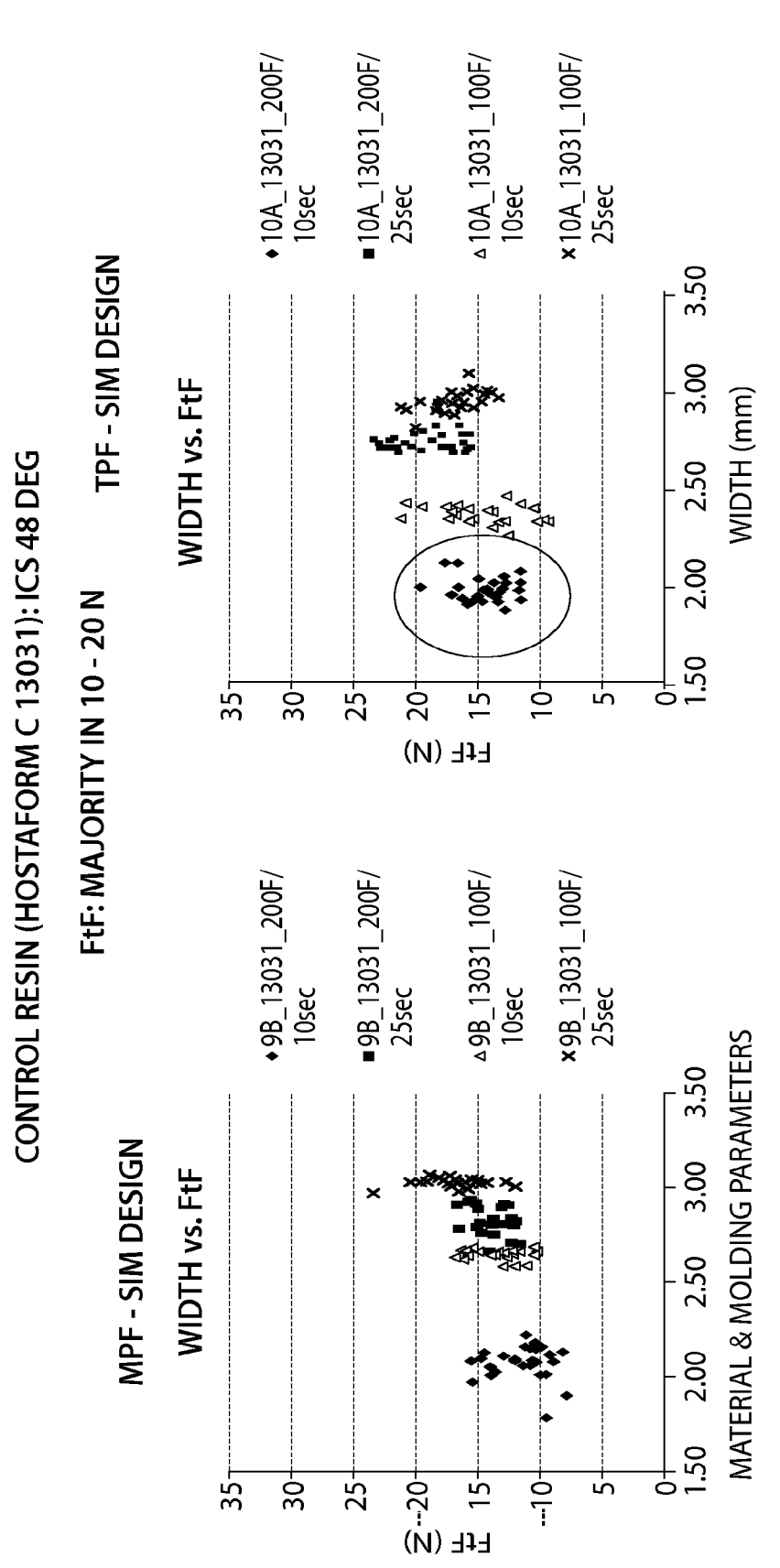
FIG. 31 provides two graphs which compare the FtF of the ICS=48° MPF vs. TPF plungers made from the control resin under various molding conditions for different plunger arm widths.

The FtF of the ICS=48° TPF plunger made from control resin under the four molding conditions was then compared with the FtF (N) of the ICS=48° MPF plunger made from control resin under the four molding conditions. FIG. 31 provides two graphs which compare the FtF of the ICS=48° MPF vs. TPF plungers made from the control resin under various molding conditions. The results are described in FIG. 31, and show that the TPF longer ICS resulted in slightly higher FtF values, although the majority of the calculated FtF values were within the 10-20 N range.

Figure 32:
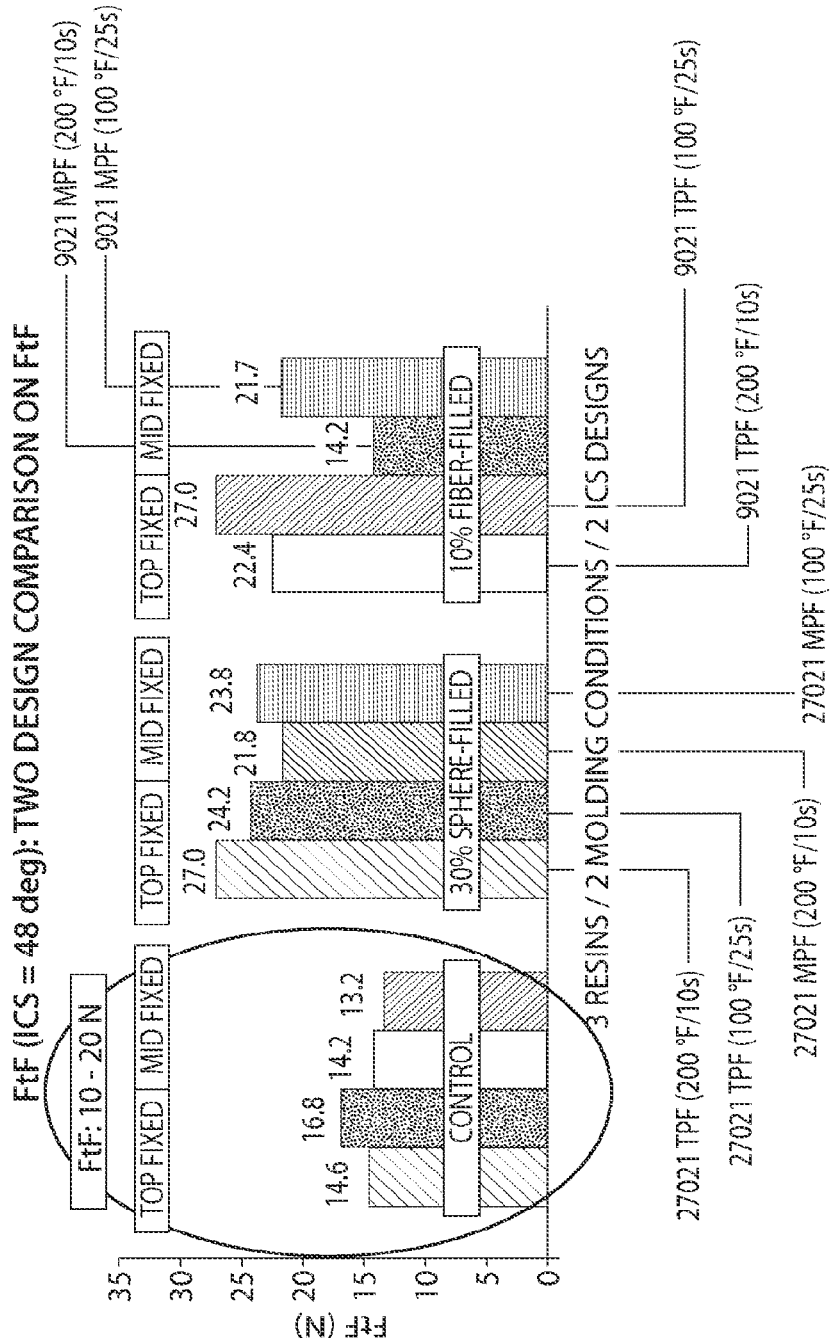
FIG. 32 provides a bar graph which compares the FtF of the ICS=48° MPF vs. TPF plungers made from different resins under various molding conditions.

To determine the impact of different polyacetal materials on the FtF (N) of the both the TPF and MPF configurations (ICS=48°) and materials 27021GV 3/30 and 9021 GV 1/10 were tested against the control material (13031). In addition to the material variations, two different molding conditions (100° F./25 seconds and 200° F./10 seconds) were tested for the 27021 and 9021 test plungers. The results of the study are provided in FIG. 32. Both the TPF and MPF plungers made from control resin (13031) had FtF values within the 10-20 N range, while the average of the other combinations generally resulted in higher FtF values.

Figure 33:
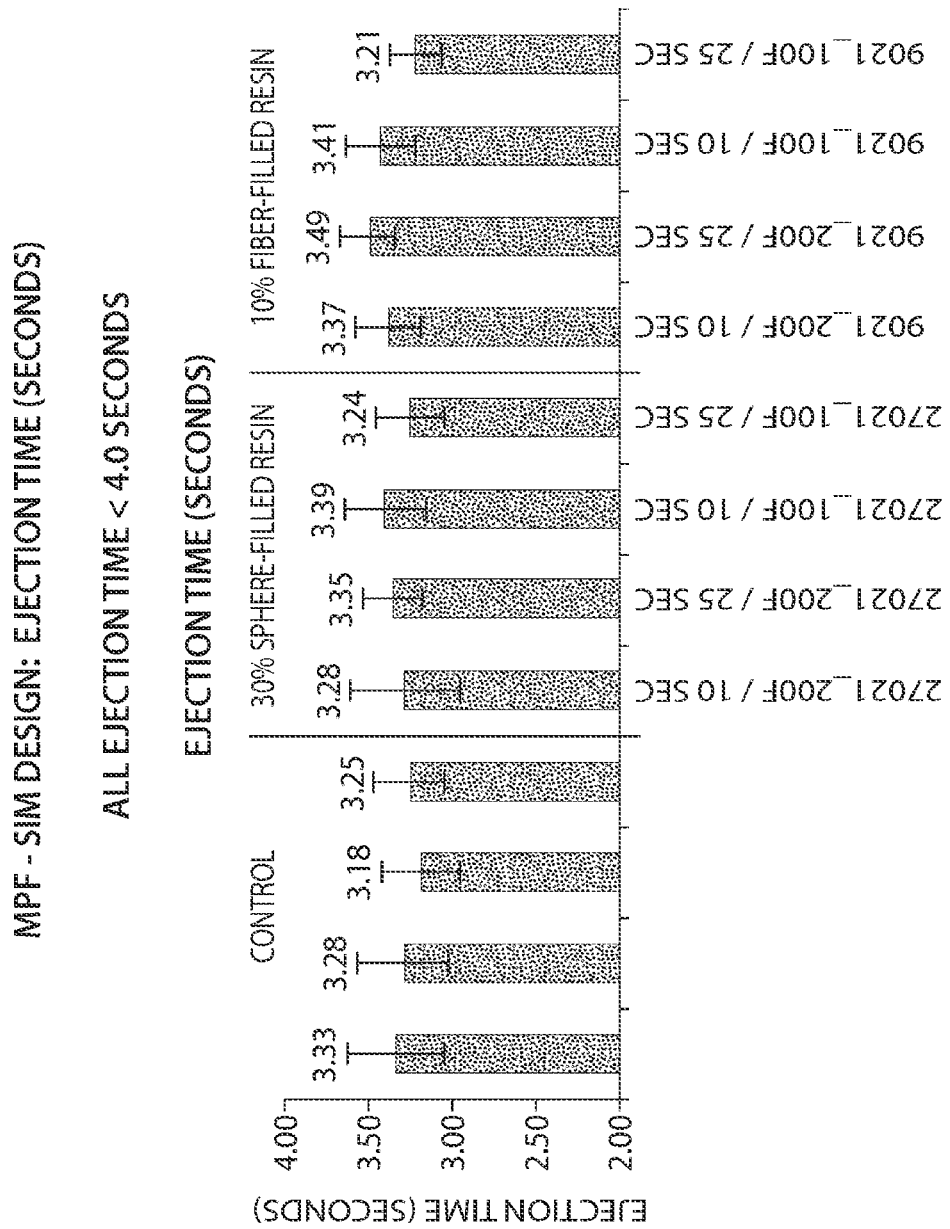
FIG. 33 shows a graph which compares ejection times for ICS=48° MPF plungers based on various materials and molding conditions.
Figure 34:
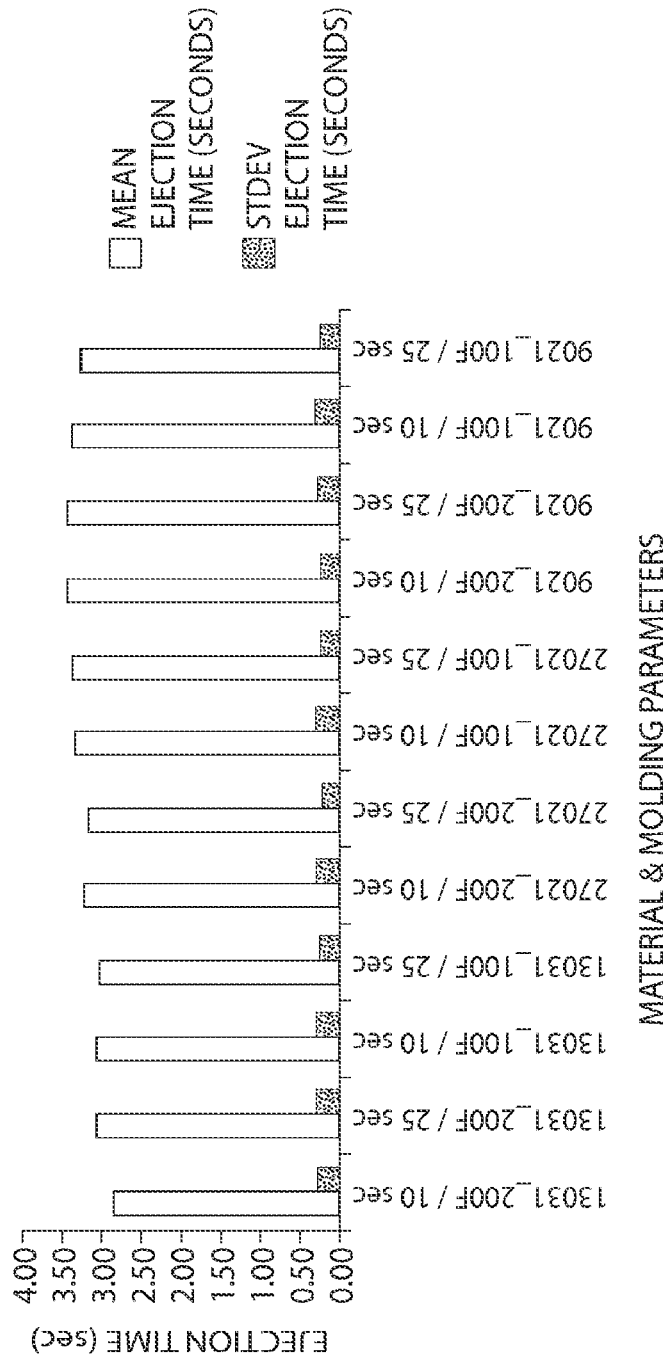
FIG. 34 shows a graph which compares ejection times for ICS=48° TPF plungers based on various materials and molding conditions.
Figure 35:
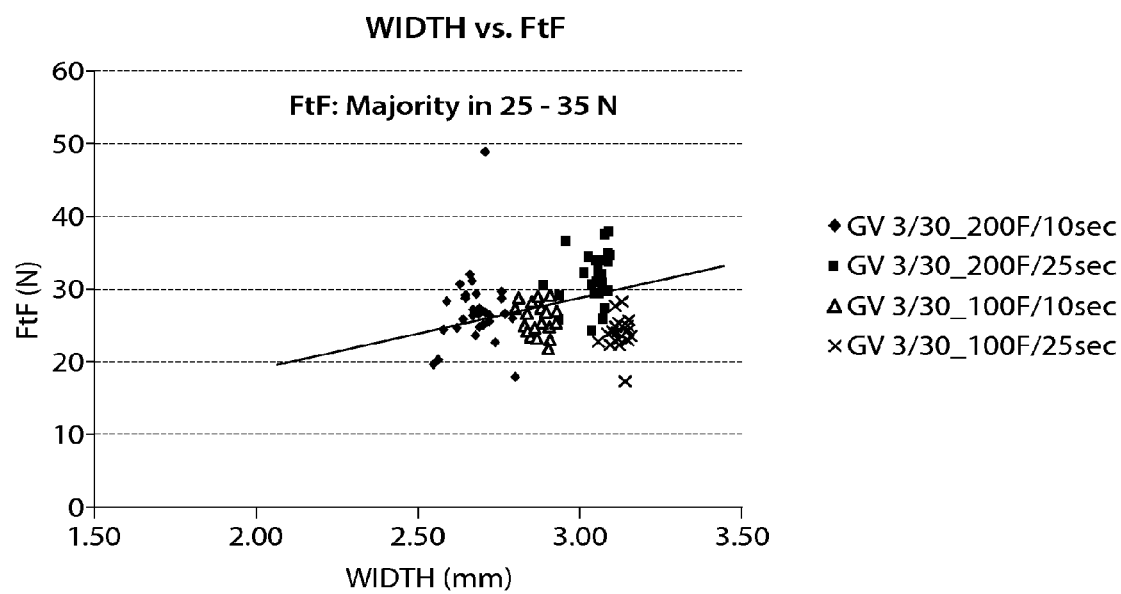
FIGS. 35-40 show graphs that examine the FtF for plunger molded under various molding conditions, having various ICS angles, and composed of various materials.
Figure 36:
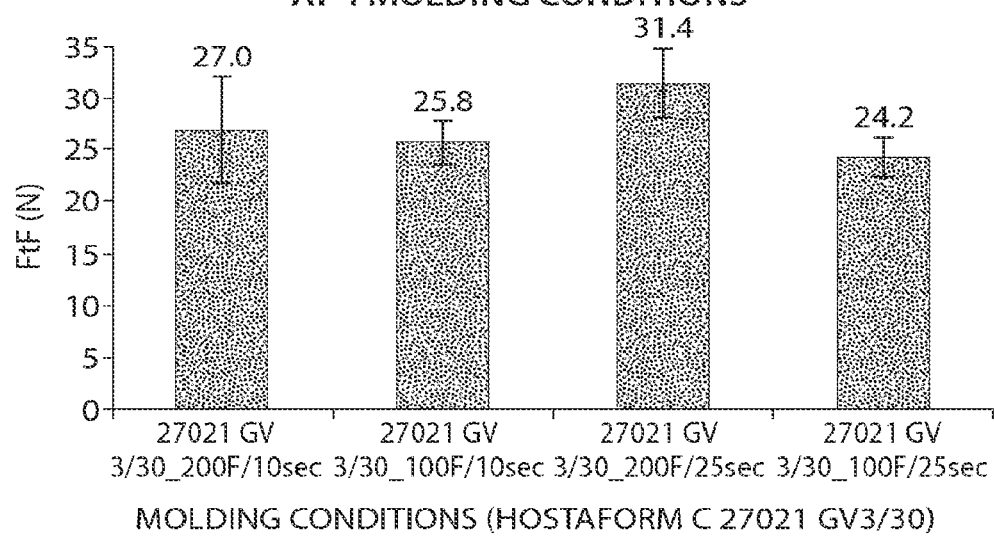
Figure 37:
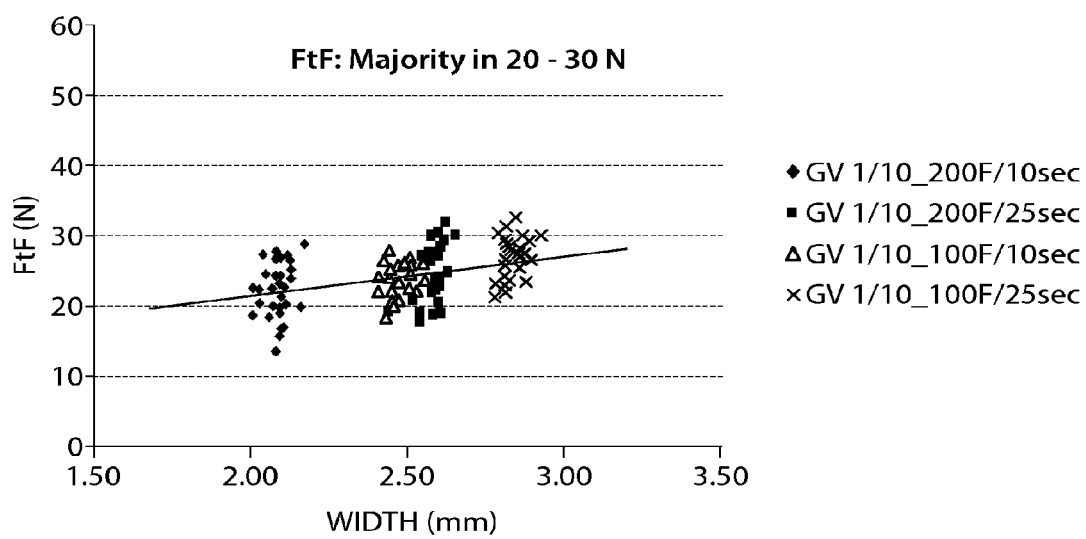
Figure 38:
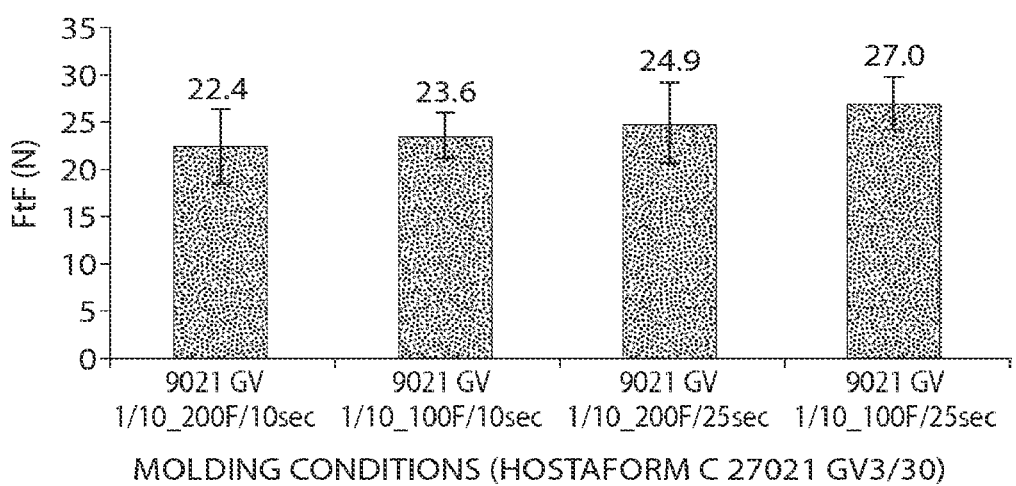
Figure 39:
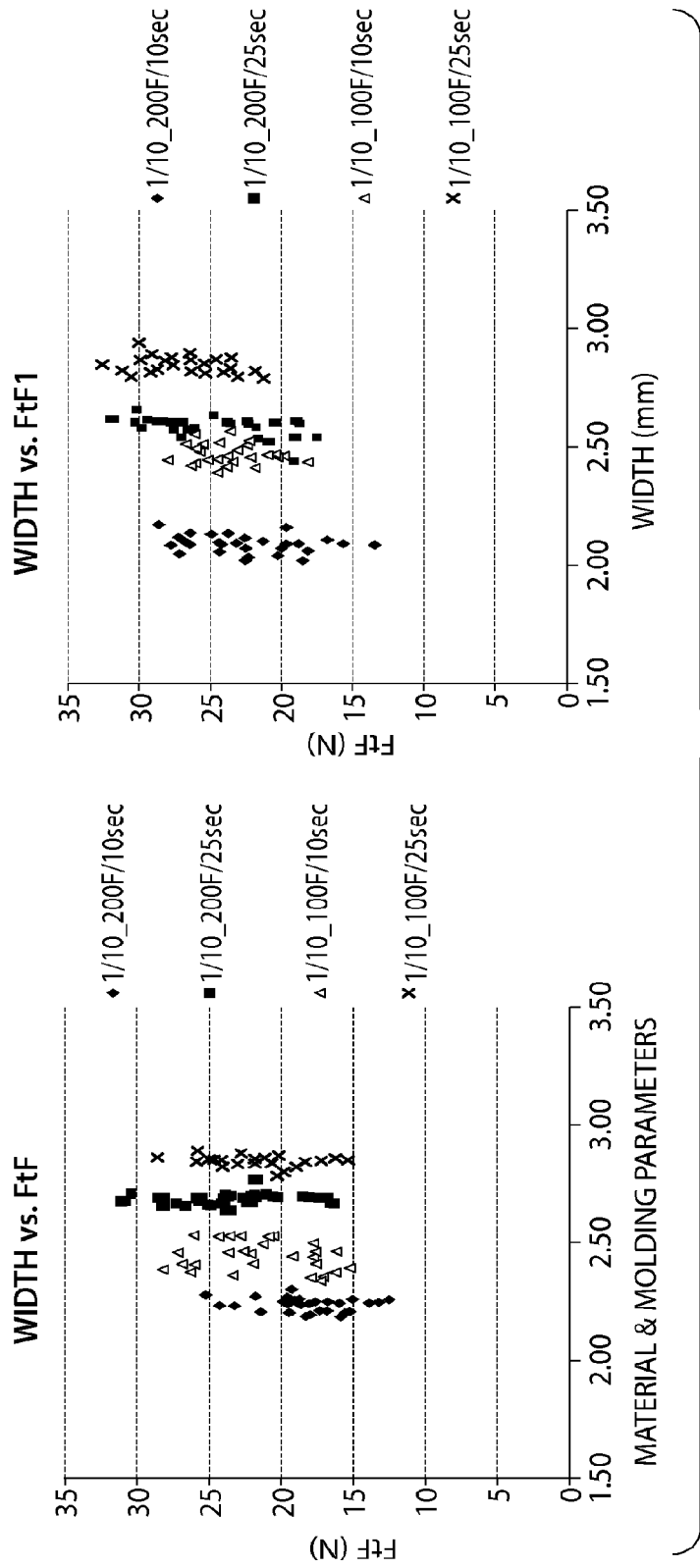
Figure 40:
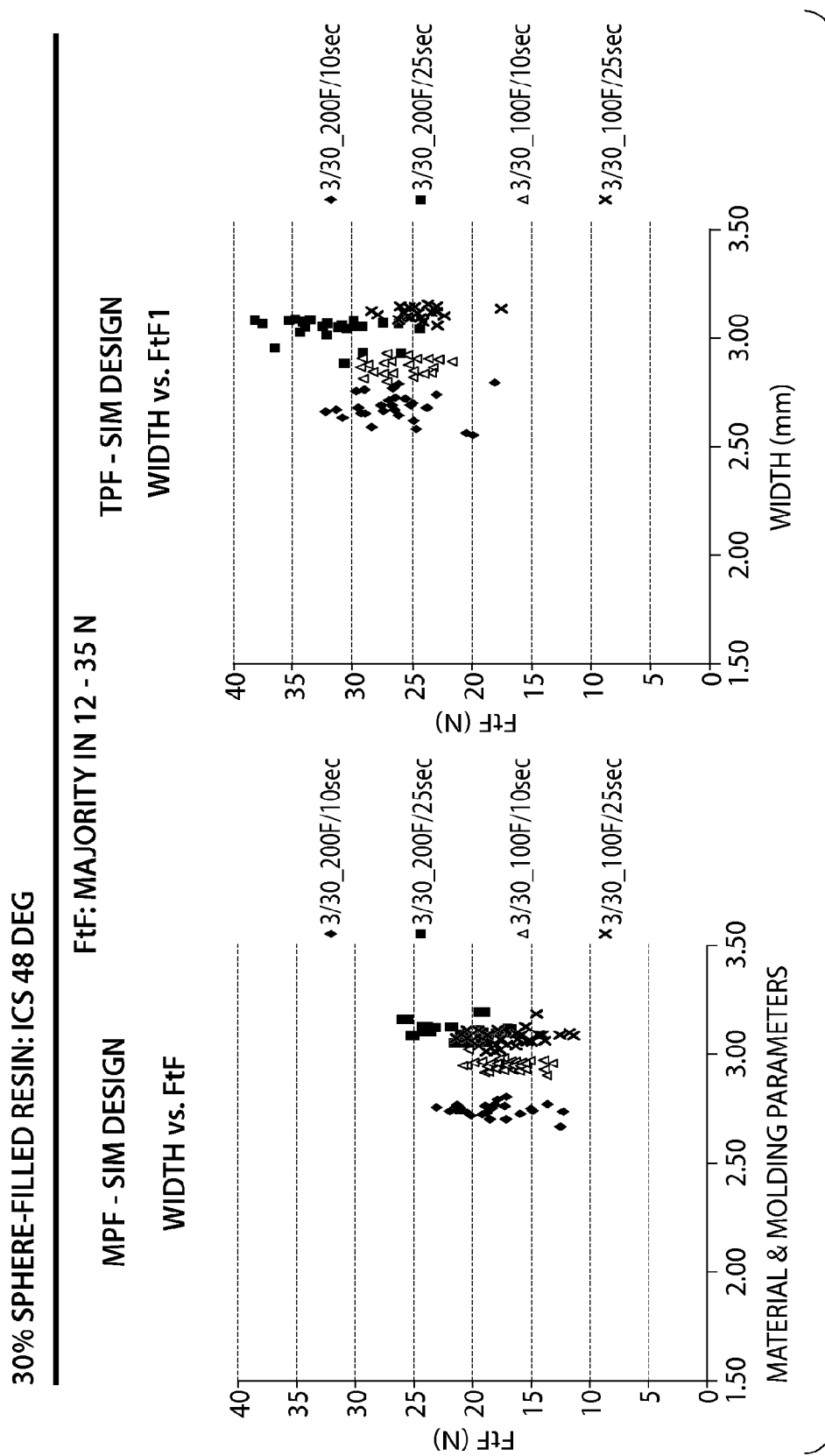

FIGS. 33 and 34 show ejection times for both the MPF and TPF configurations for plungers created using various molding conditions and composed of different materials. The ejection time is the time taken by the automatic injection device to eject the dose of the therapeutic agent contained in the syringe. FIG. 33 shows a graph which compares ejection times for ICS=48° MPF plungers, while FIG. 34 shows a graph which compares ejection times for ICS=48° TPF plungers. In FIG. 33, the molding conditions for the control plunger were varied in a similar fashion as the 30% sphere-filled test plunger and the 10% fiber-filled test plunger. FIGS. 33 and 34 show that varying the molding conditions and plunger material does not significantly affect the ejection times.

Additional results for the various materials/configurations/and molding conditions are described in FIGS. 35-40. FIGS. 35-40 show graphs that examine the FtF for plunger molded under various molding conditions, having various ICS angles, and composed of various materials.

In sum, the plunger configuration had an impact on FtF values. The top-point fixed (TPF) configuration had higher FtF values than the mid-point fixed (MPF) configuration. The TPF also had a longer ICS length than the MPF configuration. The configuration change (at ICS angle of about 48°) was sufficient to establish an FtF of about 10-20 N. Thus, an FtF of about 10-20 N was achieved without changing the material and/or the molding process. FtF was also increased by changing the molding conditions and/or the plunger material.

Example 14

Relationship Between Controllable Parameters and Ejection Time

A study was performed to determine if changing certain controllable parameters affects the time required to eject all the substance from the syringe. Exemplary plungers had an ICS angle of 48° and were made according to different molding conditions. The plungers were tested to determine the ejection time when used in an automatic injection device.

Table 14 tabulates results from the ejection study for different combinations of plunger materials and plunger molding conditions. The plunger materials include control resin (Hostaform C 13031) with an ICS angle of 48°, 30% sphere-filled resin (Hostaform C 27021 GV3/30) with an ICS angle of 48°, 10% fiber-filled resin (Hostaform C 9021 GV3/30) with an ICS angle of 48°, and control resin (Hostaform C 13031) with an ICS angle of 38°. The plunger molding conditions include molding at a mold temperature of 200° F. and cooled for 10 seconds, molding at a mold temperature of 100° F. and cooled for 25 seconds, and control molding conditions.

TABLE 14

Ejection Time Comparison

| Ejection Time (seconds) | Plunger with control resin (Hostaform C 13031) (48°) | Plunger from 30% sphere-filled resin (Hostaform C 27021 GV3/30) (48°) | Plunger from 10% fiber-filled resin (Hostaform C 9021 GV 1/10) (48°) | Control Plunger (C13031 and ICS angle = 38) |
|---|---|---|---|---|
| Molding at 200° F./ 10 second | 3.65 | 3.76 | 3.72 | — |
| Molding at 100° F./ 25 seconds | 3.64 | 3.80 | 3.63 | — |
| Control molding condition | — | — | — | 3.17 |

The results tabulated in Table 14 show that the average ejection time did not change when the plunger was molded by a different grade of resin and/or molding conditions. For plungers with an ICS angle of about 48°, the ejection time varies very narrowly among the different combinations of plunger materials and plunger molding conditions. The range of ejection time variation was between about 3.63 minutes and about 3.80 minutes. In addition, results in Table 14 show that increasing the FtF by increasing the ICS angle to 48° had little effect on the overall ejection time—where the ejection time averages about 3.65 minutes—compared to the control plunger with an ICS angle of 38°—where the ejection time averages about 3.17 minutes. Similar results were obtained using plungers having an ICS angle of about 38°.

Patient Study on FtF

Different configurations of exemplary automatic injection devices were patient-tested to determine an optimal FtF range that would be high enough to minimize misfires and low enough to be comfortably operable by patients. Eight different configurations were tested in three parts of the patient study, with the configurations varying both in plunger configuration (mid point fixed (MPF) and top point fixed (TPF and the FtF required to eject the substance from the device (with the FtF varying within about 14-29 N).

During the patient study, human participants were requested to perform mock injections using the tested device configurations. The plunger configuration and actual FtF of the devices were known. The participants were asked to estimate the FtF required to activate the firing button of the devices. The participants were also asked to estimate the required FtF above which they would feel discomfort in operating the device, and the required FtF above which they would feel intolerable discomfort in operating the device.

A total of 33 patients (28 females and 5 males) participated in the study. Their ages ranged from 28 to 66 years, with an average age of 49.5 years. Fifty eight percent of the participants were at least 50 years old. All participants had been diagnosed with rheumatoid arthritis (RA) by a rheumatologist, and suffered from RA that affected their hands.

A mock injection trial was considered a success if the participant was able to place the device at the injection site and activate the firing button in about thirty seconds or less. A mock injection was considered a failure if the participant was unable to activate the firing button within about thirty seconds.

Part 1: In a first part of the patient study, four configurations of the automatic injection device were tested: a device with MPF plunger configuration and FtF of about 14-16 N, a device with MPF plunger configuration and FtF of about 21 N, a device with TPF plunger configuration and FtF of about 14-16 N, and a device with TPF plunger configuration and FtF of about 21 N. The objectives of the first part of the study were to determine if patients with severe RA affecting their hands: (a) reliably noticed a difference between the MPF and TPF plunger configurations when the required FtF was held constant at 14-16 N or 21 N; (b) reliably noticed a difference between the FtF required to activate the firing buttons of the tested configurations, regardless of plunger configuration; (c) would experience discomfort as a result of using any of the tested configurations to administer an injection twice per month; or (d) would consider the force required to activate the firing buttons of any tested configurations to be intolerable for an injection administered twice per month.

Given a set of four injection devices with firing buttons that require about 14-16 N and about 21 N of force to activate and use MPF or TPF plunger configurations, RA patients with severe hand disability could reliably identify the 14-16 N MPF device as the "easiest" to fire. However, these patients were unable to reliably distinguish between the 14-16 N TPF, 21 N TPF, and 21 N MPF injection devices. In other words, the difference between MPF and TPF plunger configurations was noticed by participants when the FtF required to activate the firing button was about 14-16 N, but not about 21 N. Also, the difference between injection devices requiring about 14-16 N or about 21 N of force to activate the firing button was noticed by participants when using devices with MPF plunger configurations, but not TPF plunger configurations.

A 2×2 repeated measures ANOVA was conducted to analyze the data from Part 1 of the study, where the FtF (14-16 N, 21 N) and plunger configuration (MPF, TPF) were the within-subjects variables. The purpose of this analysis was to determine if participants were able to differentiate between the FtF required to activate each device's firing button, and whether or not their estimates differed for devices that required the same FtF to activate the firing button, but used different plunger configurations. The study found a significant main effect for FtF ($F_{1,30}$=31.05, p<0.001), such that participants estimated the FtF of the 14-16 N firing buttons (M=7.65) to be less than the FtF of the 21 N firing buttons (M=9.80) regardless of plunger configuration. The study also found a significant main effect for plunger configuration ($F_{1,30}$=25.94, p<0.001), such that participants estimated the FtF required to activate the firing buttons with MPF plungers (M=7.87) to be less than the FtF required to activate the firing buttons with TPF plungers (M=9.59) regardless of the actual amount of force required to activate the firing buttons.

Both of these main effects were moderated by a significant interaction between FtF and plunger configuration ($F_{1,30}$=36.80, p<0.001), such that participants estimated the FtF required to activate the firing buttons with TPF plungers to be greater than the FtF required to activate the firing buttons with MPF plungers for the 14-16 N devices ($M_{difference}$=3.48), but not for the 21 N devices ($M_{difference}$=0.07).

Figure 41A:
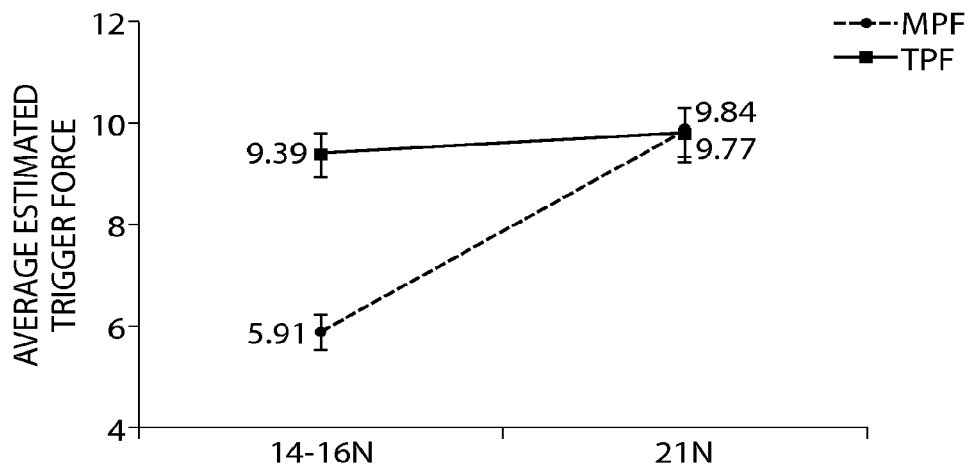
FIG. 41A provides a plot of the average estimated FtF (i.e., the force estimated by participants) versus the actual average FtF for a first part of a user study.

These results are summarized in FIG. 41A which provides a plot of the average estimated FtF (i.e., the force estimated by participants) versus the actual average FtF. At an actual FtF of 14-16 N, the participants estimated the FtF to be about 9.39 N for the TPF configuration and about 5.91 N for the MPF configuration. At an actual FtF of 21 N, the participants estimated the FtF to be about 9.84 N for the TPF configuration and 9.77 N for the MPF configuration. In other words, administering an injection with the TPF plunger configuration was harder for participants when using the 14-16 N devices, but not when using the 21 N devices.

That is, participants reliably identified the 14-16 N MPF device as the device requiring the lowest FtF to activate the firing button. However, participants were unable to discriminate between the FtF required to activate the firing buttons of the other devices. In other words, participants could reliably identify the difference between MPF and TPF plunger configurations when the FtF was about 14-16 N, but not when the FtF was about 21 N.

The estimated point of discomfort is the force estimated by a participant above which the participant feels discomfort in activating the firing button. The estimated point of intolerability is the force estimated by a participant above which the participant feels intolerable discomfort in activating the firing button.

A repeated measures ANOVA was conducted with six levels of the within-subjects manipulation of the FtF: the four device configurations from Part 1 plus participants' estimations of discomfort and intolerability. Participants' overall estimate of the point at which the FtF required to activate a device's firing button would cause discomfort (M=14.79) was significantly greater (p<0.01) than the estimated FtF of each of the four configurations. The discomfort estimate was also significantly (p<0.001) lower than the estimate of the point at which the force required to activate a device's firing button would be intolerable (M=23.11).

Figure 41B:
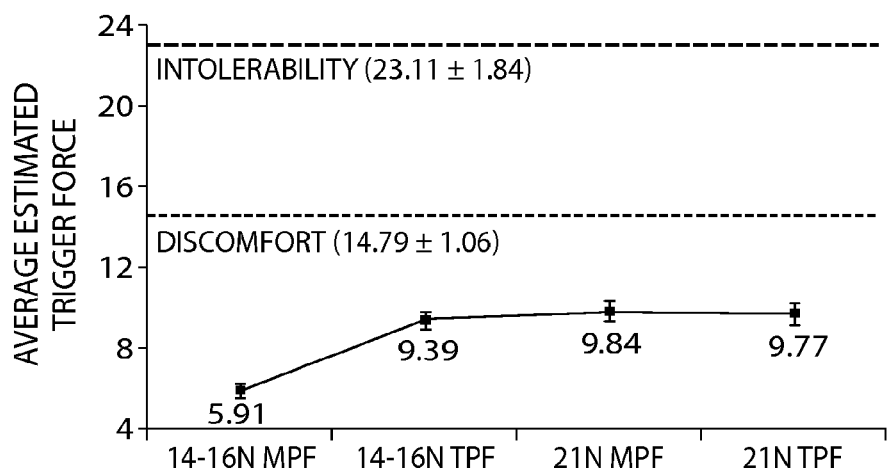
FIG. 41B provides a plot of the average FtF estimated by the participants versus the actual average FtF of the MPF and TPF configurations for the first part of the user study.

These results are summarized in FIG. 41B which provides a plot of the average FtF estimated by the participants versus the actual average FtF of the MPF and TPF configurations. The plot indicates that discomfort is felt when the estimated FtF becomes greater than about 14.79 N, and firing the firing button becomes intolerably uncomfortable when the estimated FtF becomes greater than about 23.11 N. None of the four configurations (14-16 N MPF, 14-16 N TPF, 21 N MPF, 21 N TFP) causes an average estimated force that falls in the "discomfort" or "intolerability" range, i.e., all fall below 14.79 N. In other words, the FtF required to activate each of the configuration's firing buttons in Part 1 was significantly lower than the amount of force that would first cause participants to notice discomfort.

While participants on average estimated the points of discomfort and intolerability to be significantly greater than the FtF required to activate the firing button of any configuration in Part 1, thirteen percent (four participants) estimated both the points of discomfort and intolerability to be less than or equal to the FtF required to activate one or more of the device's firing buttons. An additional twenty three percent (seven participants) estimated only the point of discomfort to be less than or equal to the FtF required to activate one or more of the devices' firing buttons.

On average, participants' estimates for the FtF required to fire all the configurations were significantly lower than their estimates of the point of discomfort and the point of intolerability. That is, on average, participants did not feel discomfort or intolerable discomfort in activating the firing buttons of all the Part 1 configurations. However, eleven out of thirty-one participants found at least one of the devices uncomfortable, including four participants who found at least one device intolerably uncomfortable. Participants were inconsistent with respect to which devices were judged to be at or exceeding the points of discomfort and intolerability. Participants were inconsistent with respect to which configurations were judged to be at or exceeding the points of discomfort and intolerability. However, all participants placed the 14-16 N MPF device always below their level of discomfort.

Based on the results from Part 1 of this study, it can be concluded that both MPF and TPF plunger configurations with firing buttons requiring up to 21 N of force to activate should be acceptable to most patients with severe hand RA. However, manufacturing MPF devices with firing buttons requiring up to 16 N of force to activate would be a more conservative solution. In an exemplary embodiment, the automatic injection device has an MPF plunger configuration with an FtF of between about 10 N and about 16 N. In another exemplary embodiment, the automatic injection device has an MPF plunger configuration with an FtF of between about 10 N and about 21 N. In yet another exemplary embodiment, the automatic injection device has a TPF plunger configuration with an FtF of between about 10 N and about 21 N.

Part 2: In a second part of the patient study, the plunger configuration was held constant at mid point fixed (MPF) with an ICS angle of 48°. Four different configurations of the automatic injection device 10 were tested, each requiring a different amount of force to activate the firing button of the device 10: about 12 N, about 18 N, about 23 N, and about 29 N. The objectives of the second part of the study were to determine if patients with severe RA affecting their hands: (a) reliably noticed a difference between the FtF required to activate the firing buttons of the tested MPF configurations; (b) would experience discomfort as a result of using any of the tested configurations to administer an injection twice per month; or (c) would consider the FtF required to activate the firing buttons of any tested configurations to be intolerable for an injection administered twice per month.

Participants reliably identified the 12 N device as the device requiring the lowest FtF to activate the firing button. However, participants were unable to discriminate between the FtF required to activate the firing buttons for the 18 N, 23 N, and 29 N devices.

To analyze the data from Part 2 of the study, a repeated measures ANOVA was conducted with four levels of the within-subjects manipulation of FtF: 12 N, 18 N, 23 N, and 29 N. All configurations in Part 2 used MPF plunger configurations. The purpose of this analysis was to determine if participants were able to differentiate between the FtF required to activate each device's firing button.

The study found a significant main effect for FtF ($F_{2.40, 71.90}$=31.71, p<0.001), such that participants estimated the FtF required to activate the 12 N firing button (M=5.53) to be lower than the FtF required to activate the 18 N, 23 N, and 29 N firing buttons (M=9.97, 10.14, 11.26, respectively). However, participants were not able to reliably discriminate between the FtF required to activate the 18 N, 23 N, or 29 N firing buttons.

A repeated measures ANOVA was conducted with six levels of the within-subjects manipulation of the FtF: the four configurations from Part 2 plus participants' discomfort and intolerable estimations. Participants' overall estimate of the point at which the FtF required to activate a device's firing button would cause discomfort (M=16.98) was significantly greater (p<0.005) than the estimated FtF of each of the four configurations. The discomfort estimate was also significantly (p<0.001) less than the estimate of the point at which the FtF required to activate a device's firing button would be intolerable (M=25.48).

Figure 42:
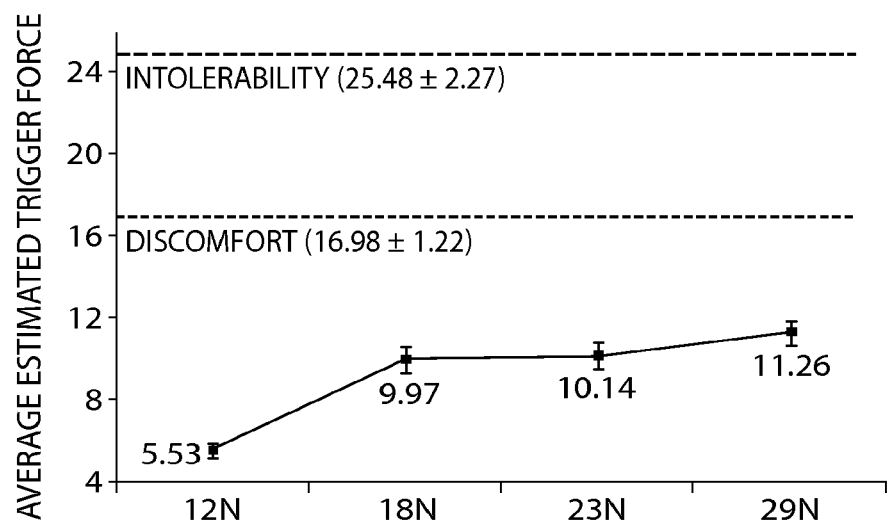
FIG. 42 provides a plot of the average estimated FtF (i.e., the force estimated by participants) versus the actual FtF of the device for a second part of the user study.

These results are summarized in FIG. 42 which provides a plot of the average estimated FtF (i.e., the force estimated by participants) versus the actual FtF of the device. The plot indicates that discomfort is felt when the estimated FtF becomes greater than about 16.98 N, and firing the firing button becomes intolerably uncomfortable when the estimated FtF becomes greater than about 25.48 N. None of the four configurations (12 N, 18 N, 23 N, 29 N) requires an average estimated FtF that falls in the "discomfort" or "intolerability" range, i.e., all fall below 16.98 N. In other words, the FtF required to activate each of the configurations' firing buttons in Part 2 was significantly lower than the FtF that would first cause participants to notice discomfort.

While participants on average estimated the points of discomfort and intolerability to be significantly greater than the FtF required to activate the firing button of any configuration in Part 2, sixteen percent (five participants) estimated both the points of discomfort and intolerability to be less than or equal to the amount of force required to activate one or more of the device's firing buttons. An additional nineteen percent (six participants) estimated only the point of discomfort to be less than or equal to the amount of force required to activate one or more of the devices' firing buttons.

Given a set of four devices with firing buttons that require 12 N, 18 N, 23 N, and 29 N of FtF to activate and that use MPF plunger configurations, RA patients with severe hand disability could reliably identify the 12 N device as the "easiest." However, these patients were unable to reliably distinguish between the 18 N, 23 N, and 29 N injection devices. All devices, including the 29 N device, were, on average, judged by the participants to be below the thresholds of noticing discomfort and becoming intolerable. However, eleven participants found at least one of the devices uncomfortable, including five participants who found at least one device intolerable. While participants were inconsistent with respect to which devices were judged to be at or exceeding the points of discomfort and intolerability, all placed the 12 N MPF device always below their level of discomfort.

Based on the results from Part 2 of this study, it can be concluded that MPF plunger configurations with up to about 29 N of FtF should be acceptable to most patients with severe hand RA. However, manufacturing MPF devices with firing buttons requiring up to about 12 N of FtF would be a more conservative solution. In an exemplary embodiment, the automatic injection device has an MPF plunger configuration with an FtF of between about 10 N and about 29 N. In another exemplary embodiment, the automatic injection device has an MPF plunger configuration with an FtF of between about 10 N and about 12 N.

Part 3: In a third part of the patient study, both MPF and TPF plunger configurations were tested, each having an FtF of 14-16 N. A more qualitative approach was used for the third part of the study to further explore participants' ability to identify and describe the differences between the MPF and TPF plunger configurations. The objectives of the third part of the study were to determine if patients with severe RA affecting their hands: (a) could describe the difference between the MPF and TPF plunger configurations when the required FtF was held constant at about 14-16 N; (b) had a preference for the MPF or TPF plunger configuration when the required FtF was held constant at about 14-16 N; and (c) would find the required FtF for the configuration that was not preferred to be intolerable, if the participant had a preference in the first place.

Most participants independently noticed the difference between the two plunger configurations, preferred the MPF configuration, and described the devices with MPF plungers as "easier to press" compared to the devices with TPF plungers. However, after further questioning, almost all participants said that the perceived difference was small and that they would not complain if an injection device with a TPF plunger configuration was prescribed to them.

During a first comparison between the MPF and TFP configurations conducted before the participants were informed that there was a different between the two devices, when participants administered mock injections with the 14-16 N MPF and TPF configurations, almost all (16 out of 19) participants identified the firing button on the MPF device as being easier to press than the firing button on the TPF device. Prior to a second comparison between the MPF and TPF devices, moderators informed the participants that there was a difference between the two devices. After being given this information and administering the second set of injections, all participants identified the firing button on the MPF device as being easier to press than the firing button on the TPF device.

Both before and after the participants were informed of the difference between the devices, most participants preferred the MPF plunger configuration. However, the difference between the FtF required to activate the devices with MPF plungers and TPF plungers was not judged by participants to be large, and only three participants would complain about the FtF required to activate the firing button on the TPF device, two of whom only gave this response for one of the two trials.

Based on the results from Part 3 of this study, it can be concluded that while patients with severe hand RA notice the difference between MPF and TPF plunger configurations for a 14-16 N device, they are unlikely to complain about a device with a TPF plunger configuration if it is prescribed to them. This is consistent with the findings from Part 1 of this study.

Based on these findings of this patient study, it is determined that improved automatic injection devices should employ an MPF plunger configuration and have an FtF of up to about 16 N. However, 21 N TPF devices and 29 N MPF devices will still be acceptable to most patients with severe RA affecting their hands. The increased FtF, as well as the possible inclusion of the TPF plunger configuration, is expected to reduce the number of misfires (compared to the 9 N MPF configuration), but is still below the participants' estimate of the point at which the required FtF would cause discomfort. In an exemplary embodiment, the automatic injection device has an MPF plunger configuration with an FtF of between about 10 N and about 16 N. In another exemplary embodiment, the automatic injection device has an MPF plunger configuration with an FtF of between about 10 N and about 21 N. In yet another exemplary embodiment, the automatic injection device has an MPF plunger configuration with an FtF of between about 10 N and about 29 N.

INCORPORATION BY REFERENCE

The contents of all cited references (including literature references, patents, patent applications, and websites) that maybe cited throughout this application are hereby expressly incorporated by reference in their entirety for any purpose. The practice of the exemplary embodiments will employ, unless otherwise indicated, conventional techniques of molding and FtF measurement, which are well known in the art.

Equivalents

Exemplary embodiments may be embodied in other specific forms without departing from the spirit or essential characteristics thereof. The foregoing exemplary embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

What is claimed is:

1. A syringe plunger formed of a polymeric material, the syringe plunger comprising:
   a pressurizer disposed at a first end; and
   a second bifurcated end having a first plunger arm with an end surface, a first transition edge defining an outer perimeter of the end surface of the first plunger arm, a second transition edge, and a third transition edge; and a second plunger arm with an end surface, a first transition edge defining an outer perimeter of the end surface of the second plunger arm, a second transition edge, and a third transition edge, the second bifurcated end including:
   a first contact surface defined by a surface between the first transition edge of the first plunger arm and the second transition edge of the first plunger arm and a surface between the first transition edge of the second plunger arm and the second transition edge of the second plunger arm, the first contact surface configured to initially contact a firing engagement mechanism;
   a second contact surface defined by a surface between the second transition edge of the first plunger arm and the third transition edge of the first plunger arm and a surface between the second transition edge of the second plunger arm and the third transition edge of the second plunger arm, the second contact surface configured to contact the firing engagement mechanism subsequent to contact by the first contact surface.

2. The automatic injection device of claim 1, wherein the firing engagement mechanism is configured to engage the first and second contact surfaces of the first plunger arm and the second plunger arm, the firing engagement mechanism actuating the syringe plunger when the firing engagement mechanism is activated by a minimum force of between 5 N and 25 N.

3. The automatic injection device of claim 2, wherein, upon actuation of the syringe plunger, the pressurizer of the syringe plunger pressurizes a dose of TNF inhibitor in a syringe barrel and causes the dose of TNF inhibitor to be expelled from the syringe barrel.

4. The automatic injection device of claim 1, wherein the polymeric material of the syringe plunger has a flexural modulus of between 2,000 MPa and 5,500 MPa.

5. The automatic injection device of claim 1, wherein the first and second contact surfaces have a surface texture that is substantially rough.

6. The automatic injection device of claim 1, wherein the first and second contact surfaces have a surface texture that is substantially smooth.

7. The automatic injection device of claim 1, wherein the second contact surface is disposed at a second angle of 6°-38° relative to the longitudinal axis of the syringe plunger.

8. The automatic injection device of claim 1, wherein the second contact surface is disposed at a second angle of 8°-25° relative to the longitudinal axis of the syringe plunger.

9. The automatic injection device of claim 1, wherein the first and second plunger arms are separated by a third angle of between 0.5° and 2.0°.

10. The automatic injection device of claim 1, wherein the first and second plunger arms are separated by a distance of between 2.55 mm and 4.25mm.

11. The automatic injection device of claim 1, wherein the first and second plunger arms are separated by a distance of 3.05 mm.

12. The automatic injection device of claim 1, wherein the polymeric material is selected from the group consisting of thermoplastic materials and thermosetting materials.

13. The automatic injection device of claim 12, wherein the thermoplastic materials are selected from the group consisting of polyacetal, polycarbonate, polyacrylate, polyamide, polyester, acryonitrile-butadiene-styrene (ABS), polyvinyl chloride (PVC) and their copolymers, terpolymers, and filled composites thereof.

14. The automatic injection device of claim 13, wherein the polyacetal materials are selected from the group consisting of acetal homopolymers, copolymers, and filled materials thereof.

15. The automatic injection device of claim 14, wherein the filled materials are glass sphere filled or glass fiber filled.

16. The automatic injection device of claim 12, wherein the thermosetting materials are selected from the group consisting of epoxy, acrylic, urethane, ester, vinyl ester, epoxy-polyester, acrylic-urethane, and flurovinyl.

17. The automatic injection device of claim 16, wherein the acrylic material comprises a reactive functionality selected from the group consisting of an acid, a hydroxyl group, and an epoxy group.

18. The automatic injection device of claim 16, wherein the epoxy material comprises a reactive functionality that can be cured by a method selected from the group consisting of visible, ultraviolet and thermal crosslinking.

19. The automatic injection device of claim 12, wherein the thermosetting materials are selected from the group consisting of an epoxy homopolymer, copolymer or filled composite thereof.

20. The automatic injection device of claim 1, wherein the first contact surface has an open segment between the first and second plunger arms.

21. The automatic injection device of claim 1, wherein the first and second plunger arms have a top point fixed configuration.

22. The automatic injection device of claim 1, wherein the first and second plunger arms have a mid-point fixed configuration.

23. The automatic injection device of claim 1, wherein the second bifurcated end further comprises:
a third contact surface defined by a conical surface disposed on a side of the third transition edge of the first plunger arm opposite the second contact surface and a conical surface disposed on a side of the third transition edge of the second plunger arm opposite the second contact surface, the third contact surface configured to contact a portion of the firing body.

24. The automatic injection device of claim 23, wherein the third contact surface is disposed at an angle of 62 degrees to 82 degrees relative to the longitudinal axis of the syringe plunger.

* * * * *

UNITED STATES PATENT AND TRADEMARK OFFICE
CERTIFICATE OF CORRECTION

| | | |
|---|---|---|
| PATENT NO. | : 9,561,328 B2 | Page 1 of 1 |
| APPLICATION NO. | : 14/109532 | |
| DATED | : February 7, 2017 | |
| INVENTOR(S) | : Shang et al. | |

It is certified that error appears in the above-identified patent and that said Letters Patent is hereby corrected as shown below:

In the Claims

Column No: 77, Line(s): 24, Claim: 13, "acryonitrile-butadiene-styrene" to read as –acrylonitrile-butadiene-styrene–

Column No: 77, Line(s): 36, Claim: 16, "flurovinyl" to read as –fluorovinyl–

Signed and Sealed this
Twenty-eighth Day of November, 2017

Joseph Matal
*Performing the Functions and Duties of the*
*Under Secretary of Commerce for Intellectual Property and*
*Director of the United States Patent and Trademark Office*